United States Patent
Takats et al.

(10) Patent No.: US 10,026,599 B2
(45) Date of Patent: Jul. 17, 2018

(54) RAPID EVAPORATIVE IONISATION MASS SPECTROMETRY ("REIMS") AND DESORPTION ELECTROSPRAY IONISATION MASS SPECTROMETRY ("DESI-MS") ANALYSIS OF SWABS AND BIOPSY SAMPLES

(71) Applicant: Micromass UK Limited, Wilmslow (GB)

(72) Inventors: Zoltan Takats, Cambridge (GB); Emrys Jones, Manchester (GB); James Ian Langridge, Sale (GB); Michael Raymond Morris, Glossop (GB); Tamas Karancsi, Budapest (HU); Steven Derek Pringle, Darwen (GB); Julia Balog, Solymar (HU); Daniel Simon, Morichida (HU); Lajos Godorhazy, Erd (HU); Daniel Szalay, Budapest (HU); Keith Richardson, High Peak (GB); Phillip Robert Bennett, London (GB); David Alan MacIntyre, Isleworth (AU); Pamela Pruski, London (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/555,783

(22) PCT Filed: Mar. 7, 2016

(86) PCT No.: PCT/GB2016/050621
§ 371 (c)(1),
(2) Date: Sep. 5, 2017

(87) PCT Pub. No.: WO2016/142691
PCT Pub. Date: Sep. 15, 2016

(65) Prior Publication Data
US 2018/0047554 A1    Feb. 15, 2018

(30) Foreign Application Priority Data
Mar. 6, 2015   (GB) .................................. 1503879.7

(51) Int. Cl.
*H01J 49/04* (2006.01)
*G01N 27/62* (2006.01)
(Continued)

(52) U.S. Cl.
CPC ........ *H01J 49/049* (2013.01); *A61B 10/0041* (2013.01); *A61B 10/0283* (2013.01);
(Continued)

(58) Field of Classification Search
USPC ....................................................... 250/288
See application file for complete search history.

(56) References Cited

U.S. PATENT DOCUMENTS

| 5,374,755 A | 12/1994 | Neue et al. |
| 5,830,214 A | 11/1998 | Flom et al. |

(Continued)

FOREIGN PATENT DOCUMENTS

WO    2013/148162    10/2013

OTHER PUBLICATIONS

Agar, Nathalie et al., "*Development of Stereotactic Mass Spectrometry for Brain Tumor Surgery*", Biosis, Neurosurgery Online, vol. 68, No. 2, (2011).
(Continued)

*Primary Examiner* — Kiet T Nguyen

(57) ABSTRACT

A method is disclosed comprising providing a biological sample on a swab, directing a spray of charged droplets onto a surface of the swab in order to generate a plurality of analyte ions, and analyzing the analyte ions.

16 Claims, 42 Drawing Sheets

(51) Int. Cl.

| | | |
|---|---|---|
| *H01J 49/00* | (2006.01) | |
| *H01J 49/16* | (2006.01) | |
| *A61B 10/00* | (2006.01) | |
| *A61F 13/38* | (2006.01) | |
| *A61B 10/02* | (2006.01) | |
| *A61B 18/04* | (2006.01) | |
| *A61B 18/18* | (2006.01) | |
| *A61B 18/20* | (2006.01) | |
| *G01N 33/487* | (2006.01) | |
| *A61B 18/00* | (2006.01) | |
| *A61B 17/32* | (2006.01) | |

(52) U.S. Cl.
CPC ........ *A61B 18/042* (2013.01); *A61B 18/1815* (2013.01); *A61B 18/20* (2013.01); *A61F 13/38* (2013.01); *G01N 27/622* (2013.01); *G01N 33/487* (2013.01); *H01J 49/0031* (2013.01); *H01J 49/16* (2013.01); *A61B 2010/0083* (2013.01); *A61B 2017/320069* (2017.08); *A61B 2018/00577* (2013.01); *A61B 2218/008* (2013.01)

(56) References Cited

U.S. PATENT DOCUMENTS

| | | | |
|---|---|---|---|
| 5,836,909 | A | 11/1998 | Cosmescu |
| 6,032,673 | A | 3/2000 | Savage et al. |
| 7,329,253 | B2 | 2/2008 | Brounstein et al. |
| 7,365,309 | B2 | 4/2008 | Denny et al. |
| 8,448,493 | B2 | 5/2013 | McIntyre et al. |
| 9,046,448 | B2 | 6/2015 | Takats |
| 9,053,914 | B2 | 6/2015 | Pringle et al. |
| 9,082,603 | B2 | 7/2015 | Bajic |
| 9,120,083 | B2 | 9/2015 | Wyndham et al. |
| 9,255,907 | B2 | 2/2016 | Heanue et al. |
| 9,281,174 | B2 | 3/2016 | Takats |
| 9,287,100 | B2 | 3/2016 | Szalay et al. |
| 9,731,219 | B2 | 8/2017 | Wang et al. |
| 2003/0135222 | A1 | 7/2003 | Baska |
| 2008/0073503 | A1* | 3/2008 | Wu ................... G01N 27/622 250/283 |
| 2008/0073512 | A1 | 3/2008 | Siuzdak et al. |
| 2009/0126891 | A1 | 5/2009 | Koivunen et al. |
| 2015/0192590 | A1 | 7/2015 | Sodeoka et al. |
| 2016/0002696 | A1 | 1/2016 | Galiano |

OTHER PUBLICATIONS

Ahlf, Dorothy R. et al., "Correlated Mass Spectrometry Imaging and Confocal Raman Microscopy for Studies of Three-Dimensional Cell Culture Sections", Analyst, vol. 139, No. 18, pp. 4578 (2014).

Azimzadeh, Omid et al., "Formalin-Fixed Paraffin-Embedded (FFPE) Proteome Analysis Using Gel-Free and Gel-Based Proteomics", Journal of Proteome Research, vol. 9, No. 9, pp. 4710-4720 (2010).

Balgley, Brian M. et al., "Evaluation of Archival Time on Shotgun Proteomics of Formalin-Fixed and Paraffin-Embedded Tissues", Journal of Proteome Research, Vol. 8 No. 2, pp. 917-925 (2009).

Balog, Julia et al., "Identification of Biological Tissues by Rapid Evaporative Ionization Mass Spectrometry", Analytical Chemistry, vol. 82, No. 17, pp. 7343-7350 (2010).

Balog, Julia et al., "Supporting Information for Identification of Biological Tissues by Rapid Evaporative Ionization Mass Spectrometry", pp. S1-S9, http://pubs.acs.org/doi/suppl/10.1021/ac101, (2013).

Balog, J. et al., "Intraoperative Tissue Identification Using Rapid Evaporative Ionization Mass Spectrometry", Science Translational Medicine, vol. 5, No. 194, pp. 194ra93 (2013).

Balog, J. et al., "Supplementary Materials: Intraoperative Tissue Identification Using Rapid Evaporative Ionization Mass Spectrometry", Science Translational Medicine, vol. 5, No. 194, pp. 194ra93 (2013).

Bean, Heather D. et al., "Bacterial Volatile Discovery Using Solid Phase Microextraction and Comprehensive Two-Dimensional Gas Chromatographytime-of-Flight Mass Spectrometry", Journal of Chromatography B, vol. 901, pp. 41-46 (2012).

Bellet, V. et al., "Proteomic Analysis of RCL2 Paraffin-Embedded Tissues", Journal of Cellular and Molecular Medicine, vol. 12, No. 5B, pp. 2027-2036 (2008).

Bocklitz, T.W. et al., "Deeper Understanding of Biological Tissue: Quantitative Correlation of MALDI-TOF and Raman Imaging", Analytical Chemistry, vol. 85, No. 22, pp. 10829-10834 (2013).

Cole, Laura M. et al., "Mass Spectrometry Imaging for the Proteomic Study of Clinical Tissue", Proteomics-Clinical Applications, vol. 9, No. 3-4, pp. 335-341 (2015).

Crawshaw, Benjamin et al., "Gastrointestinal Surgery: Real-Time Tissue Identification During Surgery", Nature Review/Gastroenterology & Hepatology Nature, vol. 10, No. 11. pp. 624-625, 2013.

Cselik, Z. et al., "Impact of Infrared Laser Light-Induced Ablation at Different Wavelengths on Bovine Intervertebral Disc Ex Vivo: Evaluation with Magnetic Resonance Imaging and Histology", Lasers In Surgery and Medicine, vol. 44, No. 5, pp. 406-412 (2012).

Davies, T.J. et al., "Volatile Products from Acetylcholine as Markers in the Rapid Urine Test Using Head-Space Gas-Liquid Chromatography B: Biomedical Sciences and Applications", Journal of Chromatography, vol. 307, pp. 11-21 (1984).

European Commission, "ISD Report Summary", http://cordis.europa.eu/result/rcn/163435_e, (2016).

Fahy, Eoin, et al., "Lipid Classification, Structures and Tools", Biochimica at Biophysica Acta (BBA)—Molecular and Cell Biology of Lipids, vol. 1811, No. 11, pp. 637-647 (2011).

Gerbig, Stefanie et al., "Analysis of Colorectal Adenocarcinoma Tissue by Desorption Electrospray Ionization Mass Spectrometric Imaging", Analytical and Bioanalytical Chemistry, vol. 403, No. 8, pp. 2315-2325 (2012).

Golf, Ottmar et al., "Rapid Evaporative Ionization Mass Spectrometry Imaging Platform for Direct Mapping from Bulk Tissue and Bacterial Growth Media", Analytical Chemistry, vol. 87, No. 5, pp. 2527-2534 (2015).

Golf, Ottmar et al., "XMS: Cross-Platform Normalization Method for Multimodal Mass Spectrometric Tissue Profiling", Journal of the American Society for Mass Spectrometry, vol. 26, No. 1, pp. 44-54 (2014).

Guenther, Sabine et al., "Electrospray Post-Ionization Mass Spectrometry of Electrosurgical Aerosols", Journal of The American Society for Mass Spectrometry, vol. 22, No. 11, pp. 2082-2089 (2011).

Gustafsson, Ove J.R. et al., "Proteomic Developments in the Analysis of Formalin-Fixed Tissue", Biochimica et Biophysica Acta, vol. 1854, No. 6, pp. 559-580, 2014.

Hobbs, S.K. et al., "Magnetic Resonance Image-Guided Proteomics of Human Glioblastoma Multiforme", Journal of Magnetic Resonance Imaging, vol. 18, pp. 530-536 (2003).

Hsu, Cheng-Chih et al., "Visualizing Life with Ambient Mass Spectrometry", Current Opinion in Biotechnology, vol. 31, pp. 24-34 (2015).

Jadoul, L. et al., "Matrix-Assisted Laser Desorption/Ionization Mass Spectrometry and Raman Spectroscopy: An Interesting Complementary Approach for Lipid Detection in Biological Tissues", European Journal of Lipid Science and Technology. vol. 116, No. 8, pp. 1080-1086 (2014).

Jain, M. et al., "Metabolite Profiling Identifies a Key Role for Glycine in Rapid Cancer Cell Proliferation", American Association for the Advancement of Science, vol. 336, No. 6084, pp. 1040-1044 (2012).

Jarmusch, Alan K et al., "Detection of Strep Throat Causing Bacterium Directly from Medical Swabs by Touch Spray-Mass Spectrometry", Analyst, vol. 139, No. 19, pp. 4785 (2014).

Jarmusch, Alan K. et al., "Supplemental Information Detection of Strep Throat Causing Bacterium Directly from Medical Swabs by Touch Spray-Mass Spectrometry", http://www.rsc.org/suppdata/an/e4/c4an00959 (2016).

(56) References Cited

OTHER PUBLICATIONS

Lazova, Rossitza et al., "*Imaging Mass Spectrometry—A New and Promising Method to Differentiate Spitz Nevi From Spitzoid Malignant Melanomas*", American Journal of Dermatopathology, vol. 34, No. 1, pp. 82-90 (2012).

Li, Yan et al., "*Aberrant Mucin5B Expression in Lung Adenocarcinomas Detected by iTRAQ Labeling Quantitative Proteomics and Immunohistochemistry*", Clinical Proteomics, Vol. 10, No. 1, pp. 15 (2013)

Lieuwe, D.J. et al., "*Volatile Metabolites of Pathogens: A Systematic Review*", PLoS Pathogens, vol. 9, No. 5, pp. 1003311, 2013.

Luge, S. et al., "*Use of a Lower Power, High Frequency Stabilized Capacitive Plasma Combined with Graphite Furnace Vaporization for the Atomic Emission Spectrometric Analysis of Serum Samples*", Analytical Chimica Acta, vol. 332, No. 2-3, pp. 193-199 (1996).

Mccullough, Bryan J. et al., "*On-Line Reaction Monitoring by Extractive Electrospray Ionisation*", Rapid Communications in Mass Spectrometry, vol. 25, No. 10, pp. 1445-1451 (2011).

Murray, Patrick R, "*What Is New in Clinical Microbiology-Microbial Identification by MALDI-TOF Mass Spectrometry*", Journal of Molecular Diagnostics, vol. 14, No. 5, pp. 419-423 (2012).

Nicholson, Jeremy K. et al., "*Metabolic Phenotyping in Clinical and Surgical Environments*", Nature, vol. 491, No. 7424 pp. 384-392 (2012).

Pirro, Valentina et al., "*Direct Drug Analysis from Oral Fluid Using Medical Swab Touch Spray Mass Spectrometry*", Analytica Chimica Acta, vol. 861, pp. 47-54, 2015.

Plata, N. et al., "*Aerosols Sampling Using a New Cryogenic Instrument*", Journal of Aerosol Science, vol. 37, No. 12, pp. 1871-1875 (2006).

Rodriguez-Rigueiro, Teresa et al., "*A Novel Procedure for Protein Extraction from Formalin-Fixed Paraffin-Embedded Tissues*", Proteomics, vol. 11, No. 12, pp. 2555-2559 (2011).

Schafer, Karl-Christian et al., "*In Vivo, In Situ Tissue Analysis Using Rapid Evaporative Ionization Mass Spectrometry*", Angewandte Chemie International, vol. 48, No. 44, pp. 8240-8242 (2009).

Shane, Ellis R. et al., "*Surface Analysis of Lipids by Mass Spectrometry: More Than Just Imaging*", Progress in Lipid Research Pergamon Press, vol. 52, No. 4, pp. 329-353, 2013.

Shoemaker, Robert H., "*The NCI60 Human Tumour Cell Line Anticancer Drug Screen*", (2013).

Strittmatter, N. et al., "*Anaylsis of Intact Bacteria Using Rapid Evaporative Ionisation Mass Spectrometry*", Chemical Communications, vol. 49, No. 55, pp. 6188 (2013).

Strittmatter, N. et al., "*Characterization and Identification of Clinically Relevant Microorganisms Using Rapid Evaporative Ionization Mass Spectrometry*", Analytical Chemistry, vol. 86, No. 13, pp. 6555-6562 (2014).

Strittmatter, N. et al., "*Taxon-Specific Markers for the Qualitative and Quantitative Detection of Bacteria in Human Samples*", http://www.msacl.org/2015_US_Long_Abstract.

Tait, Emma et al., "*Identification of Volatile Organic Compounds Produced by Bacteria Using HS-SPME-GC-MS*", Journal of Chromatographic Sci, pp. 1-11, 2013.

Uribe, D.O. et al., "*Piezoelectric Self-Sensing System for Tactile Intraoperative Brain Tumor Delineation in Neurosurgery*", Proceedings of the 31$^{st}$ Annual International Conference of the IEEE Engineering in Medicine and Biology Society: Engineering the Future of BioMedicine, pp. 737-740 (2009).

Vander Wilp, W. et al., "*Lead in Micro-Samples of Whole Blood by Rhenium-Cup in-Torch Vaporization-Inductively Coupled Plasma-Atomic Emission Spectrometry (ITV-ICP-AES)*", Fresenius' Journal of Analytical Chemistry, vol. 368, No. 7, pp. 734-736 (2000).

Vircks, Kyle E. et al., "*Rapid Screening of Synthetic Cathinones as Trace Residues and in Authentic Seizures Using a Portable Mass Spectrometer Equipped with Desorption Electrospray Ionization*", Rapid Communications in Mass Spectrometry, vol. 26, No. 23, pp. 2665-2672 (2012).

\* cited by examiner

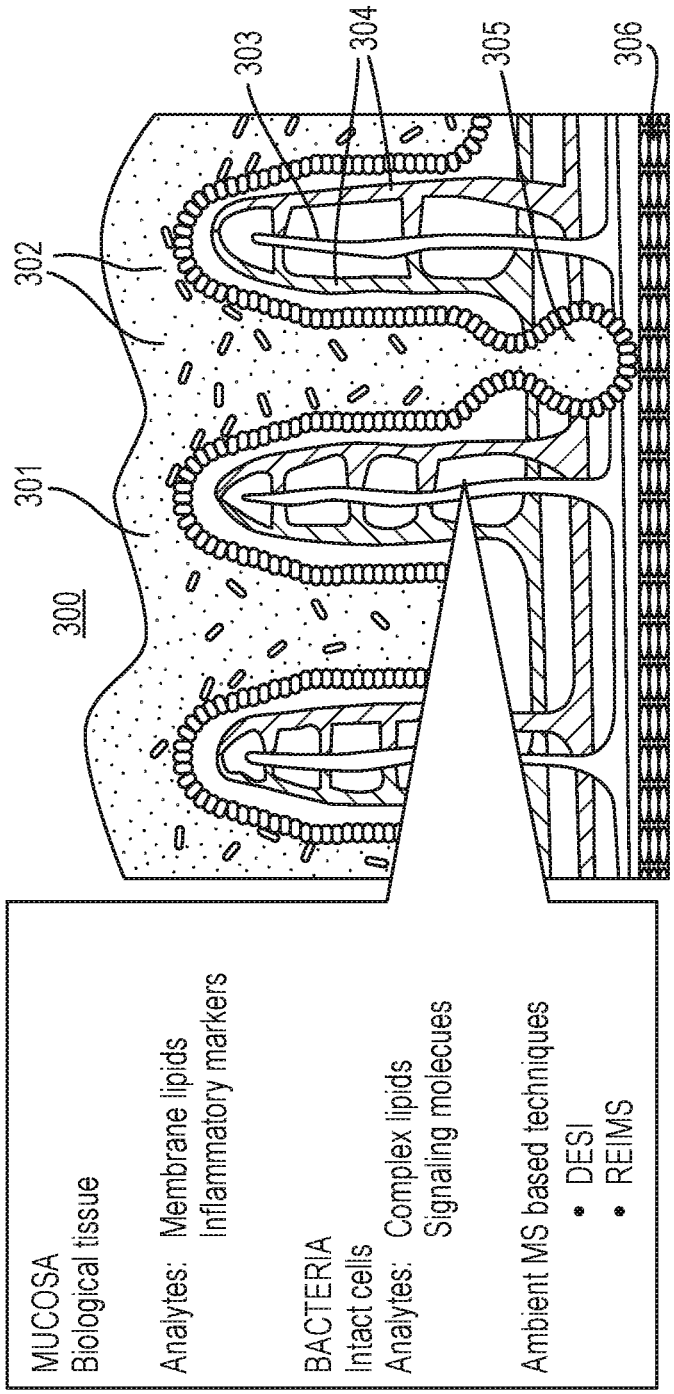

Fig. 4

Development of a real time point of care (POC) diagnostic method to investigate clinical disorders such as:

- Infections (pharyngitis, bronchitis)
- Change in microbiome (pre-term delivery)
- Immunological disorder (asthma, allergy)
- Cancer and pre-cancerous states Microbe identification Biomarker profiling Swabs: Standard collection device (clinical microbiology, gene and drug testing...)

Swabs for sampling

MS-based real-time POC

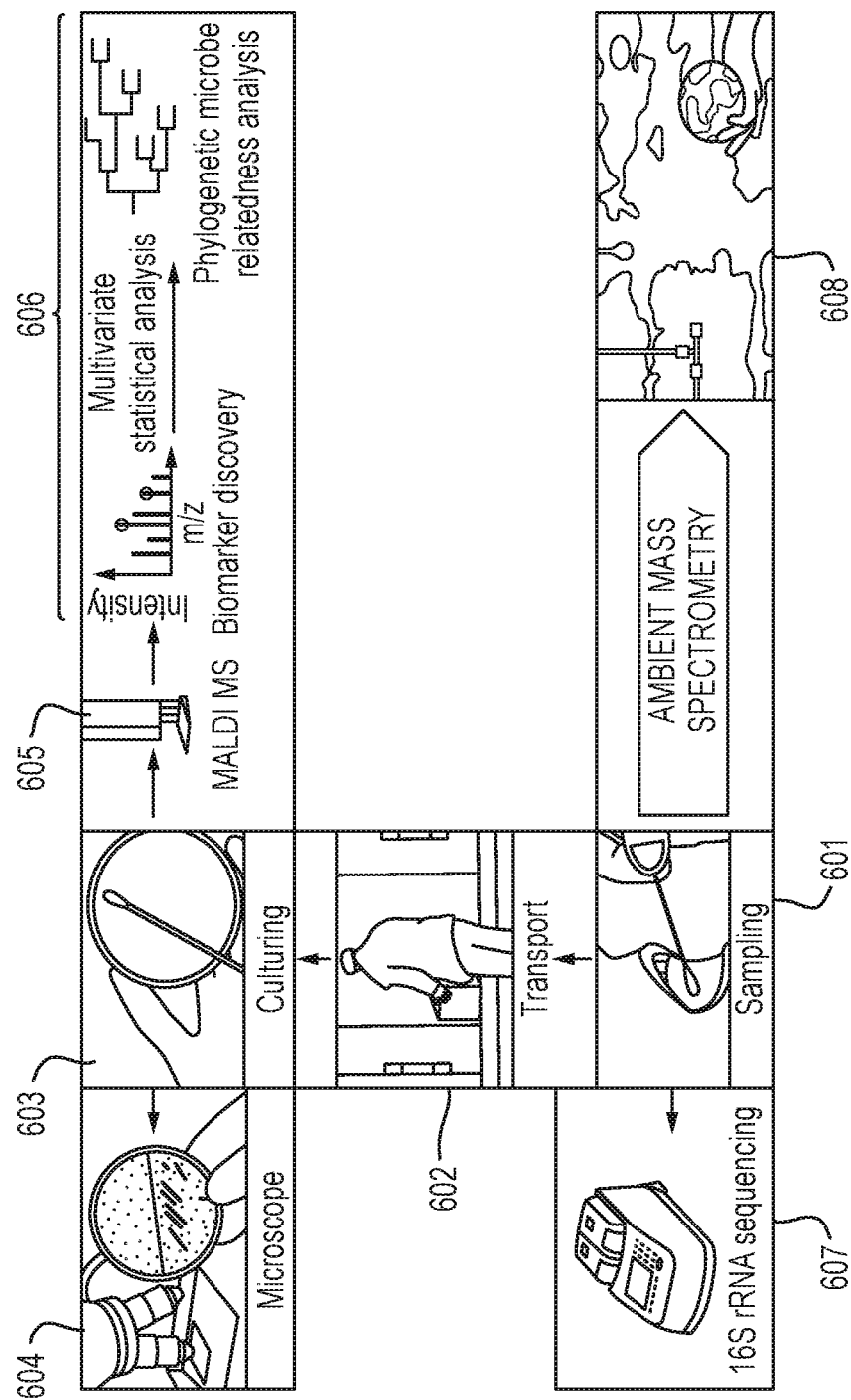

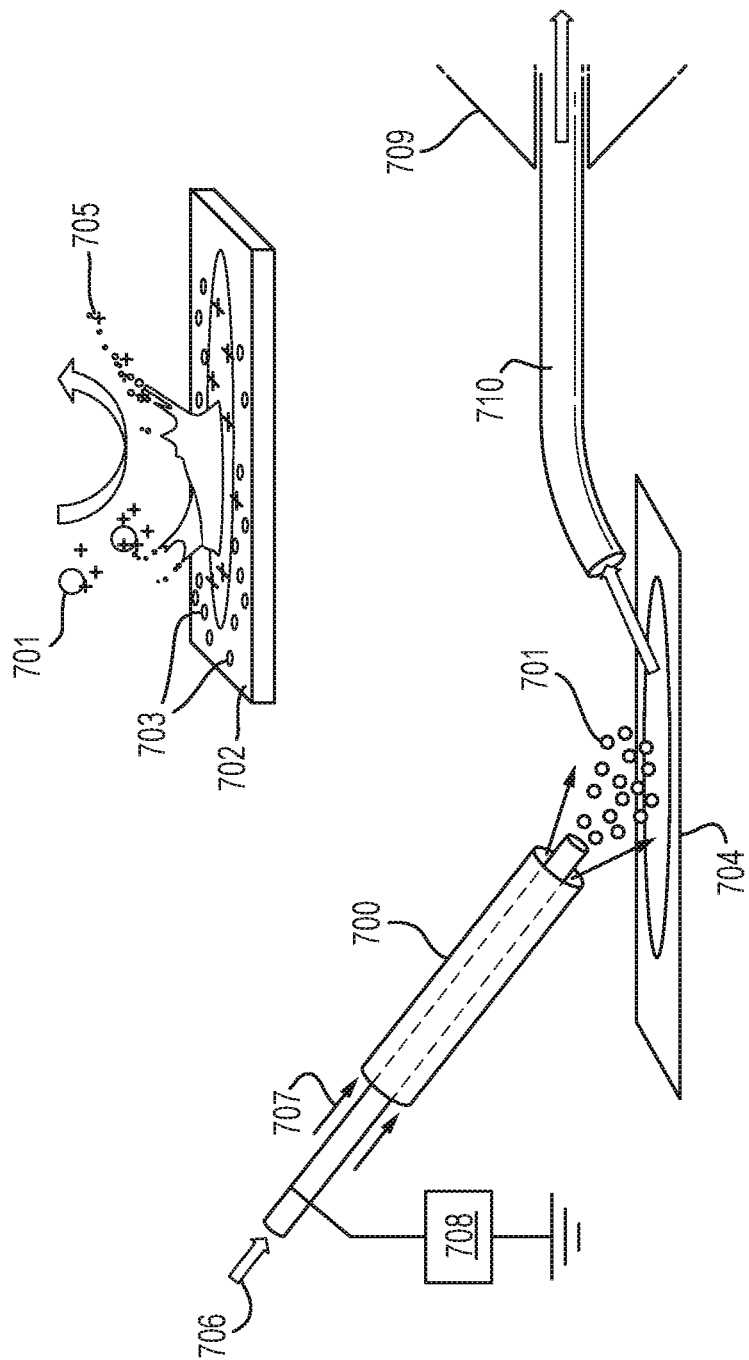

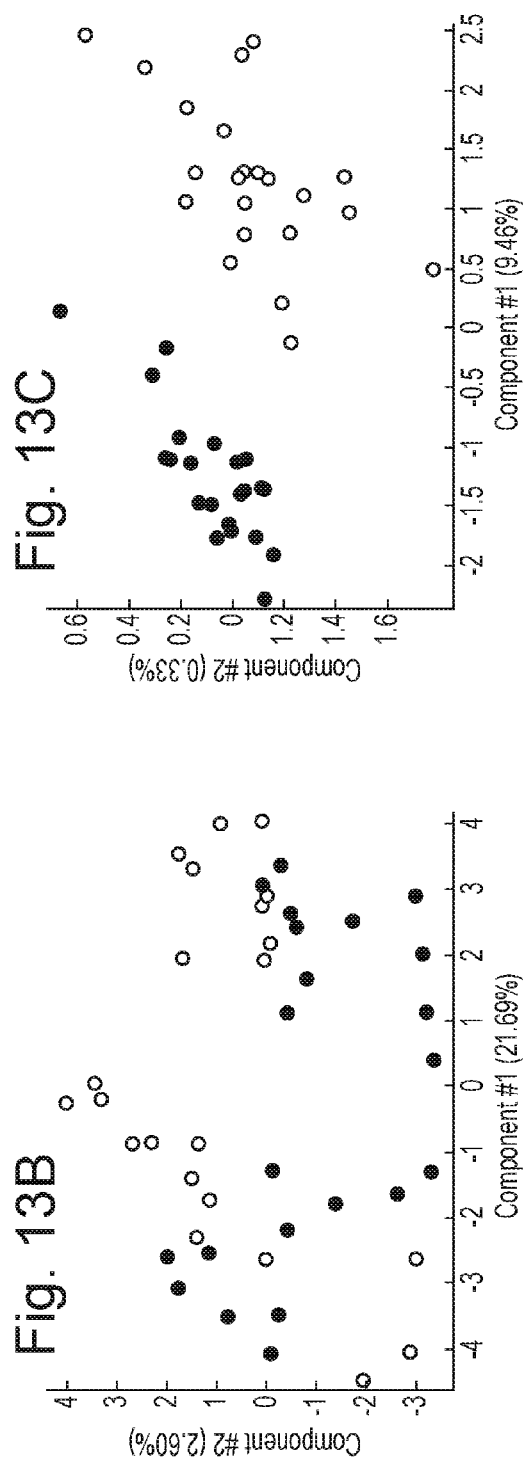

Fig. 14A
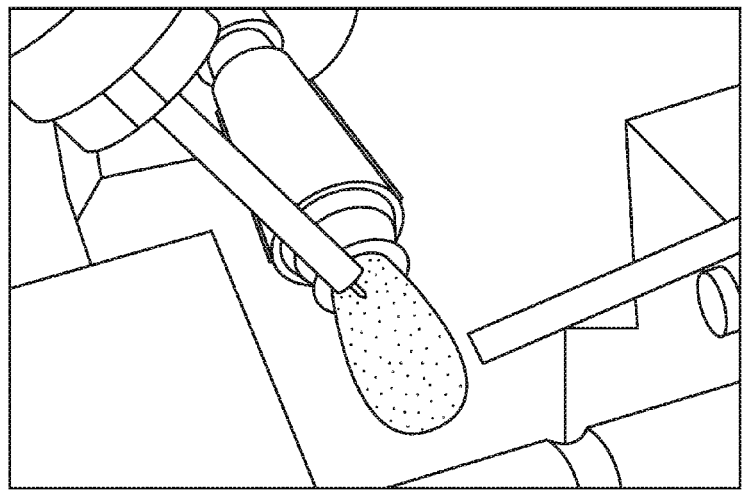
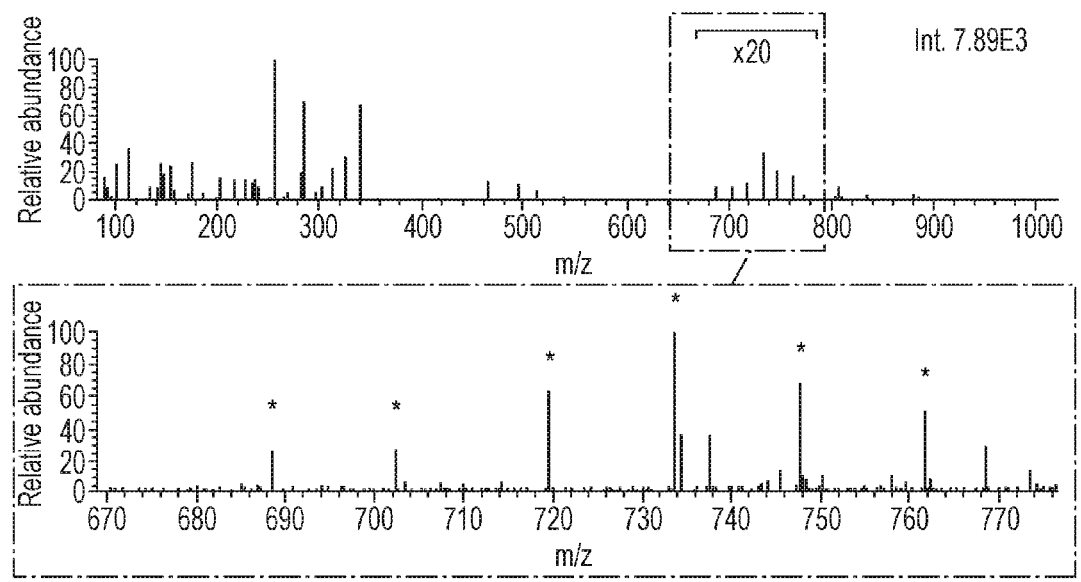

Fig. 14B
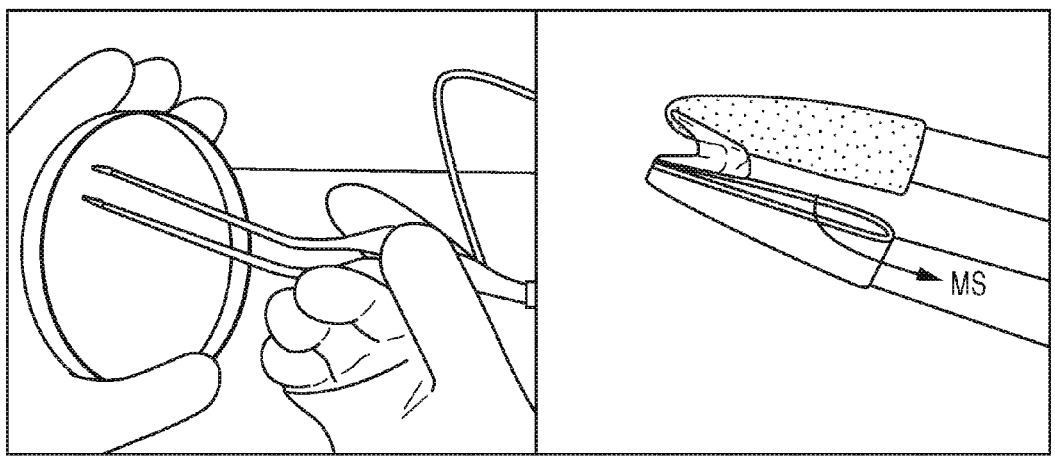
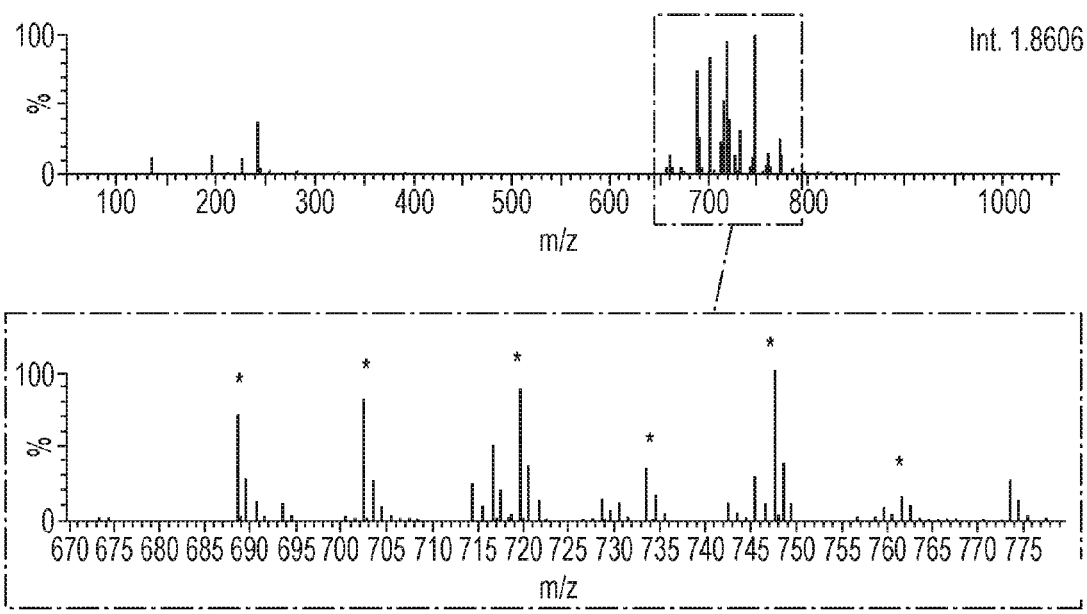

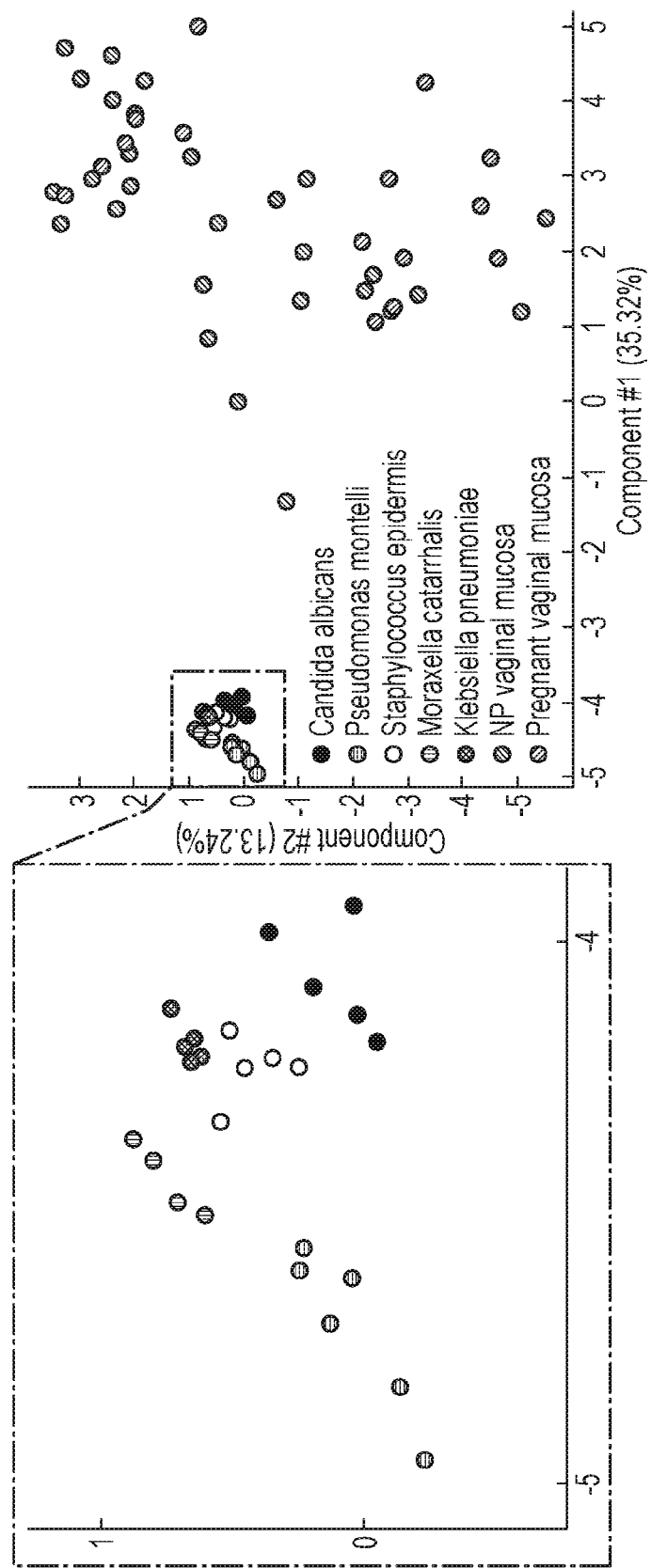

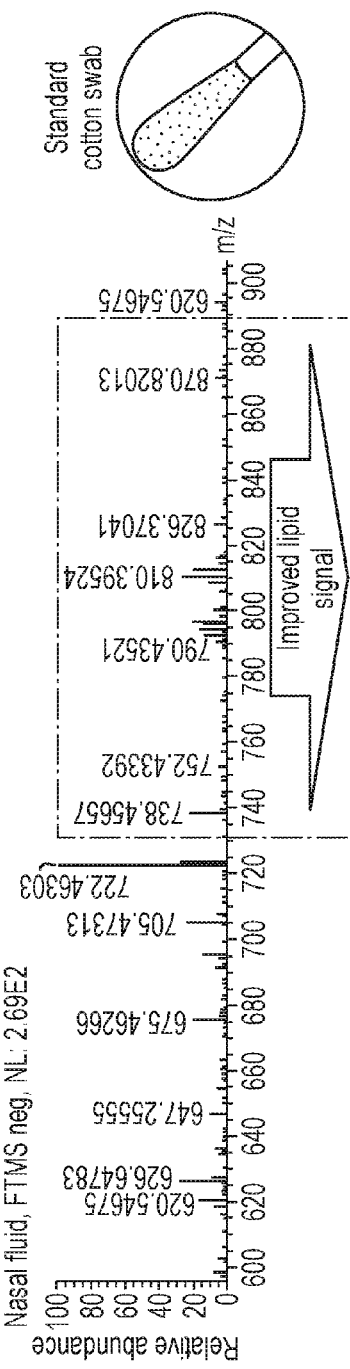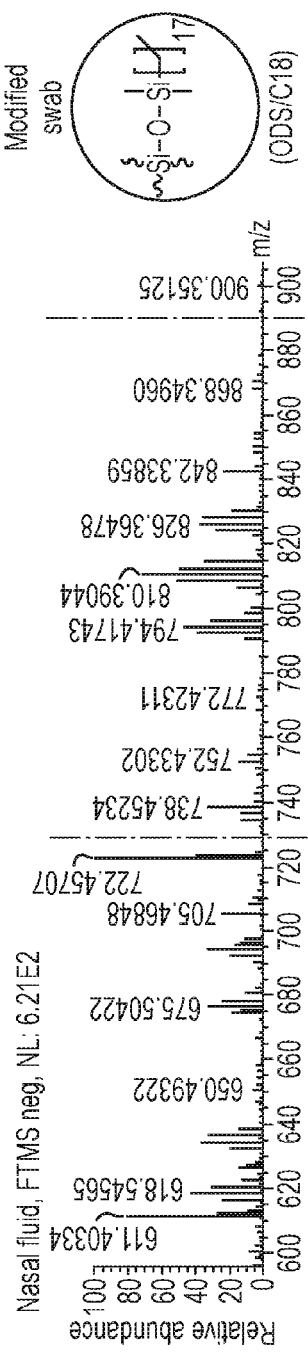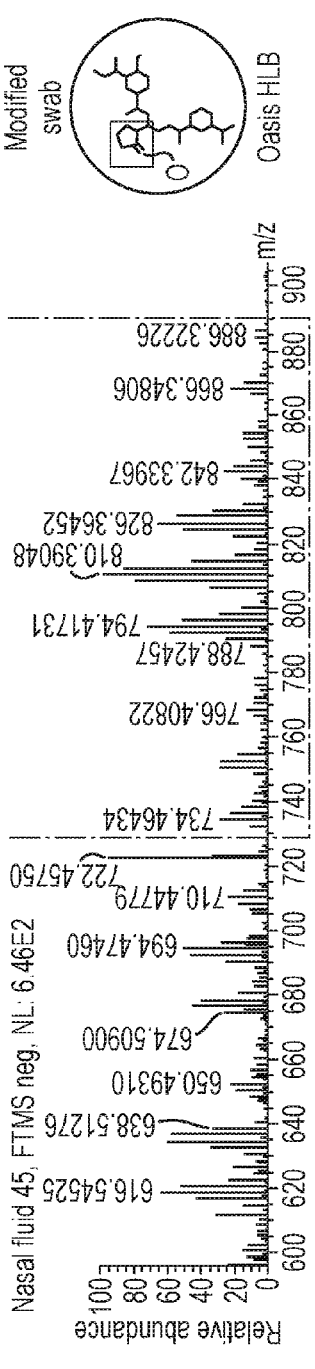
Fig. 20A
Fig. 20B
Fig. 20C

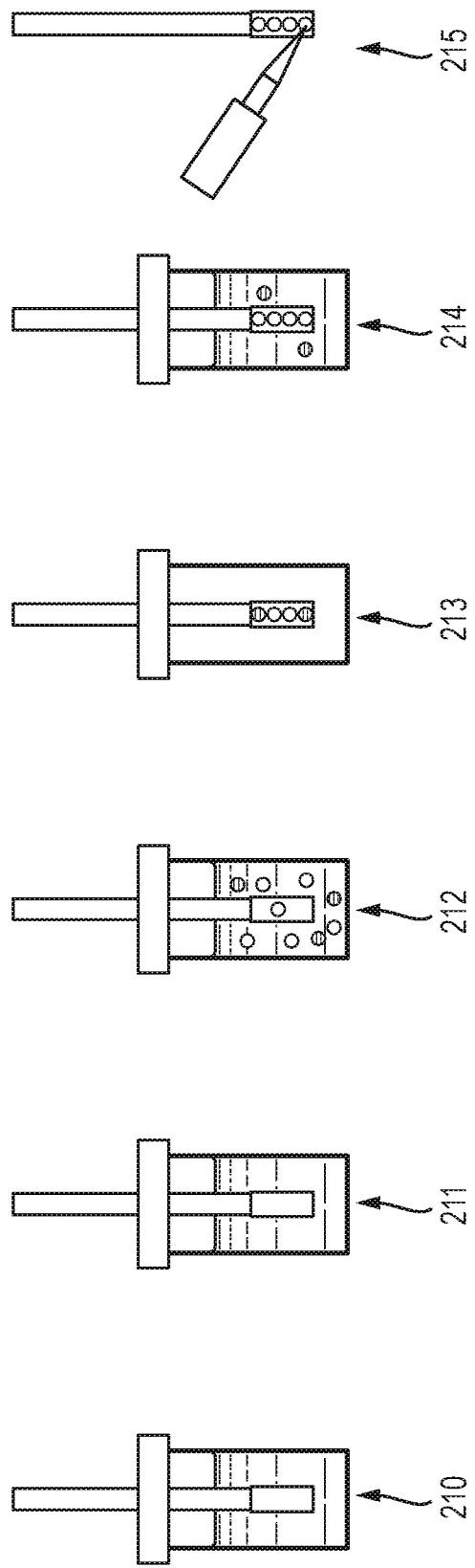

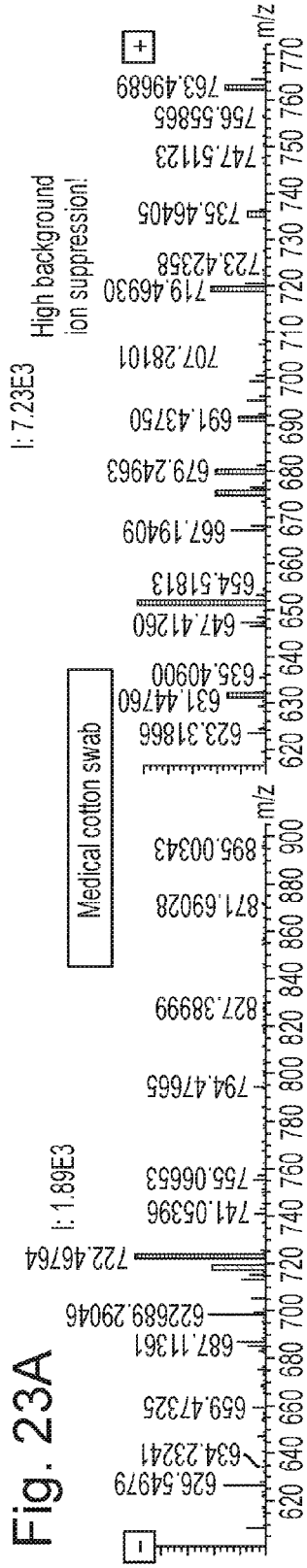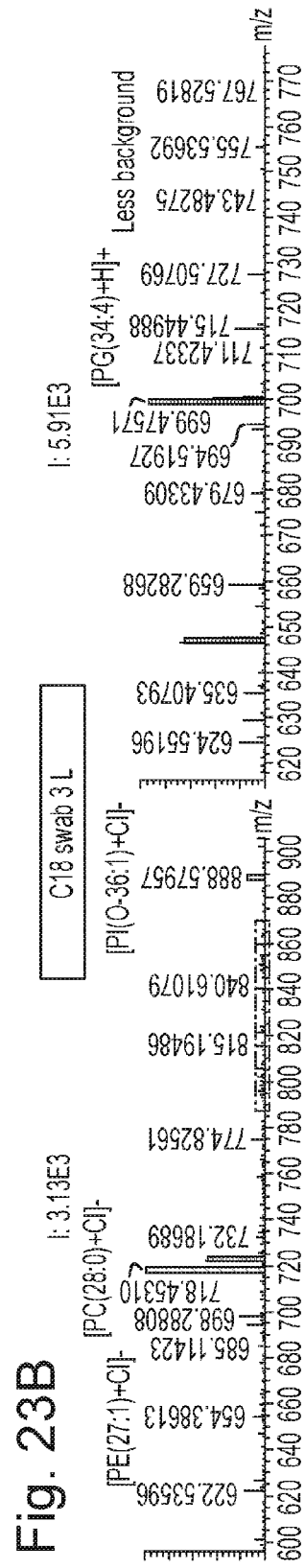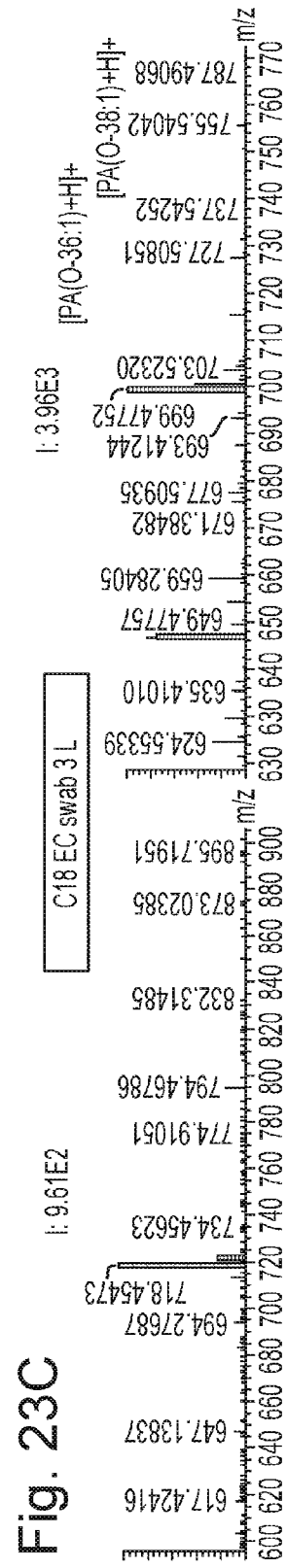

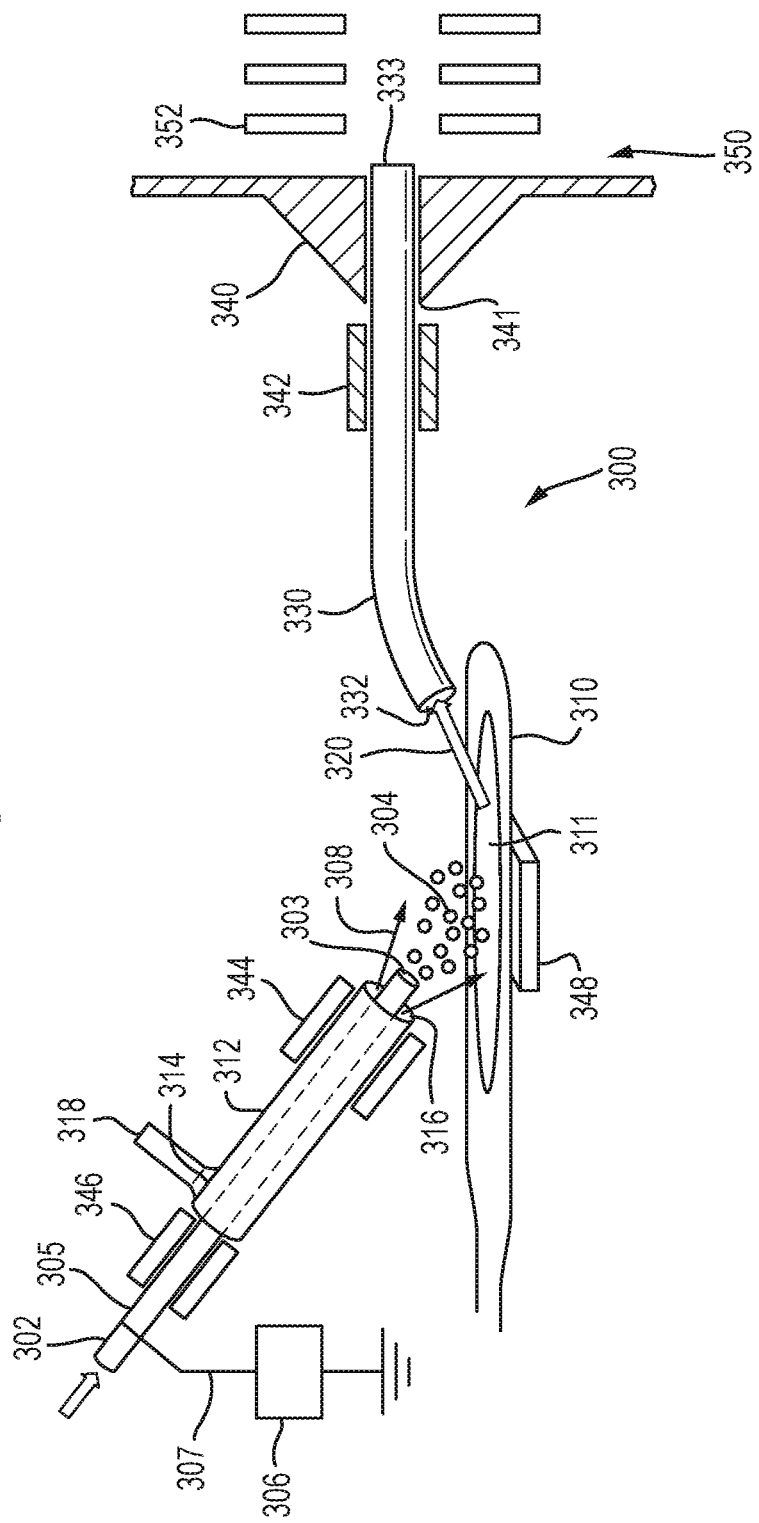

RAPID EVAPORATIVE IONISATION MASS SPECTROMETRY ("REIMS") AND DESORPTION ELECTROSPRAY IONISATION MASS SPECTROMETRY ("DESI-MS") ANALYSIS OF SWABS AND BIOPSY SAMPLES

CROSS-REFERENCE TO RELATED APPLICATIONS

This application represents the U.S. National Phase of International Application number PCT/GB2016/050621 entitled "Rapid Evaporative Ionisation Mass Spectrometry ("REIMS") and Desorption Electrospray Ionisation Mass Spectrometry ("DESI-MS") Analysis of Swabs and Biopsy Samples" filed 7 Mar. 2016, which claims priority from and the benefit of United Kingdom patent application No. 1503876.3 filed on 6 Mar. 2015, United Kingdom patent application No. 1503864.9 filed on 6 Mar. 2015, United Kingdom patent application No. 1518369.2 filed on 16 Oct. 2015, United Kingdom patent application No. 1503877.1 filed on 6 Mar. 2015, United Kingdom patent application No. 1503867.2 filed on 6 Mar. 2015, United Kingdom patent application No. 1503863.1 filed on 6 Mar. 2015, United Kingdom patent application No. 1503878.9 filed on 6 Mar. 2015, United Kingdom patent application No. 1503879.7 filed on 6 Mar. 2015 and United Kingdom patent application No. 1516003.9 filed on 9 Sep. 2015. The entire contents of these applications are incorporated herein by reference.

FIELD OF THE INVENTION

The present invention relates generally to mass spectrometers and in particular to the analysis of material by ambient ionisation ion sources including rapid evaporative ionisation mass spectrometry ("REIMS") ion sources and the analysis of material by desorption electrospray ionisation ("DESI") mass spectrometry. Various embodiments relate to the use of mass spectrometers in diagnostic methods. Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

BACKGROUND

The mucosal membrane is a protective layer responsible for trapping pathogens in the human body. The mucosal membrane is an easily accessible and highly clinically relevant sample to diagnose pathogenic and cancerous associated diseases.

It is known to use medical swabs as a standard collection device for mucosal membranes.

Conventionally, the swab is placed into a sterile tube containing a buffer solution for storage and then the tube is sent to a laboratory for analysis. A laboratory receiving the tube will wipe the smear content across a culture medium such as an agar plate. The culture medium is then incubated to allow organisms present on the swab to grow.

Microbial identification may then be performed, e.g., under a microscope. Any organisms present in the sample may also be identified by 16S gene-sequencing and/or by using matrix-assisted laser desorption ionisation ("MALDI") mass spectrometry and then comparing the mass spectra with a commercial available database.

Although easy to handle, the current approach to the analysis of medical swabs for diagnostic purposes is culture-dependent and involves a time consuming and costly workflow. Diagnosis of diseases, such as infections or dysbiosis, and appropriate treatment is therefore associated with considerable delay. Furthermore, around 95% of bacteria cannot be cultured for analysis.

It is therefore desired to provide an improved method for mucosal analysis, e.g., diagnosis.

SUMMARY

According to an aspect there is provided a method comprising:
providing a sample on a swab;
directing a spray of electrically charged droplets onto a surface of the swab in order to generate a plurality of analyte ions; and
analysing the analyte ions.

Desorption electrospray ionisation ("DESI") is an ambient ionisation method that involves directing a spray of (primary) electrically charged droplets onto a surface. The electrospray mist is pneumatically directed at the sample where subsequent splashed (secondary) droplets carry desorbed ionised analytes. After ionisation, the resulting ions travel through air and pass into an atmospheric pressure interface of a mass spectrometer. Desorption electrospray ionisation ("DESI") is a technique that allows for ambient ionisation of a trace sample at atmospheric pressure with no sample preparation being required.

A "swab" in accordance with various embodiments is intended to be understood as comprising a "standard medical swab" i.e. a swab that is designed for sampling biological samples such as mucosal membranes. For example, the term "standard medical swab" should be understood as covering a "cotton bud" (British) or a "cotton swab" (American) i.e. a small wad of cotton wrapped around one or both ends of a tube. The tube may be made from plastic, rolled paper or wood.

StableFlex® fibre cores are known and comprise a 80 μm fused silica core coated with a polymer. Such fibre cores are not intended to be considered as comprising a "swab" within the meaning of the present application as materials having a fibre core are not considered to comprise a "standard medical swab".

In particular, the terms "swab", "medical swab" and "standard medical swab" as used within the present application are intended to exclude materials having a fused silica core.

It is known to directly analyse Solid Phase Micro Extraction ("SPME") fibres using desorption electrospray ionisation ("DESI") mass spectrometry. In this technique, a SPME fibre is exposed to the head space within a vial containing a sample. Alternatively, a SPME fibre may be dipped into a sample in solution. According to the known technique, analyte may be extracted into a SPME fibre coating in the liquid or gas phase, i.e. such that the sample does not remain in its native state. According to the known technique, the SPME fibre is then subjected to direct desorption electrospray ionisation ("DESI") mass spectrometry analysis by positioning the fibre in the spray of a desorption electrospray ionisation ("DESI") mass spectrometry arrangement.

Accordingly, this known technique requires (at least) a two-step sample preparation procedure comprising: (i) the acquisition or preparation of the sample, followed by (ii) the extraction of analyte into the SPME fibre. Moreover, the known specialist SPME fibres are not suited for the direct sampling of biological material, e.g. from a patient, such as the direct sampling of the mucosal membrane.

In contrast, various embodiments are based at least in part upon the recognition that a sample provided on a swab, e.g. a standard medical swab, may be directly analysed by desorption electrospray ionisation ("DESI") mass spectrometry. In particular, an important aspect of various embodiments is that a standard medical swab may itself be positioned in the spray of a desorption electrospray ionisation ("DESI") ionisation source.

Various embodiments are beneficial in that they require no sample preparation steps beyond the acquisition of the sample onto the swab.

Accordingly, various embodiments provide a rapid direct analysis method for samples provided on medical swabs.

Various embodiments are particularly suited to and useful in the analysis of biological material, e.g. from a patient, such as material sampled directly onto a swab from the mucosal membrane.

Furthermore, the use of medical swabs in desorption electrospray ionisation ("DESI") mass spectrometry analysis according to various embodiments opens up the possibility of performing multiple different analyses of the same sample. For example, multiple different analyses can be performed on the same swab. Such an approach beneficially provides multiple sets of information or data related to the same sample in a particularly convenient and efficient manner.

This ability to perform multiple different analyses on the same swab is due to the fact that desorption electrospray ionisation ("DESI") mass spectrometry analysis is a relatively non-destructive analysis technique. Furthermore, other commercial analysis techniques, such as culturing techniques and 16S rRNA sequencing techniques are optimised to use samples provided on (standard) medical swabs.

Accordingly, following a single sample acquisition onto a swab, the sample on the swab may be analysed multiple times using multiple different analysis techniques.

It will be appreciated, therefore, that various embodiments provide improved methods for analysis, e.g., diagnosis.

The terms "biological sample", "biological material" and the like are used interchangeably herein unless otherwise specified and they may optionally comprise or consist of biological tissue. The biological material etc. may optionally be selected, for example, from a surgical resection specimen, a biopsy specimen, a tissue specimen, a cell specimen, a smear, a body fluid specimen and/or a faecal specimen, any of which may be sampled in vivo from the subject, e.g., directly sampled onto a swab or taken as a biopsy, or be sampled ex vivo or in vitro, e.g., a sample may be provided and then sampled onto a swab, which may be referred to as indirect sampling onto a swab, or sampled with a biopsy needle, which may be referred to as indirect sampling with a biopsy needle. Optionally, the method is carried out on a provided biological sample, e.g., a provided biopsy, or a provided swab, i.e. a swab onto which a biological material was previously sampled.

A body fluid specimen may, for example, optionally be selected from blood, plasma, serum, sputum, lavage fluid, pus, urine, saliva, phlegm, vomit, faeces, amniotic fluid, cerebrospinal fluid, pleural fluid, semen, sputum, vaginal secretion, interstitial fluid, and/or lymph.

The swab may comprise a medical swab or a standard medical swab.

The swab may comprise a disposable swab.

The swab may comprise a cotton, rayon, plastic or foam swab.

The swab may comprise a hollow rod.

The swab may comprise plastic, wood or rolled paper.

The swab may comprise a swab arranged and adapted to sample a mucosal membrane.

The swab may have been chemically modified to enhance selectivity for an analyte.

The chemical modification may render the swab lipophilic.

The chemical modification may involve formation of a coating on a surface of the swab.

The coating may be a polymeric coating.

The polymer coating may comprise polydivinylbenzene (DVB), a copolymer of N-vinylpyrrolidone and divinylbenzene, or polydimethylsiloxane.

The chemical modification may utilise a solid-phase extraction material.

The polymeric coating may contain particles of a solid-phase extraction material.

The solid-phase extraction material may comprise polymer particles, silica particles, hybrid silica/organic particles, carbon particles or polymer-coated solid particles.

The polymer-coated solid particle may be a silica particle.

The polymer-coated solid particles may comprise polydivinylbenzene (DVB), a copolymer of N-vinylpyrrolidone and divinylbenzene, or polydimethylsiloxane.

The silica particles may be surface modified by reaction with a surface modifier having the formula:

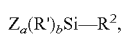

wherein Z=Cl, Br, I, $C_1$-$C_5$ alkoxy, dialkylamino or trifluoromethanesulfonate; a and b are each an integer from 0 to 3 provided that a+b=3; $R^1$ is a $C_1$-$C_6$ straight, cyclic or branched alkyl group, and $R^2$ is a functionalizing group.

R' may be selected from the group consisting of methyl, ethyl, propyl, isopropyl, butyl, t-butyl, sec-butyl, pentyl, isopentyl, hexyl and cyclohexyl.

$R^2$ may include an alkyl, alkaryl, alkenyl, alkynyl, aryl, cyano, amino, diol, nitro, ester, a cation exchange group, an anion exchange group, an alkyl or aryl group containing an embedded polar functionality or chiral moieties.

$R^2$ may be $C_1$-$C_{30}$ alkyl, alkaryl, cyanoalkyl, a diol; alkylamino, amino alkyl or carbamate group.

The silica particles may be surface modified by reaction with a compound selected from the group consisting of octyltrichlorosilane, octadecyltrichlorosilane, octyldimethylchlorosilane and octadecyldimethylchlorosilane.

The polymer particles may comprise polydivinylbenzene or a copolymer of N-vinylpyrrolidone and divinylbenzene.

The solid-phase extraction material may be an ion exchange resin.

The polymer particles may be ion exchange resin particles.

The ion exchange resin may comprise a copolymer of N-vinylpyrrolidone and divinylbenzene in which at least some of the benzene rings are sulfonated or carboxylated.

The ion exchange resin may comprise a copolymer of N-vinylpyrrolidone and divinylbenzene in which at least some of the benzene rings are substituted by imidazolium, —CH$_2$-piperazine groups or quaternary ammonium groups.

The quaternary ammonium group may be —CH$_2$N$^+$(CH$_3$)$_2$(C$_4$H$_9$).

The solid-phase extraction material or solid particle may be attached to the swab using an adhesive.

The sample may comprise biological tissue, biological matter, a bacterial colony, a fungal colony, and/or microbes.

The sample may be provided on the swab in its native or unmodified state.

The sample may comprise: (i) mammalian cells; (ii) microbes; (iii) extracellular or exogenous compounds; and/or (iv) a biomarker of (i), (ii) and/or (iii).

The biomarker may be selected from fatty acids, glycerolipids, sterol lipids, sphingolipids, prenol lipids, saccharolipids, and/or phospholipids, and/or a fingerprint of one or more thereof.

Providing the sample on the swab may comprise wiping the swab across an in vivo, in vitro or ex vivo biological sample or more generally a target. According to an embodiment the target may comprise an organic sample including a plastic. The target may comprise one or more bacterial colonies or one or more fungal colonies.

Providing the sample on the swab may comprise using the swab to sample a mucosal membrane.

The mucosal membrane may comprise a vaginal, nasal or oral mucosal membrane.

Directing the spray of charged droplets onto the swab may comprise directing a spray of charged solvent droplets onto the swab.

Directing the spray of charged droplets onto the swab may comprise directing the spray of charged droplets onto the swab at about atmospheric pressure.

Directing the spray of charged droplets onto the swab may comprise ionising the sample using Desorption Electrospray Ionisation ("DESI") or desorption electroflow focusing ionisation ("DEFFI").

The method may comprise directing the spray of charged droplets onto the swab from a sprayer.

The sprayer may be arranged at a distance from the swab in the range (i) <0.5 mm; (ii) about 0.5-1 mm; (iii) about 1-1.5 mm; (iv) about 1.5-2 mm; (v) about 2-3 mm; (vi) about 3-4 mm; or (vii) >4 mm.

The method may comprise providing the sprayer with a voltage in the range (i) <1 kV; (ii) about 1-2 kV; (iii) about 2-3 kV; (iv) about 3-4 kV; (v) about 4-5 kV; (vi) about 5-6 kV; (vii) about 6-7 kV; (viii) about 7-8 kV; (ix) about 8-9 kV; (x) about 9-10 kV; or (xi) >10 kV.

The method may comprise providing the sprayer with a solvent at a flow rate in the range (i) <5 μL/min; (ii) about 5-7 μL/min; (iii) about 7-9 μL/min; (iv) about 9-10 μL/min; (v) about 10-11 μL/min; (vi) about 11-13 μL/min; (vii) about 13-15 μL/min; (viii) about 15-20 μL/min; or (ix) >20 μL/min.

The method may comprise providing the sprayer with a gas at a pressure in the range (i) <5 bar; (ii) about 5-6 bar; (iii) about 6-7 bar; (iv) about 7-8 bar; (v) about 8-9 bar; (vi) about 9-10 bar; (vii) about 10-15 bar; or (viii) >15 bar.

The gas may comprise air or nitrogen.

The method may comprise rotating the swab whilst directing the spray of charged droplets onto the surface of the swab.

The step of rotating the swab whilst directing the spray of charged droplets onto the surface of the swab may comprise substantially continuously rotating the swab whilst directing the spray of charged droplets onto the surface of the swab.

The method may comprise translating and/or oscillating the swab whilst directing the spray of charged droplets onto the surface of the swab.

The step of translating and/or oscillating the swab may comprise substantially continuously translating and/or oscillating the swab whilst directing the spray of charged droplets onto the surface of the swab.

The method may comprise translating and/or oscillating the swab substantially in the direction of the axial length of the swab.

Analysing the analyte ions may comprise transferring the analyte ions to a mass and/or ion mobility spectrometer via a capillary or other inlet.

The entrance to the capillary or other inlet may be arranged at a distance from the swab in the range (i) <0.5 mm; (ii) about 0.5-1 mm; (iii) about 1-1.5 mm; (iv) about 1.5-2 mm; (v) about 2-3 mm; (vi) about 3-4 mm; or (vii) >4 mm.

Analysing the analyte ions may comprise mass analysing and/or ion mobility analysing the analyte ions or ions derived from the analyte ions to obtain mass spectrometric data and/or ion mobility data.

Various embodiments are contemplated wherein analyte ions generated by an ambient ionisation ion source are then subjected either to: (i) mass analysis by a mass analyser or filter such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser or filter such as a quadrupole mass analyser or a Time of Flight mass analyser (or vice versa). Various embodiments also relate to an ion mobility spectrometer and/or mass analyser and a method of ion mobility spectrometry and/or method of mass analysis.

Analysing the analyte ions may comprise determining the ion mobility, collision cross section or interaction cross section of the analyte ions or ions derived from the analyte ions to obtain mass spectrometric data and/or ion mobility data.

The method may comprise analysing the mass spectrometric data and/or ion mobility data in order either: (i) to distinguish between healthy and diseased states; (ii) to distinguish between potentially cancerous and non-cancerous states; (iii) to distinguish between different types or grades of cancer; (iv) to distinguish between different types or classes of sample; (v) to determine whether or not one or more desired or undesired substances are present in the sample; (vi) to confirm the identity or authenticity of the sample; (vii) to determine whether or not one or more impurities, illegal substances or undesired substances are present in the sample; (viii) to determine whether a human or animal patient is at an increased risk of suffering an adverse outcome; (ix) to make or assist in the making a diagnosis or prognosis; (x) to inform a surgeon, nurse, medic or robot of a medical, surgical or diagnostic outcome; and/or (xi) to identify and/or predict one or more diseases or clinical disorders.

The one or more diseases or clinical disorders may comprise (i) an infection; (ii) a change in the microbiome; (iii) pre-term delivery in pregnancy; (iv) an immunological disorder; (v) asthma; (vi) an allergy; (vii) inflammation; (viii) cancer; (ix) necrosis; and/or (x) a pre-cancerous state.

The method may comprise determining whether cancerous biological tissue or the tumour comprises either: (i) grade I, grade II, grade III or grade IV cancerous tissue; (ii) metastatic cancerous tissue; (iii) mixed grade cancerous tissue; or (iv) a sub-grade cancerous tissue.

The step of analysing the mass spectrometric data may comprise performing a supervised and/or unsupervised analysis of the mass spectrometric data.

The step of analysing the mass spectrometric data and/or ion mobility data may comprise using one or more of: univariate analysis; multivariate analysis; principal component analysis (PCA); linear discriminant analysis (LDA); maximum margin criteria (MMC); library-based analysis; soft independent modelling of class analogy (SIMCA); factor analysis (FA); recursive partitioning (decision trees); random forests; independent component analysis (ICA); partial least squares discriminant analysis (PLS-DA); orthogonal (partial least squares) projections to latent structures (OPLS); OPLS discriminant analysis (OPLS-DA); support vector machines (SVM); (artificial) neural networks; multilayer perceptron; radial basis function (RBF) networks; Bayesian analysis; cluster analysis; a kernelized method; and subspace discriminant analysis.

The method may comprise analysing the sample on the swab using one or more further different analysis methods.

The one or more further different analysis methods may comprise a culturing analysis method.

The culturing analysis method may comprise wiping the swab across a culturing medium, incubating the culturing medium, and examining the culturing medium under a microscope.

The one or more further different analysis methods may comprise a gene sequencing method.

The gene sequencing method may comprise a 16S rRNA gene sequencing method.

The one or more further different analysis methods may comprise a Matrix-Assisted Laser Desorption Ionisation ("MALDI") method.

The one or more further different analysis methods may comprise an ambient ionisation mass spectrometry method.

The one or more further different analysis methods may comprise a Rapid Evaporative Ionisation Mass Spectrometry ("REIMS") method.

According to an aspect there is provided apparatus comprising:

a first device arranged and adapted to direct a spray of charged droplets onto a surface of a swab in order to generate a plurality of analyte ions; and a second device arranged and adapted to analyse the analyte ions.

The first device may be arranged and adapted to direct a spray of charged solvent droplets onto the swab.

The first device may be arranged and to direct the spray of charged droplets onto the swab at about atmospheric pressure.

The first device may comprise a Desorption Electrospray Ionisation ("DESI") ion source or a desorption electroflow focusing ionisation ("DEFFI") ion source.

The first device may comprise a sprayer arranged and adapted to direct the spray of charged droplets onto the swab.

The sprayer may be arranged at a distance from the swab in the range (i) <0.5 mm; (ii) about 0.5-1 mm; (iii) about 1-1.5 mm; (iv) about 1.5-2 mm; (v) about 2-3 mm; (vi) about 3-4 mm; or (vii) >4 mm.

The apparatus may comprise a device arranged and adapted to provide the sprayer with a voltage in the range (i) <1 kV; (ii) about 1-2 kV; (iii) about 2-3 kV; (iv) about 3-4 kV; (v) about 4-5 kV; (vi) about 5-6 kV; (vii) about 6-7 kV; (viii) about 7-8 kV; (ix) about 8-9 kV; (x) about 9-10 kV; or (xi) >10 kV.

The apparatus may comprise a device arranged and adapted to provide the sprayer with a solvent at a flow rate in the range (i) <5 µL/min; (ii) about 5-7 µL/min; (iii) about 7-9 µL/min; (iv) about 9-10 µL/min; (v) about 10-11 µL/min; (vi) about 11-13 µL/min; (vii) about 13-15 µL/min; (viii) about 15-20 µL/min; or (ix) >20 µL/min.

The apparatus may comprise a device arranged and adapted to provide the sprayer with a gas at a pressure in the range (i) <5 bar; (ii) about 5-6 bar; (iii) about 6-7 bar; (iv) about 7-8 bar; (v) about 8-9 bar; (vi) about 9-10 bar; (vii) about 10-15 bar; or (viii) >15 bar.

The gas may comprise air or nitrogen.

The apparatus may comprise a third device arranged and adapted to rotate the swab whilst the spray of charged droplets is directed onto the surface of the swab.

The third device may be arranged and adapted to substantially continuously rotate the swab whilst the spray of charged droplets is directed onto the surface of the swab.

The apparatus may comprise a fourth device arranged and adapted to translate and/or oscillate the swab whilst the spray of charged droplets is directed onto the surface of the swab.

The fourth device may be arranged and adapted to substantially continuously translate and/or oscillate the swab whilst directing the spray of charged droplets onto the surface of the swab.

The fourth device may be arranged and adapted to translate and/or oscillate the swab substantially in the direction of the axial length of the swab.

The apparatus may comprise a capillary or other inlet arranged and adapted to transfer the analyte ions to the second device.

The entrance to the capillary or other inlet may be arranged at a distance from the swab in the range (i) <0.5 mm; (ii) about 0.5-1 mm; (iii) about 1-1.5 mm; (iv) about 1.5-2 mm; (v) about 2-3 mm; (vi) about 3-4 mm; or (vii) >4 mm.

The second device may comprise a mass analyser or filter and/or ion mobility analyser arranged and adapted to mass analyse and/or ion mobility analyse the analyte ions or ions derived from the analyte ions.

The second device may comprise an ion mobility device arranged and adapted to determine the ion mobility, collision cross section or interaction cross section of the analyte ions or ions derived from the analyte ions.

According to an aspect there is provided a medical swab for use in a method as described above, wherein the swab has been chemically modified to enhance selectivity for an analyte.

The swab may be a disposable swab.

The swab may be a cotton, rayon, plastic or foam swab.

The chemical modification may render the swab lipophilic.

The chemical modification may involve formation of a coating on a surface of the swab.

The coating may be a polymeric coating.

The polymer coating may comprise polydivinylbenzene (DVB), a copolymer of N-vinylpyrrolidone and divinylbenzene, or polydimethylsiloxane.

The chemical modification may utilise a solid-phase extraction material.

The polymeric coating may contain particles of a solid-phase extraction material.

The solid-phase extraction material may comprise polymer particles, silica particles, hybrid silica/organic particles, carbon particles or polymer-coated solid particles.

The polymer-coated solid particle may be a silica particle.

The polymer-coated solid particles may comprise polydivinylbenzene (DVB), a copolymer of N-vinylpyrrolidone and divinylbenzene, or polydimethylsiloxane.

The silica particles may be surface modified by reaction with a surface modifier having the formula:

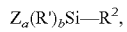

$$Z_a(R')_b Si-R^2,$$

wherein Z=Cl, Br, I, $C_1$-$C_5$ alkoxy, dialkylamino or trifluoromethanesulfonate; a and b are each an integer from 0 to 3 provided that a+b=3; $R^1$ is a $C_1$-$C_6$ straight, cyclic or branched alkyl group, and $R^2$ is a functionalizing group.

R' may be selected from the group consisting of methyl, ethyl, propyl, isopropyl, butyl, t-butyl, sec-butyl, pentyl, isopentyl, hexyl and cyclohexyl.

$R^2$ may include an alkyl, alkaryl, alkenyl, alkynyl, aryl, cyano, amino, dial, nitro, ester, a cation exchange group, an anion exchange group, an alkyl or aryl group containing an embedded polar functionality or chiral moieties.

$R^2$ may be $C_1$-$C_{30}$ alkyl, alkaryl, cyanoalkyl, a diol; alkylamino, amino alkyl or carbamate group.

The silica particles may be surface modified by reaction with a compound selected from the group consisting of octyltrichlorosilane, octadecyltrichlorosilane, octyldimethylchlorosilane and octadecyldimethylchlorosilane.

The polymer particles may comprise polydivinylbenzene or a copolymer of N-vinylpyrrolidone and divinylbenzene.

The solid-phase extraction material may be an ion exchange resin.

The polymer particles may be ion exchange resin particles.

The ion exchange resin may comprise a copolymer of N-vinylpyrrolidone and divinylbenzene in which at least some of the benzene rings are sulfonated or carboxylated.

The ion exchange resin may comprise a copolymer of N-vinylpyrrolidone and divinylbenzene in which at least some of the benzene rings are substituted by imidazolium, —$CH_2$-piperazine groups or quaternary ammonium groups.

The quaternary ammonium group may be —$CH_2N^+(CH_3)_2(C_4H_9)$.

The solid-phase extraction material or solid particle may be attached to the swab using an adhesive.

According to an aspect there is provided a method of chemically modifying a medical swab which comprises attaching particles of a solid-phase extraction material to the surface of the swab.

The attachment may utilise an adhesive.

According to an aspect there is provided a method of chemically modifying a medical swab comprising:

(a) forming a dispersion or solution of a chemical modifier;

(b) dipping the swab into the solution or dispersion;

(c) removing the swab from the solution or dispersion and drying it.

Steps (b) and (c) may be repeated at least once.

According to an aspect, there is provided a diagnostic method comprising: providing a sample on a swab wherein the swab further may comprise a solid-phase extraction ("SPE") substance for extracting analyte from a liquid sample;

directing a spray of electrically charged droplets onto a surface of the swab in order to generate a plurality of analyte ions; and mass analysing the analyte ions.

The solid-phase extraction substance may comprise a polymer.

The solid-phase extraction substance may be hydrophilic.

The solid-phase extraction substance may comprise a reversed-phase polymer.

The solid-phase extraction substance may comprise a cation-exchange or anion-exchange polymer.

The solid-phase extraction substance may comprise octadecylsilane ("ODS/C18") or polydimethylsiloxane ("PDMS").

The solid-phase extraction substance may comprise: (i) Oasis MAX® (mixed-mode cation exchange); (ii) hydrophilic N-vinylpyrrolidone and lipophilic divinylbenzene or Oasis HLB® (hydrophilic-lipophilic-balanced); or (iii) Oasis MCX® (mixed-mode cation exchange).

The method may further comprise rotating the swab whilst directing the spray of electrically charged droplets onto the surface of the swab.

The step of rotating the swab whilst directing the spray of electrically charged droplets onto the surface of the swab further may comprise substantially continuously rotating the swab whilst directing the spray of electrically charged droplets onto the surface of the swab.

The swab may comprise cotton, rayon or polyester.

The swab may comprise fibres which do not have a fused silica core.

According to an aspect there is provided a diagnostic method comprising:

providing a sample on a swab wherein the swab further may comprise a solid-phase extraction ("SPE") substance for extracting analyte from a liquid sample;

rotating the swab and at substantially the same time directing a spray of electrically charged droplets onto a surface of the swab in order to generate a plurality of analyte ions; and mass analysing and/or ion mobility analysing the analyte ions.

According to an aspect there is provided a method of Desorption Electrospray Ionisation ("DESI") comprising a diagnostic method as described above.

According to an aspect there is provided a method of mass spectrometry and/or method of ion mobility analysis comprising a method as described above.

According to an aspect there is provided apparatus comprising:

a device for directing a spray of electrically charged droplets onto a surface of a swab in order to generate a plurality of analyte ions, wherein the swab further may comprise a solid-phase extraction ("SPE") substance for extracting analyte from a liquid sample; and a mass analyser or filter and/or ion mobility analyser for mass analysing and/or ion mobility analysing the analyte ions.

According to an aspect there is provided apparatus comprising:

a first device for directing a spray of electrically charged droplets onto a surface of a swab in order to generate a plurality of analyte ions, wherein the swab further may comprise a solid-phase extraction ("SPE") substance for extracting analyte from a liquid sample;

a second device for rotating the swab at substantially the same time as the first device directs the spray of electrically charged droplets onto the surface of the swab; and a mass analyser or filter and/or ion mobility analyser for mass analysing and/or ion mobility analysing the analyte ions.

According to an aspect there is provided a mass and/or ion mobility analyser comprising apparatus as described above.

According to an aspect there is provided a method comprising:

providing a sample on a swab;
wetting the swab with a first liquid;
contacting the wetted swab with an electrode in order to generate an aerosol, smoke or vapour;
generating a plurality of analyte ions from the aerosol, smoke or vapour; and
analysing the analyte ions.

According to an aspect there is provided a diagnostic method comprising:

providing a sample on a swab;
wetting the swab with a first liquid;
contacting the wetted swab with a bipolar electrode in order to generate an aerosol;
generating a plurality of analyte ions from the aerosol; and
mass analysing and/or ion mobility analysing the analyte ions.

The first liquid may comprise water.

According to an aspect there is provided a method of Rapid Evaporative Ionisation Mass Spectrometry ("REIMS") comprising a method as described above.

According to an aspect there is provided apparatus comprising:

an electrode which is arranged and adapted to contact a sample on a swab which has been wetted with a first liquid so as to generate an aerosol, smoke or vapour;
a device which is arranged and adapted to generate a plurality of analyte ions from the aerosol, smoke or vapour; and
an analyser for analysing the analyte ions.

According to an aspect there is provided apparatus comprising:

a bipolar electrode which is arranged and adapted to contact a sample on a swab which has been wetted with a first liquid so as to generate an aerosol;
a device which is arranged and adapted to generate a plurality of analyte ions from the aerosol; and
a mass analyser or filter and/or ion mobility analyser for mass analysing and/or ion mobility analysing the analyte ions.

According to an aspect there is provided a mass and/or ion mobility spectrometer comprising apparatus as described above.

According to an aspect there is provided a swab comprising a solid-phase extraction ("SPE") substance for extracting analyte from a liquid sample, wherein the swab comprises fibres which do not have a fused silica core.

The swab may comprise cotton, rayon or polyester.

The solid-phase extraction substance may be hydrophilic.

The solid-phase extraction substance may comprise a reversed-phase polymer.

The solid-phase extraction substance may comprise a cation-exchange or anion-exchange polymer.

The solid-phase extraction substance may comprise octadecylsilane ("ODS/C18") or polydimethylsiloxane ("PDMS").

The solid-phase extraction substance may comprise: (i) Oasis MAX® (mixed-mode cation exchange); (ii) hydrophilic N-vinylpyrrolidone and lipophilic divinylbenzene or Oasis HLB® (hydrophilic-lipophilic-balanced); or (iii) Oasis MCX® (mixed-mode cation exchange).

According to an aspect there is provided a method comprising:

providing a sample on a swab;
rotating the swab and at substantially the same time directing a spray of charged droplets onto a surface of the swab in order to generate a plurality of analyte ions; and
analysing the analyte ions.

The step of rotating the swab whilst directing the spray of charged droplets onto the surface of the swab further may comprise substantially continuously rotating the swab whilst directing the spray of charged droplets onto the surface of the swab.

The method may comprise translating and/or oscillating the swab whilst directing the spray of charged droplets onto the surface of the swab.

According to an aspect there is provided a method comprising:

providing a sample on a swab;
translating and/or oscillating the swab and at substantially the same time directing a spray of charged droplets onto a surface of the swab in order to generate a plurality of analyte ions; and
analysing the analyte ions.

The method may comprise substantially continuously translating and/or oscillating the swab whilst directing the spray of charged droplets onto the surface of the swab.

The method may comprise translating and/or oscillating the swab substantially in the direction of the axial length of the swab.

According to an aspect there is provided apparatus comprising:

a first device arranged and adapted to direct a spray of charged droplets onto a surface of a swab in order to generate a plurality of analyte ions;
a second device arranged and adapted to rotate the swab at substantially the same time as the first device directs the spray of charged droplets onto the surface of the swab; and
an analyser arranged and adapted to analyse the analyte ions.

The second device may be arranged and adapted to substantially continuously rotate the swab whilst the first device directs the spray of charged droplets onto the surface of the swab.

The apparatus may comprise a third device arranged and adapted to translate and/or oscillate the swab whilst the first device directs the spray of charged droplets onto the surface of the swab.

According to an aspect there is provided apparatus comprising:

a first device arranged and adapted to direct a spray of charged droplets onto a surface of a swab in order to generate a plurality of analyte ions;
a third device arranged and adapted to translate and/or oscillate the swab whilst the first device directs the spray of charged droplets onto the surface of the swab; and
an analyser arranged and adapted to analyse the analyte ions.

The third device may be arranged and adapted to substantially continuously translate and/or oscillate the swab whilst the first device directs the spray of charged droplets onto the surface of the swab.

The third device may be arranged and adapted to translate and/or oscillate the swab substantially in the direction of the axial length of the swab.

According to an aspect there is provided a method comprising:

providing a sample on a swab;
analysing the sample on the swab using a first analysis method; and analysing the sample on the swab using one or more second different analysis methods;

wherein the first analysis method may comprise directing a spray of charged droplets onto a surface of the swab in order to generate a plurality of analyte ions and then analysing the analyte ions.

Directing the spray of charged droplets onto the swab may comprise directing a spray of charged solvent droplets onto the swab.

Directing the spray of charged droplets onto the swab may comprise directing the spray of charged droplets onto the swab at about atmospheric pressure.

Directing the spray of charged droplets onto the swab may comprise ionising the sample using desorption electrospray ionisation ("DESI") or desorption electroflow focusing ionisation ("DEFFI").

The one or more second analysis methods may comprise a culturing analysis method.

The culturing analysis method may comprise contacting the swab with a culturing medium, incubating the culturing medium, and examining the culturing medium or a sample thereof under a microscope.

The one or more second analysis methods may comprise a gene sequencing method.

The sequencing method may comprise a 16S rRNA gene sequencing method.

The one or more second analysis methods may comprise a Matrix-Assisted Laser Desorption Ionisation ("MALDI") method.

The one or more second analysis methods may comprise an ambient ionisation mass spectrometry method.

The ambient ionisation mass spectrometry method may be selected from the group consisting of: (i) a rapid evaporative ionisation mass spectrometry ("REIMS") method; (ii) a laser desorption ionisation ("LDI") method; (iii) a thermal desorption ionisation method; (iv) a laser diode thermal desorption ("LDTD") ionisation method; (v) a desorption electro-flow focusing ionisation ("DEFFI") method; (vi) a dielectric barrier discharge ("DBD") plasma ionisation method; (vii) an Atmospheric Solids Analysis Probe ("ASAP") ionisation method; (viii) an ultrasonic assisted spray ionisation method; (ix) an easy ambient sonic-spray ionisation ("EASI") method; (x) a desorption atmospheric pressure photoionisation ("DAPPI") method; (xi) a paper-spray ("PS") ionisation method; (xii) a jet desorption ionisation ("JeDI") method; (xiii) a touch spray ("TS") ionisation method; (xiv) a nano-DESI ionisation method; (xv) a laser ablation electrospray ("LAESI") ionisation method; (xvi) a direct analysis in real time ("DART") ionisation method; (xvii) a probe electrospray ionisation ("PESI") method; (xviii) a solid-probe assisted electrospray ionisation ("SPA-ESI") method; (xix) a cavitron ultrasonic surgical aspirator ("CUSA") method; (xx) a focussed or unfocussed ultrasonic ablation method; (xxi) a microwave resonance method; and (xxii) a pulsed plasma RF dissection method.

The method may comprise analysing the sample on the swab using a third different analysis method.

According to an aspect there is provided a method comprising:

providing a sample on a swab;

analysing the sample on the swab in a first mode of operation, wherein the first mode of operation may comprise directing a spray of charged droplets onto a surface of the swab in order to generate a plurality of analyte ions; and determining whether the analyte ions may comprise one or more ions of interest;

wherein if it is determined that the analyte ions comprise one or more ions of interest, then the method further may comprise:

analysing the sample on the swab in a second different mode of operation.

Directing the spray of charged droplets onto the swab may comprise directing a spray of charged solvent droplets onto the swab.

Directing the spray of charged droplets onto the swab may comprise directing the spray of charged droplets onto the swab at about atmospheric pressure.

Directing the spray of charged droplets onto the swab may comprise ionising the sample using desorption electrospray ionisation ("DESI") or desorption electroflow focusing ionisation ("DEFFI").

The second mode of operation may comprise directing a spray of charged droplets onto a surface of the swab in a second different mode of operation.

Either:

(i) the first mode of operation may comprise a positive ion mode of operation and the second mode of operation may comprise a negative ion mode of operation; or (ii) the first mode of operation may comprise a negative ion mode of operation and the second mode of operation may comprise a positive ion mode of operation.

The first mode of operation may comprise directing a spray of charged droplets onto a surface of the swab, wherein the charged droplets comprise a first solvent or solvent composition; and the second mode of operation may comprise directing a spray of charged droplets onto a surface of the swab, wherein the charged droplets comprise a second different solvent or solvent composition.

The second mode of operation may comprise an optimised version of the first mode of operation.

The second mode of operation may comprise generating a plurality of analyte ions from the sample using a second different ambient ionisation analysis method.

The second different ambient ionisation analysis method may be selected from the group consisting of: (i) a rapid evaporative ionisation mass spectrometry ("REIMS") method; (ii) a laser desorption ionisation ("LDI") method; (iii) a thermal desorption ionisation method; (iv) a laser diode thermal desorption ("LDTD") ionisation method; (v) a desorption electro-flow focusing ionisation ("DEFFI") method; (vi) a dielectric barrier discharge ("DBD") plasma ionisation method; (vii) an Atmospheric Solids Analysis Probe ("ASAP") ionisation method; (viii) an ultrasonic assisted spray ionisation method; (ix) an easy ambient sonic-spray ionisation ("EASI") method; (x) a desorption atmospheric pressure photoionisation ("DAPPI") method; (xi) a paperspray ("PS") ionisation method; (xii) a jet desorption ionisation ("JeDI") method; (xiii) a touch spray ("TS") ionisation method; (xiv) a nano-DESI ionisation method; (xv) a laser ablation electrospray ("LAESI") ionisation method; (xvi) a direct analysis in real time ("DART") ionisation method; (xvii) a probe electrospray ionisation ("PESI") method; (xviii) a solid-probe assisted electrospray ionisation ("SPA-ESI") method; (xix) a cavitron ultrasonic surgical aspirator ("CUSA") method; (xx) a focussed or unfocussed ultrasonic ablation method; (xxi) a microwave resonance method; and (xxii) a pulsed plasma RF dissection method.

The first mode of operation may comprise analysing the analyte ions using first operational parameters; and the second mode of operation may comprise analysing analyte ions from the sample using second different operational parameters.

The first and/or second mode of operation may comprise (i) a mode of operation wherein analyte ions or ions derived from the analyte ions are mass analysed and/or ion mobility analysed; (ii) a mode of operation wherein the ion mobility, collision cross section or interaction cross section of analyte ions or ions derived from the analyte ions may be determined; (iii) a mode of operation wherein analyte ions are further subjected to fragmentation; and/or (iv) a mode of operation wherein analyte ions are reacted, excited, fragmented or fractionally separated.

The second different mode of operation may comprise: (i) a culturing mode of operation; (ii) a gene sequencing mode of operation; or (iii) a Matrix-Assisted Laser Desorption Ionisation ("MALDI") mode of operation.

The method may comprise selecting and/or optimising the second mode of operation based on information acquired during the first mode of operation.

The method may comprise:
determining whether analyte ions analysed in the second mode of operation comprise one or more second ions of interest;
wherein if it is determined that the analyte ions comprise one or more second ions of interest, then the method further may comprise:
analysing the sample on the swab in a third different mode of operation.

According to an aspect there is provided apparatus comprising:
a first device arranged and adapted to analyse a sample on a swab in a first mode of operation, wherein the first mode of operation may comprise directing a spray of charged droplets onto a surface of the swab in order to generate a plurality of analyte ions; and
a second device arranged and adapted to determine whether the analyte ions comprise one or more ions of interest, and if it is determined that the analyte ions comprise one or more ions of interest, to cause a device to analyse the sample on the swab in a second different mode of operation.

The first device may be arranged and adapted to direct a spray of charged solvent droplets onto the swab.

The first device may be arranged and adapted to direct the spray of charged droplets onto the swab at about atmospheric pressure.

The first device may comprise a desorption electrospray ionisation ("DESI") device or a desorption electroflow focusing ionisation ("DEFFI") device.

The second device may be arranged and adapted to cause the first device to analyse the sample on the swab in a second different mode of operation.

Either:
(i) the first mode of operation may comprise a positive ion mode of operation and the second mode of operation may comprise a negative ion mode of operation; or
(ii) the first mode of operation may comprise a negative ion mode of operation and the second mode of operation may comprise a positive ion mode of operation.

In the first mode of operation the charged droplets may comprise a first solvent or solvent composition; and
in the second mode of operation the charged droplets may comprise a second different solvent or solvent composition.

The second mode of operation may comprise an optimised version of the first mode of operation.

The second device may be arranged and adapted to cause a second device to analyse the sample on the swab using a second different ambient ionisation analysis method.

The second device may be selected from the group consisting of: (i) a rapid evaporative ionisation mass spectrometry ("REIMS") ion source; (ii) a laser desorption ionisation ("LDI") ion source; (iii) a thermal desorption ionisation ion source; (iv) a laser diode thermal desorption ("LDTD") ion source; (v) a desorption electro-flow focusing ionisation ("DEFFI") ion source; (vi) a dielectric barrier discharge ("DBD") plasma ion source; (vii) an Atmospheric Solids Analysis Probe ("ASAP") ion source; (viii) an ultrasonic assisted spray ion source; (ix) an easy ambient sonic-spray ionisation ("EASI") ion source; (x) a desorption atmospheric pressure photoionisation ("DAPPI") ion source; (xi) a paperspray ("PS") ion source; (xii) a jet desorption ionisation ("JeDI") ion source; (xiii) a touch spray ("TS") ion source; (xiv) a nano-DESI ion source; (xv) a laser ablation electrospray ("LAESI") ion source; (xvi) a direct analysis in real time ("DART") ion source; (xvii) a probe electrospray ionisation ("PESI") ion source; (xviii) a solid-probe assisted electrospray ionisation ("SPA-ESI") ion source; (xix) a cavitron ultrasonic surgical aspirator ("CUSA") device; (xx) a focussed or unfocussed ultrasonic ablation device; (xxi) a microwave resonance device; and (xxii) a pulsed plasma RF dissection device.

The apparatus may be arranged and adapted in the first mode of operation to analyse the analyte ions using first operational parameters; and
the apparatus may be arranged and adapted in the second mode of operation to analyse analyte ions from the sample using second different operational parameters.

The apparatus may comprise: (i) a mass analyser or filter and/or ion mobility analyser for mass analysing and/or ion mobility analysing analyte ions or ions derived from the analyte ions in the first and/or second mode of operation; (ii) an ion mobility device for determining the ion mobility, collision cross section or interaction cross section of analyte ions or ions derived from the analyte ions in the first and/or second mode of operation; (iii) a fragmentation device for subjecting analyte ions to fragmentation in the first and/or second mode of operation; and/or (iv) one or more devices for reacting, exciting, fragmenting and/or fractionally separating analyte ions in the first and/or second mode of operation.

According to an aspect there is provided a method comprising:
automatically analysing a plurality of swabs by directing a spray of charged droplets onto a surface of each swab in order to generate a plurality of analyte ions; and
analysing the analyte ions from each swab.

A different sample may be provided on each of the plurality of swabs.

The step of automatically analysing the plurality of swabs may comprise automatically analysing the plurality of swabs substantially sequentially.

The step of automatically analysing the plurality of swabs may comprise automatically analysing two or more of the plurality of swabs substantially simultaneously or in parallel.

The method may comprise rotating, oscillating and/or translating each swab and at substantially the same time directing the spray of charged droplets onto a surface of each swab in order to generate the plurality of analyte ions.

According to an aspect there is provided apparatus comprising:

a first device arranged and adapted to automatically analyse a plurality of swabs by directing a spray of charged droplets onto a surface of each swab in order to generate a plurality of analyte ions; and a second device arranged and adapted to analyse the analyte ions from each swab.

A different sample may be provided on each of the plurality of swabs.

The first device may be arranged and adapted to automatically analyse the plurality of swabs substantially sequentially.

The first device may be arranged and adapted to automatically analyse two or more of the plurality of swabs substantially simultaneously or in parallel.

The apparatus may comprise a third device arranged and adapted to rotate, oscillate and/or translate each swab whilst the first device directs the spray of charged droplets onto the surface of each swab.

According to an aspect there is provided a method comprising:

transferring a plurality of samples onto different positions on a roll, sheet, tape or substrate;

using an ambient ion source to analyse a first sample on the roll, sheet, tape or substrate;

advancing the roll, sheet, tape or substrate; and using an ambient ion source to analyse a second sample on the roll, sheet, tape or substrate.

The method may comprise:

(i) advancing the roll, sheet, tape or substrate;

(ii) using an ambient ion source to analyse one or more further samples on the roll, sheet, tape or substrate; and (iii) optionally repeating steps (i) and (ii) one or more times.

The ambient ion source may comprise a desorption electrospray ionisation ("DESI") ion source or a desorption electroflow focusing ionisation ("DEFFI") ion source.

The method may comprise identifying the first sample and/or the second sample and/or the one or more further samples.

According to an aspect there is provided a method comprising:

directing a spray of charged droplets onto a surface of a swab having a sample of vaginal mucosa from a human or non-human animal provided thereon in order to generate a plurality of analyte ions;

analysing the analyte ions to obtain mass spectrometric data and/or ion mobility data; and determining from the mass spectrometric data and/or ion mobility data either: (i) whether or not the human or non-human animal is pregnant; (ii) the stage or state of pregnancy of the human or non-human animal; (iii) whether or not the human or non-human animal is at an increased risk of an adverse pregnancy outcome; and/or (iv) whether or not the human or non-human animal is at an increased risk of having a preterm delivery or a premature delivery.

The method may comprise identifying the presence of one or more microbes in the sample of vaginal mucosa, wherein the microbes are optionally bacteria.

The one or more microbes may be selected from the group consisting of: (i) *Candida albicans*; (ii) *Pseudomonas montelli*; (iii) *Staphylococcus epidermis*; (iv) *Moraxella catarrhalis*; (v) *Klebsiella pneumonia*; and (vi) *Lactobacillus* sp.

According to an aspect there is provided a method of pregnancy testing or pregnancy monitoring comprising a method as described above.

The method may comprise periodically repeating the method in order to monitor the development of the pregnancy of the human or non-human animal.

According to an aspect there is provided a method of diagnosis or prognosis comprising a method as described above.

According to an aspect there is provided a method comprising:

providing a faecal sample on an absorbent or other surface;

using an ambient ionisation source to generate a plurality of analyte ions from the faecal sample; and analysing the analyte ions.

The step of using an ambient ionisation source to generate the plurality of analyte ions may comprise directing a spray of charged droplets onto the absorbent or other surface.

The step of using an ambient ionisation source to generate the plurality of analyte ions may comprise generating aerosol, smoke or vapour from the faecal sample.

The method may comprise ionising the aerosol, smoke or vapour in order to generate the analyte ions.

The absorbent surface may comprise toilet tissue paper, tissue paper, a nappy or diaper or an incontinence pad or pant.

The method may comprise determining based on the analysis whether or not the faecal sample contains blood, human blood, non-human animal blood, haemoglobin, pathogens, undesired material, non-human material, parasite material or excreta or other waste products from parasites.

The method may comprise determining on the basis of whether or not the faecal sample is determined to contain blood, human blood, non-human animal blood or haemoglobin whether or not the human or non-human animal suffers from or has an anal fissure, diverticular disease, an inflammatory disease, angiodysplasia and/or a polyp in their colon, bowel or other part of their body or suffers from or has another medical disease or condition.

The method may comprise analysing the level and/or composition of bile present in the faecal sample.

The method may comprise determining from the analysis of the level and/or composition of bile present in the faecal sample whether or not the human or non-human animal suffers from or has a liver disease, kidney disease or other medical disease or condition.

The method may comprise analysing the composition of the gastrointestinal microbiome of the human or non-human animal.

The method may comprise determining or assessing the impact of antibiotics or probiotics upon the human or non-human animal based upon the analysis of the gastrointestinal microbiome, in the faecal sample of the human or non-human animal.

The method may comprise determining, based on the analysis, whether the faecal sample may comprise: (i) one or more particular microbes; (ii) one or more pathogens; (iii) one or more parasites; and/or (iv) one or more metabolites.

According to an aspect there is provided the use of a swab as described above in a method according as described above.

According to an aspect there is provided a method of desorption electrospray ionisation ("DESI") comprising a method as described above.

According to an aspect there is provided a method of mass spectrometry comprising a method as described above.

According to an aspect there is provided a desorption electrospray ionisation ("DESI") ion source comprising apparatus as described above.

According to an aspect there is provided a mass and/or ion mobility spectrometer comprising apparatus as described above.

According to an aspect there is provided a mass and/or ion mobility spectrometer comprising:

a first device arranged and adapted to accommodate a biopsy sample;

a second device arranged and adapted to generate analyte ions from a biopsy sample within the first device, wherein the second device may be arranged and adapted to generate first analyte ions from a first position on the biopsy sample at a first time, and to generate second analyte ions from a second different position on the biopsy sample at a second different time; and an analyser arranged and adapted to analyse the analyte ions.

The biopsy sample may comprise a sample of tissue having a longitudinal length.

The composition of the sample of tissue may vary or change along the longitudinal length.

The longitudinal length may correspond to the depth within a tissue.

The biopsy sample may comprise a biopsy core or cylinder.

The first device may comprise a channel arranged and adapted to accommodate a biopsy core.

The second device may be arranged and adapted to generate first analyte ions from a first position along the longitudinal length of the biopsy sample at the first time, and to generate second analyte ions from a second different position along the longitudinal length of the biopsy sample at the second different time.

The second device may be arranged and adapted to scan at least a portion of the longitudinal length of the biopsy sample so as to generate analyte ions from multiple positions along the longitudinal length of the biopsy sample.

The second device may comprise an ambient ionisation ion source.

The ambient ionisation ion source may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The second device may be arranged and adapted to generate aerosol, smoke or vapour from the biopsy sample, and to ionise the aerosol, smoke or vapour in order to generate the analyte ions.

The second device may comprise one or more electrodes arranged and adapted to contact the biopsy sample to generate the aerosol, smoke or vapour.

The one or more electrodes may comprise a bipolar device or a monopolar device.

The one or more electrodes may comprise either: (i) a monopolar device, wherein the apparatus optionally further comprises a separate return electrode; (ii) a bipolar device; or (iii) a multi-phase RF device, wherein the apparatus optionally further comprises a separate return electrode or electrodes.

The one or more electrodes may comprise a rapid evaporation ionisation mass spectrometry ("REIMS") device.

The mass and/or ion mobility spectrometer may comprise a device arranged and adapted to apply an AC or RF voltage to the one or more electrodes in order to generate the aerosol, smoke or vapour.

The device for applying the AC or RF voltage to the one or more electrodes may be arranged and adapted to apply one or more pulses of the AC or RF voltage to the one or more electrodes.

Application of the AC or RF voltage to the one or more electrodes may cause heat to be dissipated into the sample.

The second device may comprise a laser for irradiating the sample.

The second device may be arranged and adapted to generate aerosol, smoke or vapour from the sample by direct evaporation or vaporisation of sample material from the sample by Joule heating or diathermy.

The second device may be arranged and adapted to direct ultrasonic energy into the sample.

The second device may be arranged and adapted to direct a spray of charged droplets onto the biopsy sample so as to generate the analyte ions.

The ambient ionisation ion source may comprise a desorption electrospray ionisation ("DESI") ion source or a desorption electroflow focusing ionisation ("DEFFI") ion source.

The desorption electrospray ionisation ("DESI") ion source or desorption electroflow focusing ionisation ("DEFFI") ion source may comprise a gradient desorption electrospray ionisation ("DESI") ion source or a gradient desorption electroflow focusing ionisation ("DEFFI") ion source wherein the composition of a solvent supplied to and/or emitted from the desorption electrospray ionisation ("DESI") ion source or desorption electroflow focusing ionisation ("DEFFI") ion source is varied as a function of time.

The desorption electrospray ionisation ("DESI") ion source or desorption electroflow focusing ionisation ("DEFFI") ion source may be arranged and adapted to perform a gradient desorption electrospray ionisation analysis of the biopsy sample.

The desorption electrospray ionisation ("DESI") ion source or desorption electroflow focusing ionisation ("DEFFI") ion source may be arranged and adapted to perform a gradient desorption electrospray ionisation analysis along the length of the biopsy sample, wherein the composition of a solvent supplied to and/or emitted from the desorption electrospray ionisation ("DESI") ion source or desorption electroflow focusing ionisation ("DEFFI") ion source is varied as a function of position along the length of the biopsy sample.

The analyser may comprise: (i) a mass analyser or filter and/or ion mobility analyser for mass analysing and/or ion mobility analysing the analyte ions and/or ions derived from the analyte ions; (ii) an ion mobility device for determining the ion mobility, collision cross section or interaction cross section of the analyte ions and/or ions derived from the analyte ions; and/or (iii) one or more fragmentation, collision or reaction devices for fragmenting or reacting the analyte ions.

According to an aspect there is provided a method of mass spectrometry comprising:

providing a biopsy sample;

generating first analyte ions from a first position on the biopsy sample at a first time, and generating second analyte ions from a second different position on the biopsy sample at a second different time; and analysing the analyte ions.

The biopsy sample may comprise a sample of tissue having a longitudinal length.

The composition of the sample of tissue may vary or change along the longitudinal length.

The longitudinal length may correspond to the depth within a tissue.

The biopsy sample may comprise a biopsy core or cylinder.

The method may comprise accommodating the biopsy sample in a channel.

The method may comprise generating first analyte ions from a first position along the longitudinal length of the biopsy sample at the first time, and generating second analyte ions from a second different position along the longitudinal length of the biopsy sample at the second different time.

The method may comprise scanning at least a portion of the longitudinal length of the biopsy sample so as to generate analyte ions from multiple positions along the longitudinal length of the biopsy sample.

The method may comprise generating the analyte ions using an ambient ionisation ion source.

The ambient ionisation ion source may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The method may comprise generating aerosol, smoke or vapour from the biopsy sample, and ionising the aerosol, smoke or vapour in order to generate the analyte ions.

The method may comprise contacting the biopsy sample with one or more electrodes to generate the aerosol, smoke or vapour.

The one or more electrodes may comprise a bipolar device or a monopolar device.

The one or more electrodes may comprise either: (i) a monopolar device, wherein the apparatus optionally further comprises a separate return electrode; (ii) a bipolar device; or (iii) a multi-phase RF device, wherein the apparatus optionally further comprises a separate return electrode or electrodes.

The one or more electrodes may comprise a rapid evaporation ionisation mass spectrometry ("REIMS") device.

The method may comprise applying an AC or RF voltage to the one or more electrodes in order to generate the aerosol, smoke or vapour.

The step of applying the AC or RF voltage to the one or more electrodes may comprise applying one or more pulses of the AC or RF voltage to the one or more electrodes.

Applying the AC or RF voltage to the one or more electrodes may cause heat to be dissipated into the sample.

The method may comprise irradiating the sample with a laser in order to generate the analyte ions.

The method may comprise directing ultrasonic energy into the sample.

The method may comprise directing a spray of charged droplets onto the biopsy sample so as to generate the analyte ions.

The step of directing the spray of charged droplets onto the biopsy sample may comprise using a desorption electrospray ionisation ("DESI") ion source or a desorption electroflow focusing ionisation ("DEFFI") ion source to generate the analyte ions.

The method may comprise varying the composition of a solvent supplied to and/or emitted from the desorption electrospray ionisation ("DESI") ion source or desorption electroflow focusing ionisation ("DEFFI") ion source as a function of time.

The method may comprise performing a gradient desorption electrospray ionisation analysis of the biopsy sample.

The method may comprise varying the composition of a solvent supplied to and/or emitted from the desorption electrospray ionisation ("DESI") ion source or desorption electroflow focusing ionisation ("DEFFI") ion source as a function of position along the length of the biopsy sample.

The method may comprise: (i) mass analysing and/or ion mobility analysing the analyte ions and/or ions derived from the analyte ions; (ii) determining the ion mobility, collision cross section or interaction cross section of the analyte ions and/or ions derived from the analyte ions; and/or (iii) fragmenting or reacting the analyte ions.

The method may comprise analysing a disease.

The method may comprise determining the presence, location, margin and/or size of a tumour.

The method may comprise characterising a tumour based on: (i) the aggressive of the tumour; (ii) the susceptibility of the tumour to treatment; (iii) whether and/or how much of the tumour can be surgically removed; and/or (iv) whether and/or how much of the tumour can be removed based on the location of the tumour.

According to an aspect there is provided a method comprising:

sampling tissue using a biopsy needle so as to produce a first biopsy sample and a second biopsy sample;

analysing the first biopsy sample in a first mode of operation, wherein the first mode of operation may comprise generating analyte ions from the first biopsy sample and analysing the analyte ions; and analysing the second biopsy sample in a second different mode of operation.

The first mode of operation may comprise generating analyte ions from the first biopsy sample using a first ambient ionisation analysis method.

The first ambient ionisation analysis method may be selected from the group consisting of: (i) a rapid evaporative ionisation mass spectrometry ("REIMS") method; (ii) a desorption electrospray ionisation ("DESI") ionisation method; (iii) a laser desorption ionisation ("LDI") method; (iv) a thermal desorption ionisation method; (v) a laser diode thermal desorption ("LDTD") ionisation method; (vi) a desorption electro-flow focusing ionisation ("DEFFI") method; (vii) a dielectric barrier discharge ("DBD") plasma ionisation method; (viii) an Atmospheric Solids Analysis Probe ("ASAP") ionisation method; (ix) an ultrasonic assisted spray ionisation method; (x) an easy ambient sonic-spray ionisation ("EASI") method; (xi) a desorption atmospheric pressure photoionisation ("DAPPI") method; (xii) a paperspray ("PS") ionisation method; (xiii) a jet desorption ionisation ("JeDI") method; (xiv) a touch spray ("TS") ionisation method; (xv) a nano-DESI ionisation method; (xvi) a laser ablation electrospray ("LAESI") ionisation method; (xvii) a direct analysis in real time ("DART") ionisation method; (xviii) a probe electrospray ionisation ("PESI") method; (xix) a solid-probe assisted electrospray ionisation ("SPA-ESI") method; (xx) a cavitron ultrasonic surgical aspirator ("CUSA") method; (xxi) a focussed or unfocussed ultrasonic ablation method; (xxii) a microwave resonance method; and (xxiii) a pulsed plasma RF dissection method.

The step of generating analyte ions from the first biopsy sample may comprise directing a spray of charged droplets onto the first biopsy sample in order to generate the analyte ions.

Directing the spray of charged droplets onto the first biopsy sample may comprise directing a spray of charged solvent droplets onto the first biopsy sample.

Directing the spray of charged droplets onto the first biopsy sample may comprise directing the spray of charged droplets onto the first biopsy sample at about atmospheric pressure.

Directing the spray of charged droplets onto the first biopsy sample may comprise ionising the sample using desorption electrospray ionisation ("DESI") or desorption electroflow focusing ionisation ("DEFFI").

The step of generating analyte ions from the first biopsy sample may comprise generating aerosol, smoke or vapour from the first biopsy sample, and ionising the aerosol, smoke or vapour to generate the analyte ions.

The step of generating analyte ions from the first biopsy sample may comprise contacting one or more electrodes to the biopsy sample to generate the aerosol, smoke or vapour.

The one or more electrodes may comprise a bipolar device or a monopolar device.

The one or more electrodes may comprise either: (i) a monopolar device, wherein the apparatus optionally further comprises a separate return electrode; (ii) a bipolar device; or (iii) a multi-phase RF device, wherein the apparatus optionally further comprises a separate return electrode or electrodes.

The one or more electrodes may comprise a rapid evaporation ionisation mass spectrometry ("REIMS") device.

The method may comprise applying an AC or RF voltage to the one or more electrodes in order to generate the aerosol, smoke or vapour.

The step of applying the AC or RF voltage to the one or more electrodes may comprise applying one or more pulses of the AC or RF voltage to the one or more electrodes.

Applying the AC or RF voltage to the one or more electrodes may cause heat to be dissipated into the sample.

The step of generating analyte ions from the first biopsy sample may comprise directing a laser beam onto the first biopsy sample to generate the analyte ions.

The second mode of operation may comprise generating analyte ions from the second biopsy sample and analysing the analyte ions in a second different mode of operation.

The second mode of operation may comprise generating analyte ions from the second biopsy sample using the first ambient ionisation analysis method in a second different mode of operation.

Either:
(i) the first mode of operation may comprise a positive ion mode of operation and the second mode of operation may comprise a negative ion mode of operation; or
(ii) the first mode of operation may comprise a negative ion mode of operation and the second mode of operation may comprise a positive ion mode of operation.

The first mode of operation may comprise generating the analyte ions from the first biopsy sample using a first solvent or solvent composition; and the second mode of operation may comprise generating the analyte ions from the second biopsy sample using a second different solvent or solvent composition.

The second mode of operation may comprise an optimised version of the first mode of operation.

The second mode of operation may comprise generating a plurality of analyte ions from the second biopsy sample using a second different ambient ionisation analysis method.

The second different ambient ionisation analysis method may be selected from the group consisting of: (i) a rapid evaporative ionisation mass spectrometry ("REIMS") method; (ii) a desorption electrospray ionisation ("DESI") ionisation method; (iii) a laser desorption ionisation ("LDI") method; (iv) a thermal desorption ionisation method; (v) a laser diode thermal desorption ("LDTD") ionisation method; (vi) a desorption electro-flow focusing ionisation ("DEFFI") method; (vii) a dielectric barrier discharge ("DBD") plasma ionisation method; (viii) an Atmospheric Solids Analysis Probe ("ASAP") ionisation method; (ix) an ultrasonic assisted spray ionisation method; (x) an easy ambient sonic-spray ionisation ("EASI") method; (xi) a desorption atmospheric pressure photoionisation ("DAPPI") method; (xii) a paperspray ("PS") ionisation method; (xiii) a jet desorption ionisation ("JeDI") method; (xiv) a touch spray ("TS") ionisation method; (xv) a nano-DESI ionisation method; (xvi) a laser ablation electrospray ("LAESI") ionisation method; (xvii) a direct analysis in real time ("DART") ionisation method; (xviii) a probe electrospray ionisation ("PESI") method; (xix) a solid-probe assisted electrospray ionisation ("SPA-ESI") method; (xx) a cavitron ultrasonic surgical aspirator ("CUSA") method; (xxi) a focussed or unfocussed ultrasonic ablation method; (xxii) a microwave resonance method; and (xxiii) a pulsed plasma RF dissection method.

The first mode of operation may comprise analysing the analyte ions from the first biopsy sample using first operational parameters; and the second mode of operation may comprise analysing the analyte ions from the second biopsy sample using second different operational parameters.

The first and/or second mode of operation may comprise: (i) a mode of operation wherein analyte ions or ions derived from the analyte ions are mass analysed and/or ion mobility analysed; (ii) a mode of operation wherein the ion mobility, collision cross section or interaction cross section of analyte ions or ions derived from the analyte ions is determined; (iii) a mode of operation wherein analyte ions are subjected to fragmentation; and/or (iv) a mode of operation wherein analyte ions are reacted, excited, fragmented or fractionally separated.

The second different mode of operation may comprise: (i) a gene sequencing mode of operation; (ii) a Matrix-Assisted Laser Desorption Ionisation ("MALDI") mode of operation; and/or (iii) a histopathological mode of operation.

The method may comprise selecting and/or optimising the second mode of operation based on information acquired during the first mode of operation.

The first biopsy sample may comprise a first portion of the tissue having a first longitudinal length and/or the second biopsy sample may comprise a second portion of the tissue having a second longitudinal length.

The composition of the first biopsy sample may vary or change along the first longitudinal length and/or the composition of the second biopsy sample may vary or change along the second longitudinal length.

The first longitudinal length may correspond to the depth within the tissue and/or the second longitudinal length may correspond to the depth within the tissue.

The first biopsy sample may comprise a biopsy core or cylinder and/or the second biopsy sample may comprise a biopsy core or cylinder.

The first biopsy sample may comprise a first portion of the tissue and the second biopsy sample may comprise a second portion of the tissue; and the first portion of the tissue may have been adjacent and/or connected to the second portion of the tissue.

The first portion of the tissue may have been adjacent and/or connected to the second portion of the tissue along some, most or all the axial length of the first and/or second portion of the tissue.

Sampling tissue using the biopsy needle may comprise producing the first biopsy sample and the second biopsy sample substantially at the same time.

Sampling tissue using the biopsy needle may comprise inserting the biopsy needle into the tissue a single time so as to produce the first and second samples.

The biopsy needle may comprise a needle comprising a first hollow tube or cylinder and a second hollow tube or cylinder.

The first hollow tube or cylinder and second hollow tube or cylinder may be conjoined.

The first hollow tube or cylinder and second hollow tube or cylinder may be conjoined along some, most or all of an axial length of the first and/or an axial length of the second hollow tube or cylinder.

According to an aspect there is provided a biopsy needle arranged and adapted to produce a first biopsy sample and a second biopsy sample when sampling tissue.

The first biopsy sample may comprise a first portion of the tissue having a first longitudinal length and/or the second biopsy sample may comprise a second portion of the tissue having a second longitudinal length.

The composition of the first biopsy sample may vary or change along the first longitudinal length and/or the composition of the second biopsy sample may vary or change along the second longitudinal length.

The first longitudinal length may correspond to the depth within the tissue and/or the second longitudinal length may correspond to the depth within the tissue.

The first biopsy sample may comprise a biopsy core or cylinder and/or the second biopsy sample may comprise a biopsy core or cylinder.

The first biopsy sample may comprise a first portion of the tissue and the second biopsy sample may comprise a second portion of the tissue;

wherein the first portion of the tissue may have been adjacent and/or connected to the second portion of the tissue.

The first portion of the tissue may have been adjacent and/or connected to the second portion of the tissue along some, most or all the axial length of the first and/or second portion of the tissue.

The biopsy needle may be arranged and adapted to produce the first and second samples substantially at the same time.

The biopsy needle may be arranged and adapted to produce the first and second samples when inserted into the tissue a single time.

The biopsy needle may comprise a needle comprising a first hollow tube or cylinder and a second hollow tube or cylinder.

The first hollow tube or cylinder and second hollow tube or cylinder may be conjoined.

The first hollow tube or cylinder and second hollow tube or cylinder may be conjoined along some, most or all of an axial length of the first and/or an axial length of the second hollow tube or cylinder.

According to an aspect there is provided apparatus comprising:

a biopsy needle comprising one or more ambient ionisation devices;

a control system arranged and adapted to energise the one or more ambient ionisation devices in order to generate aerosol, smoke or vapour from a biopsy sample within the biopsy needle; and an analyser for analysing the aerosol, smoke or vapour.

The one or more ambient ionisation devices may comprise one or more electrodes arranged and adapted to contact the biopsy sample to generate the aerosol, smoke or vapour.

The one or more electrodes may comprise a bipolar device or a monopolar device.

The one or more electrodes may comprise either: (i) a monopolar device, wherein the apparatus optionally further comprises a separate return electrode; (ii) a bipolar device; or (iii) a multi-phase RF device, wherein the apparatus optionally further comprises a separate return electrode or electrodes.

The one or more electrodes may comprise a rapid evaporation ionisation mass spectrometry ("REIMS") device.

The control system may be arranged and adapted to apply an AC or RF voltage to the one or more electrodes in order to generate the aerosol, smoke or vapour.

The control system may be arranged and adapted to apply one or more pulses of the AC or RF voltage to the one or more electrodes.

Application of the AC or RF voltage to the one or more electrodes may cause heat to be dissipated into the sample.

The one or more ambient ionisation devices may comprise a laser for irradiating the sample.

The one or more ambient ionisation devices may be arranged and adapted to generate aerosol, smoke or vapour from the sample by direct evaporation or vaporisation of sample material from the sample by Joule heating or diathermy.

The analyser may comprise a collision surface, and wherein the apparatus may be arranged and adapted to cause at least some of the aerosol, smoke and/or vapour to impact upon the collision surface in order to form analyte ions.

The analyser may comprise: (i) a mass analyser or filter and/or ion mobility analyser for mass analysing and/or ion mobility analysing the aerosol, smoke, vapour, or the analyte ions and/or ions derived from the aerosol, smoke, vapour, the analyte ions; (ii) an ion mobility device for determining the ion mobility, collision cross section or interaction cross section of the aerosol, smoke, vapour, or the analyte ions and/or ions derived from the aerosol, smoke, vapour, the analyte ions; and/or (iii) one or more fragmentation, collision or reaction devices for fragmenting or reacting the aerosol, smoke, vapour, or the analyte ions.

According to an aspect there is provided a biopsy needle comprising one or more ambient ionisation devices.

The one or more ambient ionisation devices may comprise one or more electrodes arranged and adapted to contact a biopsy sample within the biopsy needle to generate aerosol, smoke or vapour.

The one or more electrodes may comprise a bipolar device or a monopolar device.

The one or more electrodes may comprise either: (i) a monopolar device, wherein the apparatus optionally further comprises a separate return electrode; (ii) a bipolar device; or (iii) a multi-phase RF device, wherein the apparatus optionally further comprises a separate return electrode or electrodes.

The one or more electrodes may comprise a rapid evaporation ionisation mass spectrometry ("REIMS") device.

The one or more ambient ionisation devices may comprise a laser for irradiating a biopsy sample within the biopsy needle.

According to an aspect there is provided a method comprising:

providing a biopsy needle comprising one or more ambient ionisation devices;

energising the one or more ambient ionisation devices in order to generate aerosol, smoke or vapour from a biopsy sample within the biopsy needle; and analysing the aerosol, smoke or vapour.

The one or more ambient ionisation devices may comprise one or more electrodes arranged and adapted to contact the biopsy sample to generate the aerosol, smoke or vapour.

The one or more electrodes may comprise a bipolar device or a monopolar device.

The one or more electrodes may comprise either: (i) a monopolar device, wherein the apparatus optionally further comprises a separate return electrode; (ii) a bipolar device; or (iii) a multi-phase RF device, wherein the apparatus optionally further comprises a separate return electrode or electrodes.

The one or more electrodes may comprise a rapid evaporation ionisation mass spectrometry ("REIMS") device.

Energising the one or more ambient ionisation devices may comprise applying an AC or RF voltage to the one or more electrodes in order to generate the aerosol, smoke or vapour.

Applying the AC or RF voltage to the one or more electrodes may comprise applying one or more pulses of the AC or RF voltage to the one or more electrodes.

Applying the AC or RF voltage to the one or more electrodes may cause heat to be dissipated into the sample.

The one or more ambient ionisation devices may comprise a laser for irradiating the sample.

The method may comprise generating the aerosol, smoke or vapour from the sample by direct evaporation or vaporisation of sample material from the sample by Joule heating or diathermy.

The method may comprise causing at least some of the aerosol, smoke and/or vapour to impact upon a collision surface in order to form analyte ions.

Analysing the aerosol, smoke or vapour may comprise: (i) mass analysing and/or ion mobility analysing the aerosol, smoke, vapour, or the analyte ions and/or ions derived from the aerosol, smoke, vapour, the analyte ions; (ii) determining the ion mobility, collision cross section or interaction cross section of the aerosol, smoke, vapour, or the analyte ions and/or ions derived from the aerosol, smoke, vapour, the analyte ions; and/or (iii) fragmenting or reacting the aerosol, smoke, vapour, or the analyte ions.

The method may comprise inserting the biopsy needle into a tissue so as to provide the biopsy sample within the biopsy needle.

The method may comprise energising the one or more ambient ionisation devices when the biopsy sample is inserted into the tissue.

According to an aspect there is provided a method comprising:

sampling tissue to produce one or more biopsy samples;

analysing the one or more biopsy samples; and performing a diagnostic or surgical procedure using a first device that may comprise generating analyte ions from tissue and analysing the analyte ions, wherein one or more operational parameters of the first device are calibrated, optimised or varied on the basis of the analysis of the one or more biopsy samples.

One or more of the one or more biopsy samples may comprise a sample of tissue having a longitudinal length.

The composition of the sample of tissue may vary or change along the longitudinal length.

The longitudinal length may correspond to the depth within a tissue.

One or more of the one or more biopsy samples may comprise a biopsy core or cylinder.

Analysing the one or more biopsy samples may comprise generating analyte ions from the one or more biopsy samples and analysing the analyte ions.

Generating analyte ions from the one or more biopsy samples may comprise generating analyte ions from the one or more biopsy samples using an ambient ionisation ion source.

The ambient ionisation ion source may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The step of generating analyte ions from the one or more biopsy samples may comprise generating aerosol, smoke or vapour from the one or more biopsy samples, and ionising the aerosol, smoke or vapour to generate the analyte ions.

The method may comprise causing at least some of the aerosol, smoke and/or vapour to impact upon a collision surface in order to generate the analyte ions.

The step of generating analyte ions from the one or more biopsy samples may comprise contacting one or more electrodes to the one or more biopsy samples to generate the aerosol, smoke or vapour.

The one or more electrodes may comprise a bipolar device or a monopolar device.

The one or more electrodes may comprise either: (i) a monopolar device, wherein the apparatus optionally further comprises a separate return electrode; (ii) a bipolar device; or (iii) a multi-phase RF device, wherein the apparatus optionally further comprises a separate return electrode or electrodes.

The one or more electrodes may comprise a rapid evaporation ionisation mass spectrometry ("REIMS") device.

The method may comprise applying an AC or RF voltage to the one or more electrodes in order to generate the aerosol, smoke or vapour.

The step of applying the AC or RF voltage to the one or more electrodes may comprise applying one or more pulses of the AC or RF voltage to the one or more electrodes.

Applying the AC or RF voltage to the one or more electrodes may cause heat to be dissipated into the sample.

The step of generating analyte ions from the one or more biopsy samples may comprise directing a laser beam onto the one or more biopsy samples to generate the analyte ions.

Analysing analyte ions may comprise: (i) mass analysing and/or ion mobility analysing the analyte ions and/or ions derived from the analyte ions; (ii) determining the ion mobility, collision cross section or interaction cross section of the analyte ions and/or ions derived from the analyte ions; and/or (iii) fragmenting or reacting the analyte ions.

Analysing the one or more biopsy samples may comprise analysing the one or more biopsy samples using the first device.

The first device may comprise an ambient ionisation ion source.

The ambient ionisation ion source may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The step of performing a diagnostic or surgical procedure may comprise using the first device to generate aerosol, smoke or vapour from the tissue, and ionising the aerosol, smoke or vapour in order to generate the analyte ions.

The method may comprise causing at least some of the aerosol, smoke or vapour to impact upon a collision surface in order to generate the analyte ions.

Using the first device to generate aerosol, smoke or vapour from the tissue may comprise contacting the tissue with one or more electrodes to generate the aerosol, smoke or vapour.

The one or more electrodes may comprise a bipolar device or a monopolar device.

The one or more electrodes may comprise either: (i) a monopolar device, wherein the apparatus optionally further comprises a separate return electrode; (ii) a bipolar device; or (iii) a multi-phase RF device, wherein the apparatus optionally further comprises a separate return electrode or electrodes.

The method may comprise applying an AC or RF voltage to the one or more electrodes in order to generate the aerosol, smoke or vapour.

Applying the AC or RF voltage to the one or more electrodes may comprise applying one or more pulses of the AC or RF voltage to the one or more electrodes.

Applying the AC or RF voltage to the one or more electrodes may cause heat to be dissipated into the sample.

The first device and/or the one or more electrodes may comprise a rapid evaporation ionisation mass spectrometry ("REIMS") device.

The first device may comprise a laser for irradiating the sample.

Analysing the analyte ions may comprise: (i) mass analysing and/or ion mobility analysing the analyte ions and/or ions derived from the analyte ions; (ii) determining the ion mobility, collision cross section or interaction cross section of the analyte ions and/or ions derived from the analyte ions; and/or (iii) fragmenting or reacting the analyte ions.

The first device may comprise an electrosurgical tool.

The first device may comprise an electrosurgical device, a diathermy device, an ultrasonic device, hybrid ultrasonic electrosurgical device, surgical water jet device, hybrid electrosurgery, argon plasma coagulation device, hybrid argon plasma coagulation device and water jet device and/or a laser device.

Analysing the one or more biopsy samples may comprise determining spatially resolved information regarding the one or more biopsy samples and/or the tissue; and the one or more operational parameters may be calibrated, optimised or varied on the basis of the spatially resolved information.

The one or more operational parameters may be calibrated, optimised or varied depending on the position of the first device during the diagnostic or surgical procedure.

Analysing the one or more biopsy samples may comprise determining one or more tissue types of the one or more biopsy samples and/or the tissue; and the one or more operational parameters may be calibrated, optimised or varied on the basis of the determined tissue types.

The one or more operational parameters may be calibrated, optimised or varied depending on the type of tissue being analysed by the first device during the diagnostic or surgical procedure.

The one or more tissue types may be selected from the group consisting of: (i) healthy tissue; (ii) diseased or tumour tissue; (iii) tissue comprising both healthy and diseased cells, wherein the diseased cells are optionally cancer cells; (iv) a type or grade of diseased or tumour tissue; (v) tissue at a border region of an organ and/or tumour; and/or (vi) tissue away from a border region of an organ and/or tumour.

The one or more operational parameters of the first device may comprise: (i) the magnitude and/or frequency of a voltage provided to the first device; (ii) a temperature of the first device; (iii) the composition of a matrix added to aerosol, smoke or vapour generated by the first device; (iv) the temperature of a collision surface onto which aerosol, smoke or vapour generated by the first device is impacted; (v) a voltage applied to a collision surface onto which aerosol, smoke or vapour generated by the first device is impacted; (vi) one or more operational parameters of a mass analyser or filter for mass analysing analyte ions and/or ions derived from the analyte ions; (vii) one or more operational parameters of an ion mobility device for determining the ion mobility, collision cross section or interaction cross section of analyte ions and/or ions derived from the analyte ions; and/or (viii) one or more operational parameters of a collision, reaction or fragmentation device for fragmenting or reacting analyte ions.

The method may comprise generating or updating a library or database on the basis of the analysis, wherein the library or database is used for calibrating or optimising the first device during the diagnostic or surgical procedure.

According to an aspect there is provided apparatus comprising:

a first device for performing a diagnostic or surgical procedure, wherein the first device may be arranged and adapted to generate analyte ions from tissue and to analyse the analyte ions; and a control system arranged and adapted to calibrate, optimise or vary one or more operational parameters of the first device for or during a diagnostic or surgical procedure on the basis of analysis of one or more biopsy samples sampled from the tissue.

One or more of the one or more biopsy samples may comprise a sample of tissue having a longitudinal length.

The composition of the sample of tissue may vary or change along the longitudinal length.

The longitudinal length may correspond to the depth within the tissue.

One or more of the one or more biopsy samples may comprise a biopsy core or cylinder.

The analysis of the one or more biopsy samples may comprise analysis of the one or more biopsy samples performed using the first device.

The first device may comprise an ambient ionisation ion source.

The ambient ionisation ion source may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The first device may be arranged and adapted to generate aerosol, smoke or vapour from the tissue, and to ionise the aerosol, smoke or vapour in order to generate the analyte ions.

The apparatus may comprise a collision surface, wherein the apparatus may be arranged and adapted to cause at least some of the aerosol, smoke or vapour to impact upon the collision surface in order to generate the analyte ions.

The first device may comprise one or more electrodes arranged and adapted to contact the tissue in order to generate the aerosol, smoke or vapour.

The one or more electrodes may comprise a bipolar device or a monopolar device.

The one or more electrodes may comprise either: (i) a monopolar device, wherein the apparatus optionally further comprises a separate return electrode; (ii) a bipolar device; or (iii) a multi-phase RF device, wherein the apparatus optionally further comprises a separate return electrode or electrodes.

The apparatus may comprise a device arranged and adapted to apply an AC or RF voltage to the one or more electrodes in order to generate the aerosol, smoke or vapour.

The device for applying the AC or RF voltage to the one or more electrodes may be arranged and adapted to apply one or more pulses of the AC or RF voltage to the one or more electrodes.

Application of the AC or RF voltage to the one or more electrodes may cause heat to be dissipated into the sample.

The first device and/or the one or more electrodes may comprise a rapid evaporation ionisation mass spectrometry ("REIMS") device.

The first device may comprise a laser for irradiating the sample.

The apparatus may comprise: (i) a mass analyser or filter and/or ion mobility analyser for mass analysing and/or ion mobility analysing analyte ions and/or ions derived from the analyte ions; (ii) an ion mobility device for determining the ion mobility, collision cross section or interaction cross section of analyte ions and/or ions derived from the analyte ions; and/or (iii) a fragmentation, reaction or collision device for fragmenting or reacting analyte ions.

The first device may comprise an electrosurgical tool.

The first device may comprise an electrosurgical device, a diathermy device, an ultrasonic device, hybrid ultrasonic electrosurgical device, surgical water jet device, hybrid electrosurgery, argon plasma coagulation device, hybrid argon plasma coagulation device and water jet device and/or a laser device.

The control system may be arranged and adapted to calibrate, optimise or vary the one or more operational parameters on the basis of spatially resolved information determined from the analysis of the one or more biopsy samples.

The control system may be arranged and adapted to calibrate, optimise or vary the one or more operational parameters depending on the position of the first device during the diagnostic or surgical procedure.

The control system may be arranged and adapted to calibrate, optimise or vary the one or more operational parameters on the basis of one or more tissue types determined from the analysis of the one or more biopsy samples.

The control system may be arranged and adapted to calibrate, optimise or vary the one or more operational parameters depending on the type of tissue being analysed by the first device during the diagnostic or surgical procedure.

The one or more tissue types may be selected from the group consisting of: (i) healthy tissue; (ii) diseased or tumour tissue; (iii) tissue comprising both healthy and diseased cells, wherein the diseased cells are optionally cancer cells; (iv) a type or grade of diseased or tumour tissue; (v) tissue at a border region of an organ and/or tumour; and/or (vi) tissue away from a border region of an organ and/or tumour.

The one or more operational parameters of the first device may comprise: (i) the magnitude and/or frequency of a voltage provided to the first device; (ii) a temperature of the first device; (iii) the composition of a matrix added to aerosol, smoke or vapour generated by the first device; (iv) the temperature of a collision surface onto which aerosol, smoke or vapour generated by the first device is impacted; (v) a voltage applied to a collision surface onto which aerosol, smoke or vapour generated by the first device is impacted; (vi) one or more operational parameters of a mass analyser or filter for mass analysing analyte ions and/or ions derived from the analyte ions; (vii) one or more operational parameters of an ion mobility device for determining the ion mobility, collision cross section or interaction cross section of analyte ions and/or ions derived from the analyte ions; and/or (viii) one or more operational parameters of a collision, reaction or fragmentation device for fragmenting or reacting analyte ions.

The control system may be arranged and adapted to generate or update a library or database on the basis of the analysis, and to calibrate or optimise the first device using the library or database during the diagnostic or surgical procedure.

In any of the various aspects and embodiments described herein, analysis of the analyte ions may result in spectrometric data and/or ion mobility data which may then be analysed.

Analysing the spectrometric data and/or ion mobility data may comprise analysing one or more sample spectra so as to classify a sample.

Analysing the one or more sample spectra so as to classify the sample may comprise unsupervised analysis of the one or more sample spectra (e.g., for dimensionality reduction) and/or supervised analysis of the one or more sample spectra (e.g., for classification)

Analysing the one or more sample spectra may comprise unsupervised analysis (e.g., for dimensionality reduction) followed by supervised analysis (e.g., for classification).

Analysing the one or more sample spectra may comprise using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; and (xxii) subspace discriminant analysis; (xxiii) k-nearest neighbours (KNN); (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

Analysing the one or more sample spectra so as to classify the sample may comprise developing a classification model or library using one or more reference sample spectra.

Analysing the one or more sample spectra so as to classify the sample may comprise performing linear discriminant analysis (LDA) (e.g., for classification) after performing principal component analysis (PCA) (e.g., for dimensionality reduction).

Analysing the one or more sample spectra so as to classify the sample may comprise performing a maximum margin criteria (MMC) process (e.g., for classification) after performing principal component analysis (PCA) (e.g., for dimensionality reduction). Analysing the one or more sample spectra so as to classify the sample may comprise defining one or more classes within a classification model or library.

Analysing the one or more sample spectra so as to classify the sample may comprise defining one or more classes within a classification model or library manually or automatically according to one or more class or cluster criteria.

The one or more class or cluster criteria for each class may be based on one or more of: a distance between one or more pairs of reference points for reference sample spectra within a model space; a variance value between groups of reference points for reference sample spectra within a model space; and a variance value within a group of reference points for reference sample spectra within a model space.

The one or more classes may each be defined by one or more class definitions.

The one or more class definitions may comprise one or more of: a set of one or more reference points for reference sample spectra, values, boundaries, lines, planes, hyperplanes, variances, volumes, Voronoi cells, and/or positions, within a model space; and one or more positions within a class hierarchy.

Analysing the one or more sample spectra so as to classify the sample may comprise using a classification model or library to classify one or more unknown sample spectra.

Analysing the one or more sample spectra so as to classify the sample may comprise classifying one or more sample spectra manually or automatically according to one or more classification criteria.

The one or more classification criteria may comprise one or more of:

a distance between one or more projected sample points for one or more sample spectra within a model space and a set of one or more reference points for one or more reference sample spectra, values, boundaries, lines, planes, hyperplanes, volumes, Voronoi cells, or positions, within the model space being below a distance threshold or being the lowest such distance;

a position for one or more projected sample points for one or more sample spectra within a model space being one side or other of one or more reference points for one or more reference sample spectra, values, boundaries, lines, planes, hyperplanes, or positions, within the model space;

a position for one or more projected sample points for one or more sample spectra within a model space being within one or more volumes or Voronoi cells within the model space; and a probability or classification score being above a probability or classification score threshold or being the highest such probability or classification score.

According to an aspect there is provided a mass and/or ion mobility analyser comprising apparatus as described above.

According to an aspect there is provided a method of mass spectrometry and/or method of ion mobility spectrometry comprising a method as described above.

The mass and/or ion mobility spectrometer may obtain data in negative ion mode only, positive ion mode only, or in both positive and negative ion modes. Positive ion mode spectrometric data may be combined or concatenated with negative ion mode spectrometric data.

Ion mobility spectrometric data may be obtained using different ion mobility drift gases and/or dopants. This data may then be combined or concatenated.

Various embodiments are contemplated which relate to generating smoke, aerosol or vapour from a target (details of which are provided elsewhere herein) using an ambient ionisation ion source. The aerosol, smoke or vapour may then be mixed with a matrix and aspirated into a vacuum chamber of a mass spectrometer and/or ion mobility spectrometer. The mixture may be caused to impact upon a collision surface causing the aerosol, smoke or vapour to be ionised by impact ionization which results in the generation of analyte ions. The resulting analyte ions (or fragment or product ions derived from the analyte ions) may then be mass analysed and/or ion mobility analysed and the resulting mass spectrometric data and/or ion mobility spectrometric data may be subjected to multivariate analysis or other mathematical treatment in order to determine one or more properties of the target in real time.

According to an embodiment the first device for generating aerosol, smoke or vapour from the target may comprise a tool which utilises an RF voltage, such as a continuous RF waveform.

Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimeters.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

According to various embodiments the mass spectrometer and/or ion mobility spectrometer may obtain data in negative ion mode only, positive ion mode only, or in both positive and negative ion modes. Positive ion mode spectrometric data may be combined or concatanated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated.

It will be apparent that the requirement to add a matrix or a reagent directly to a sample may prevent the ability to perform in vivo analysis of tissue and also, more generally, prevents the ability to provide a rapid simple analysis of target material.

According to other embodiments the ambient ionisation ion source may comprise an ultrasonic ablation ion source or a hybrid electrosurgical—ultrasonic ablation source that generates a liquid sample which is then aspirated as an aerosol. The ultrasonic ablation ion source may comprise a focused or unfocused ultrasound.

Optionally, the first device comprises or forms part of an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

BRIEF DESCRIPTION OF THE DRAWINGS

Various embodiments will now be described, by way of example only, and with reference to the accompanying drawings in which:

FIG. 3 shows schematically a mucosa or mucosal membrane comprising biological tissue and bacteria;

FIG. 4 shows schematically how analytes present in a mucosa may be useful in identifying a number of clinical disorders;

FIG. 6 shows various approaches for microbial analysis together with a real time rapid and direct analysis method using ambient mass spectrometry according to various embodiments;

FIG. 7 illustrates the technique of Desorption Electrospray Ionisation ("DESI") according to various embodiments;

FIG. 13A shows averaged desorption electrospray ionisation ("DESI") mass spectra from a pregnant (highlighted in blue) and a non-pregnant group (highlighted in red) acquired in negative ion mode in the mass range m/z 150-1000, FIG. 13B shows principal component analysis and discriminatory analysis using recursive maximum margin criterion ("RMMC"), FIG. 13C shows analysis with leave-one-out cross-validation for enhanced separation of group classes with highly accurate identification (>80%) based on chemical signatures in the vaginal mucosal membrane.

FIG. 14A shows desorption electrospray ionisation ("DESI") mass spectral analysis of a bacteria sample on a swab in accordance with various embodiments and shows that bacterial samples can be detected using DESI and FIG. 14B shows a comparison with rapid evaporative ionisation mass spectrometry ("REIMS") analysis in conjunction with a Time of Flight mass analysis of a bacterial sample directly from an agar plate;

FIG. 15B shows a PCA plot showing a separation between the vaginal mucosa (pregnant and non-pregnant group) from the microorganism species within the first two components and FIG. 15C shows a separation between the different bacteria and fungi species;

FIG. 20A illustrates a mass spectrum obtained when using a standard cotton swab, FIG. 20B shows how an improved sensitivity (especially improved lipid signal) may be obtained using a modified swab and FIG. 20C shows how an improved sensitivity (especially improved lipid signal) may be obtained using a modified swab according to various embodiments;

FIG. 22 shows schematically a solid-phase microextraction ("SPME") swab sample preparation workflow for the extraction of analytes in saliva matrix followed by desorption electrospray ionisation ("DESI") mass spectrometry analysis in accordance with various embodiments;

FIG. 23A shows a saliva mass spectrum obtained in negative ion mode (left) and positive ion mode (right) using a standard medical swab, FIG. 23B shows a saliva mass spectrum obtained in negative ion mode (left) and positive ion mode (right) using a standard medical swab coated with three layers of C18 (octadecyl) sorbent, FIG. 23C shows a saliva mass spectrum obtained in negative ion mode (left) and positive ion mode (right) using a standard medical swab coated with three layers of C18 (octadecyl) EC (end capped) sorbent.

FIG. 25A shows a Desorption Electrospray Ionisation ("DESI") device.

DETAILED DESCRIPTION

Figure 1:
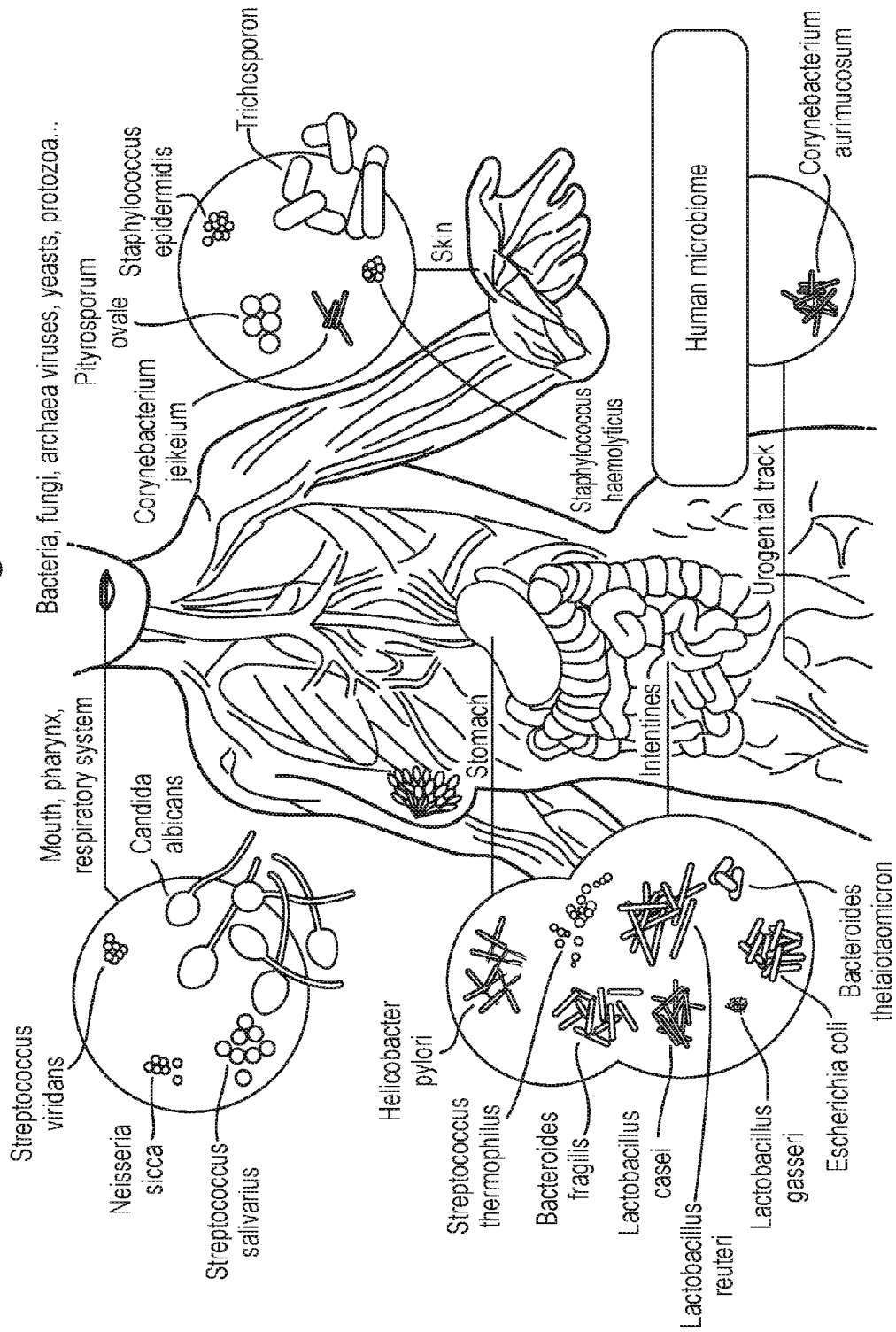
FIG. 1 shows schematically a variety of microbes that are present in the human microbiome.

Various embodiments will now be described in more detail. Some of the embodiments which are described in more detail relate to using a Desorption Electrospray Ionisation ("DESI") ion source to analyse a standard medical swab.

However, other embodiments are contemplated wherein a different ambient ionisation ion source may be used.

Ambient Ionisation Ion Sources

Various embodiments as described herein are described in the context of using a Desorption Electrospray Ionisation ("DESI") ion source to generate a spray of electrically charged droplets. However, other embodiments are contemplated wherein other devices may be used to generate analyte ions.

The devices or ion sources may comprise ambient ionisation ion sources which are characterised by the ability to generate analyte ions from a native or unmodified target. By way of contrast, other types of ionisation ion sources such as Matrix Assisted Laser Desorption Ionisation ("MALDI") ion sources require the addition of a matrix or reagent to the sample prior to ionisation.

It will be apparent that the requirement to add a matrix or a reagent to a sample prevents the ability to perform in vivo analysis of tissue and also, more generally, prevents the ability to provide a rapid simple analysis of target material.

In contrast, therefore, ambient ionisation techniques are particularly beneficial since firstly they do not require the addition of a matrix or a reagent (and hence are suitable for the analysis of in vivo tissue) and since secondly they enable a rapid simple analysis of target material to be performed.

A number of different ambient ionisation techniques are known and are intended to fall within the scope of the present invention. Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from native (i.e. untreated or unmodified) samples. A particular benefit of the various ambient ionisation techniques which fall within the scope of the present invention is that the various ambient ionisation techniques do not require any prior sample preparation. As a result, the various ambient ionisation techniques enable both in vivo and ex vivo tissue samples to be analysed without necessitating the time and expense of adding a matrix or reagent to the tissue sample or other target material.

A list of ambient ionisation techniques which are intended to fall within the scope of the present invention are given in the following table:

| Acronym | Ionisation technique |
| --- | --- |
| DESI | Desorption electrospray ionisation |
| DeSSI | Desorption sonic spray ionisation |
| DAPPI | Desorption atmospheric pressure photoionisation |
| EASI | Easy ambient sonic-spray ionisation |
| JeDI | Jet desorption electrospray ionisation |
| TM-DESI | Transmission mode desorption electrospray ionisation |
| LMJ-SSP | Liquid microjunction-surface sampling probe |
| DICE | Desorption ionisation by charge exchange |
| Nano-DESI | Nanospray desorption electrospray ionisation |
| EADESI | Electrode-assisted desorption electrospray ionisation |
| APTDCI | Atmospheric pressure thermal desorption chemical ionisation |
| V-EASI | Venturi easy ambient sonic-spray ionisation |

-continued

| Acronym | Ionisation technique |
| --- | --- |
| AFAI | Air flow-assisted ionisation |
| LESA | Liquid extraction surface analysis |
| PTC-ESI | Pipette tip column electrospray ionisation |
| AFADESI | Air flow-assisted desorption electrospray ionisation |
| DEFFI | Desorption electro-flow focusing ionisation |
| ESTASI | Electrostatic spray ionisation |
| PASIT | Plasma-based ambient sampling ionisation transmission |
| DAPCI | Desorption atmospheric pressure chemical ionisation |
| DART | Direct analysis in real time |
| ASAP | Atmospheric pressure solid analysis probe |
| APTDI | Atmospheric pressure thermal desorption ionisation |
| PADI | Plasma assisted desorption ionisation |
| DBDI | Dielectric barrier discharge ionisation |
| FAPA | Flowing atmospheric pressure afterglow |
| HAPGDI | Helium atmospheric pressure glow discharge ionisation |
| APGDDI | Atmospheric pressure glow discharge desorption ionisation |
| LTP | Low temperature plasma |
| LS-APGD | Liquid sampling-atmospheric pressure glow discharge |
| MIPDI | Microwave induced plasma desorption ionisation |
| MFGDP | Microfabricated glow discharge plasma |
| RoPPI | Robotic plasma probe ionisation |
| PLASI | Plasma spray ionisation |
| MALDESI | Matrix assisted laser desorption electrospray ionisation |
| ELDI | Electrospray laser desorption ionisation |
| LDTD | Laser diode thermal desorption |
| LAESI | Laser ablation electrospray ionisation |
| CALDI | Charge assisted laser desorption ionisation |
| LA-FAPA | Laser ablation flowing atmospheric pressure afterglow |
| LADESI | Laser assisted desorption electrospray ionisation |
| LDESI | Laser desorption electrospray ionisation |
| LEMS | Laser electrospray mass spectrometry |
| LSI | Laser spray ionisation |
| IR-LAMICI | Infrared laser ablation metastable induced chemical ionisation |
| LDSPI | Laser desorption spray post-ionisation |
| PAMLDI | Plasma assisted multiwavelength laser desorption ionisation |
| HALDI | High voltage-assisted laser desorption ionisation |
| PALDI | Plasma assisted laser desorption ionisation |
| ESSI | Extractive electrospray ionisation |
| PESI | Probe electrospray ionisation |
| ND-ESSI | Neutral desorption extractive electrospray ionisation |
| PS | Paper spray |
| DIP-APCI | Direct inlet probe-atmospheric pressure chemical ionisation |
| TS | Touch spray |
| Wooden-tip | Wooden-tip electrospray |
| CBS-SPME | Coated blade spray solid phase microextraction |
| TSI | Tissue spray ionisation |
| RADIO | Radiofrequency acoustic desorption ionisation |
| LIAD-ESI | Laser induced acoustic desorption electrospray ionisation |
| SAWN | Surface acoustic wave nebulization |
| UASI | Ultrasonication-assisted spray ionisation |
| SPA-nanoESI | Solid probe assisted nanoelectrospray ionisation |
| PAUSI | Paper assisted ultrasonic spray ionisation |
| DPESI | Direct probe electrospray ionisation |
| ESA-Py | Electrospray assisted pyrolysis ionisation |
| APPIS | Ambient pressure pyroelectric ion source |
| RASTIR | Remote analyte sampling transport and ionisation relay |
| SACI | Surface activated chemical ionisation |
| DEMI | Desorption electrospray metastable-induced ionisation |
| REIMS | Rapid evaporative ionisation mass spectrometry |
| SPAM | Single particle aerosol mass spectrometry |
| TDAMS | Thermal desorption-based ambient mass spectrometry |
| MAII | Matrix assisted inlet ionisation |
| SAII | Solvent assisted inlet ionisation |
| SwiFERR | Switched ferroelectric plasma ioniser |
| LPTD | Leidenfrost phenomenon assisted thermal desorption |

According to an embodiment the ambient ionisation ion source may comprise a rapid evaporative ionisation mass spectrometry ("REIMS") ion source wherein an RF voltage is applied to electrodes in order to generate an aerosol or plume of surgical smoke by Joule heating.

However, it will be appreciated that numerous other ambient ion sources including those referred to above may be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 µm which corresponds with the peak in the water absorption spectrum. According to various embodiments the ambient ionisation ion source may comprise a laser ablation ion source having a wavelength close to 2.94 µm, i.e., on the basis of the high absorption coefficient of water at 2.94 µm. According to an embodiment the laser ablation ion source may comprise an Er:YAG laser which emits radiation at 2.94 µm.

Other embodiments are contemplated wherein a mid-infrared optical parametric oscillator ("OPO") may be used to produce a laser ablation ion source having a longer wavelength than 2.94 µm. For example, an Er:YAG pumped ZGP-OPO may be used to produce laser radiation having a wavelength of e.g. 6.1 µm, 6.45 µm or 6.73 µm. In some situations it may be advantageous to use a laser ablation ion source having a shorter or longer wavelength than 2.94 µm since only the surface layers will be ablated and less thermal damage may result. According to an embodiment a Co:MgF2 laser may be used as a laser ablation ion source wherein the laser may be tuned from 1.75-2.5 µm. According to another embodiment an optical parametric oscillator ("OPO") system pumped by a Nd:YAG laser may be used to produce a laser ablation ion source having a wavelength between 2.9-3.1 µm. According to another embodiment a $CO_2$ laser having a wavelength of 10.6 µm may be used to generate the aerosol, smoke or vapour.

According to other embodiments the ambient ionisation ion source may comprise an ultrasonic ablation ion source which generates a liquid sample which is then aspirated as an aerosol. The ultrasonic ablation ion source may comprise a focused or unfocussed source.

According to an embodiment the first device for generating aerosol, smoke or vapour from one or more regions of a target may comprise an electrosurgical tool which utilises a continuous RF waveform. According to other embodiments a radiofrequency tissue dissection system may be used which is arranged to supply pulsed plasma RF energy to a tool. The tool may comprise, for example, a PlasmaBlade®. Pulsed plasma RF tools operate at lower temperatures than conventional electrosurgical tools (e.g.

40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

Real-Time Rapid Analysis Using Desorption Electrospray Ionisation ("DESI") Mass Spectrometry of Medical Swabs According to various embodiments swabs, medical swabs or standard medical swabs may be directly analysed using desorption electrospray ionisation ("DESI") mass spectrometry, and in particular the specific microbe(s) on the surface of swabs may be identified by their chemical signature within a short period of time.

The rapid identification of specific microbes from the surface of swabs enables rapid diagnosis of various infections to be made. Furthermore, biomarkers, such as metabolomic, inflammatory and/or microbial markers can be analysed, e.g., identified or determined, which e.g. enables the rapid analysis, e.g., identification, of different diseases, such as cancer, dysbiosis, infections, and/or any of the other diseases listed elsewhere herein.

Various embodiments will be described in more detail below which relate to mucosal analysis, e.g., diagnostics.

One of many potential applications of the various techniques which are disclosed herein is the ability to identify, by analysing vaginal mucosal samples, whether or not a patient is at an increased risk of suffering a preterm (premature) delivery. Results according to various embodiments may optionally be compared with standard microbial testing.

A real-time rapid medical swab analysis approach is disclosed which utilises desorption electrospray ionisation ("DESI") mass spectrometry to reveal biomarkers such as pathogenic and/or inflammatory metabolomic markers.

In particular, various chemically modified swabs for use with desorption electrospray ionisation ("DESI") are disclosed. Various chemically modified swabs have been found to exhibit an improved sensitivity compared with conventional (non-modified) swabs.

It has also been found that a significant enhancement in signal intensity can be obtained by rotating or continuously rotating the swabs whilst analysing the swab using a desorption electrospray ionisation ("DESI") ion source.

Further embodiments are also disclosed below which relate to methods of rapid evaporative ionisation mass spectrometry ("REIMS") analysis (rather than desorption electrospray ionisation ("DESI") analysis) of a swab wherein the swab is dipped, soaked or otherwise immersed in a fluid (such as water) prior to be being subjected to rapid evaporative ionisation mass spectrometry ("REIMS") analysis.

Soaking a swab in a fluid such as water prior to rapid evaporative ionisation mass spectrometry has been found to have the effect of improving the signal intensity.

According to various further embodiments, desorption electrospray ionisation ("DESI") mass spectrometry of swabs may be used, e.g. for toxicological screening, such as on-site emergency toxicological screening, drug testing, such as roadside drug testing, doping testing and so on.

Desorption Electrospray Ionisation ("DESI") Mass Spectrometry Analysis of Mucosal Samples Various embodiments will now be described in more detail which relate to a non-invasive approach for mucosal analysis, e.g., diagnostics.

Medical swabs are a standard collection device for mucosal membranes and are commonly used for diagnosis of pathogenic related diseases. Routine clinical microbiology techniques for mucosal swab diagnostics are time consuming, lack sensitivity and are generally qualitative. Standard medical swabs which have been used to sample a mucosal membrane are sent to a microbiological laboratory where the sample is then analysed by culturing microbes. However, this conventional approach typically takes 24-48 hours and delays diagnosis of the patient.

By way of contrast, various embodiments will now be described in more detail which allow mucosal membrane samples to be analysed immediately or in real time, thereby avoiding the 24-48 hour delay which is common according to conventional techniques.

In particular, according to various embodiments, a method is provided that comprises providing a biological sample on a swab, directing a spray of charged droplets onto a surface of the swab in order to generate a plurality of analyte ions, and analysing the analyte ions.

Various embodiments relate to a method for rapid, direct analysis of medical swabs by desorption electrospray ionisation mass spectrometry without the need for extensive extraction protocols. According to various embodiments, ionisation of mucosal biomass occurs directly from a medical swab, such as a standard medical rayon swab, which may be rotating, before analysis in a mass and/or ion mobility spectrometer, e.g. for online chemical monitoring. According to various embodiments, multivariate modelling of acquired mass spectral fingerprints permits discrimination of differing mucosal surfaces, characterisation of biochemical alterations, e.g. induced by pregnancy, and/or rapid identification of intact bacterial and fungal species. The direct medical swab analysis by desorption electrospray ionisation mass spectrometry according to various embodiments may be used in a wide range of clinical applications, including rapid mucosal diagnostics and/or characterisation of clinically relevant changes in mucosal biochemistry.

Various embodiments relate to a non-invasive and culture-independent method that allows profiling, e.g., metabolomic profiling of mucosal membranes to be performed by direct analysis of clinical swabs using desorption electrospray ionisation ("DESI"), e.g. within a few minutes. These swabs may be used to give a fast diagnosis of disease including, e.g.: (i) microbial infection; (ii) dysbiosis; (iii) immunological disorders; (iv) cancer; and/or any of the other diseases listed elsewhere herein.

As described further below, a total of n=85 mucosal membrane models were collected from three cohorts (urogenital tract, nasal and oral cavity). The mucosal membrane samples were subjected to desorption electrospray ionisation ("DESI") mass spectral analysis and the resulting mass spectral data was subjected to multivariate statistical analysis. Multivariate statistical analysis was able to separate different mucosa classes and biomarker changes that can be associated with a diverse microbiome within the mucosa.

The microbiome comprises the community of microorganisms that inhabit human or non-human animal bodies, e.g., human bodies. Humans and non-human animals have co-evolved with microbes as a symbiotic system. Complex reactions of microbe communities influence health and disease.

FIG. 1 illustrates a variety of microbes that may be present in the human microbiome. As shown in FIG. 1, the human microbiome may include various bacteria, fungi, archaea, viruses, yeasts, protozoa, etc. which may be present, e.g., in the mouth, pharynx, respiratory system, skin, stomach, intestines, and/or urogenital tract, etc.

A "microbe", also known as a micro-organism, is an organism which is too small to be visible to the naked eye, i.e. is microscopic. A microbe may be selected from bacteria, fungi, archaea, algae, protozoa and viruses. Although the terms bacteria, fungi, archaea, algae, protozoa and viruses technically denote the plural form, it is common practice to use them also to denote the singular form. Consequently, the terms "bacteria" and "bacterium" are used interchangeably herein; the terms "fungi" and "fungus" are used interchangeably herein; the terms "archaea" and "archaeum" are used interchangeably herein; the terms "protozoa" and "protozoum" are used interchangeably herein; and the terms "viruses" and "virus" are used interchangeably herein.

In the case of a microbe, analysis may optionally be on any taxonomic level, for example, at the Kingdom, Phylum or Division, Class, Order, Family, Genus, Species and/or Strain level.

"Taxonomy" is the classification of organisms, and each level of classification may be referred to as a "taxon" (plural: taxa). Organisms may be classified into the following taxa in increasing order of specificity: Kingdom, Phylum or Division, Class, Order, Family, Genus, Species and Strain. Further subdivisions of each taxon may exist. It must be appreciated that within the vast scientific community there are some discrepancies within some taxonomic classifications. There may also be a lack of consensus with regard to the nomenclature of certain microbes, resulting in a particular microbe having more than one name or in two different microbes having the same name.

As a shorthand, the term "type" of microbe is used to refer to a microbe that differs from another microbe at any taxonomic level.

In some embodiments, the microbe may be selected from bacteria, fungi, archaea, algae and protozoa. In some embodiments, it may be selected from bacteria and fungi. In some embodiments, it may be selected from bacteria.

The microbe may be single-cellular or multi-cellular. If the microbe is a fungus, it may optionally be filamentous or single-cellular, e.g., a yeast.

A fungus may optionally be yeast. It may optionally be selected from the genus *Aspergillus, Arthroascus, Brettanomyces Candida, Cryptococcus, Debaryomyces, Geotrichum, Pichia, Rhodotorula, Saccharomyces, Trichosporon* and *Zygotorulaspora*.

It may optionally be selected from the species *Arthroascus schoenii, Brettanomyces bruxellensis, Candida albicans, C. ascalaphidarum, C. amphixiae, C. antarctica, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermedia, C. jeffresii, C. kefyr, C. keroseneae, C. krusei, C. lusitaniae, C. lyxosophila, C. maltosa, C. marina, C. membranifaciens, C. milleri, C. mogii, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis, C. ubatubensis, C. zemplinina, Cryptococcus neoformans, Cryptococcus uniguttulatus, Debaryomyces carsonii, Geotrichum capitatum, Trichosporon asahii Trichosporon mucoides, Trichosporon inkin, Saccharomyces cerevisiae, Pichia acaciae, Pichia anomala, Pichia capsulata, Pichia farinosa, Pichia guilliermondii, Pichia spartinae, Pichia ohmeri, Rhodotorula glutinous, Rhodotorula mucilaginosa, Saccharomyces boulardii, Saccharomyces cerevisiae* and/or *Zygotorulaspora florentinus*.

The protozoa may optionally be selected from the group of amoebae, flagellates, ciliates or sporozoa. It may optionally be selected from the genus *Acanthamoeba, Babesia, Balantidium, Cryptosporidium, Dientamoeba, Entamoeba, Giardia, Leishmania, Naegleria, Plasmodium Paramecium, Trichomonas, Trypanosoma, Typanosoma* and *Toxoplasma*.

The protozoa may optionally be of the species *Balantidium coli, Entamoeba histolytica, Giardia lamblia* (also known as *Giardia intestinalis*, or *Giardia duodenalis*), *Leishmania donovani, L. tropica, L. brasiliensis, Plasmodium falciparum, P. vivax, P. ovale, P. malariae, P. knowlesi, P. reichenowi, P. gaboni, P. mexicanum, P. floridense Trypanosoma brucei, Typanosoma evansi, Trypanosoma rhodesiense, Trypanosoma cruzi* and *Toxoplasma gondii*.

The bacteria may optionally be selected from the phylum Aquficae, Thermotogae, Thermodesulfobacteria, Deinococcus-Thermus, Chrysiogenetes, Chloroflexi, Thermomicrobia, Nitrospira, Deferribacteres, Cyanobacteria, Chlorobi, Proteobacteria, Firmicutes, Actinobacteria, Planctomycetes, Chlamydiae, Spirochaetes, Fibrobacteres, Acidobacteria, Bacteroidetes, Fusobacteria, Verrucomicrobia, Dictyoglomi, Gemmatomonadetes and/or Lentisphaerae.

The bacteria may optionally be selected from the class Actinobacteria, Alpha proteobacteria, Bacilli, Beta proteobacteria, Clostridia, Delta proteobacteria, Epsilonproteobacteria, Flavobacteriaceae, Fusobacteria, Gamma proteobacteria, Mikeiasis, Mollicute, or Negativicutes.

The bacteria may optionally be of the Order Aeromonadales, Actinomycetales, Bacillales, Bacteroidales, Bifidobacteriales, Burkholderiales, Cam pylobacterales, Caulobacterales, Cardiobacteriales, Clostridiales, Enterobacteriales, Flavobacteriales, Fusobacteriales, Lactobacillales, Micrococcales, Neisseriales, Pasteurellales, Pseudomonadales, Rhizobiales, Rhodospirillales, Selenomonadales, Vibrionales and/or Xanthomonadales.

The bacteria may optionally be selected from the Family Acetobacteraceae, Alcaligenaceae, Bacillaceae, Bacteroidaceae, Burkholderiaceae, Caulobacteraceae, Comamonadaceae, Enterobacteriaceae, Flavobacteriaceae, Fusobacteriaceae Nocardiaceae, Prevotellaceae, Porphyromonadaceae, Pseudomonadaceae, Rikenellaceae, Rhizobiaceae and/or Sutterellaceae.

The bacteria may optionally be of a genus selected from, e.g., *Abiotrophia, Achromobacter, Acidovorax, Acinetobacter, Actinobacillus, Actinomadura, Actinomyces, Aerococcus, Aeromonas, Anaerococcus, Anaplasma, Bacillus, Bacteroides, Bartonella, Bifidobacterium, Bordetella, Borrelia, Brevundimonas, Brucella, Burkholderia Campylobacter, Capnocytophaga, Chlamydia, Citrobacter, Chlamydophila, Chryseobacterium, Clostridium, Comamonas, Corynebacterium, Coxiella, Cupriavidus, Delftia, Dermabacter, Ehrlichia, Eikenella, Enterobacter, Enterococcus, Escherichia, Erysipelothrix, Facklamia, Finegoldia, Francisella, Fusobacterium, Gemella, Gordonia, Haemophilus, Helicobacter, Klebsiella, Lactobacillus, Legionella, Leptospira, Listeria, Micrococcus, Moraxella, Morganella, Mycobacterium, Mycoplasma, Neisseria, Nocardia, Orientia, Pandoraea, Pasteurella, Peptoniphilus, Peptostreptococcus, Plesiomonas, Porphyromonas, Pseudomonas, Prevotella, Proteus, Propionibacterium, Rhodococcus, Ralstonia, Raoultella, Rickettsia, Rothia, Salmonella, Serratia, Shigella, Staphylococcus, Stenotrophomonas, Streptococcus, Tannerella, Treponema, Ureaplasma, Vibrio* and/or *Yersinia*.

The bacteria may optionally be of a species selected from, e.g., *Abiotrophia defective, Achromobacter xylosoxidans, Acidovorax avenae, Acidovorax citrulli, Akkermansia muciniphila, Bacillus anthracis, B. cereus, B. subtilis, B. licheniformis, Bacteroides fragilis, Bartonella henselae, Bartonella*

*quintana, Bordetella pertussis, Borrelia burgdorferi, Borrelia garinii Borrelia afzelii, Borrelia recurrentis, Brucella abortus, Brucella canis, Brucella melitensis, Brucella suis, Burkholderia cepacia, Burkholderia genomovars, Campylobacter jejuni, Chlamydia pneumoniae, Chlamydia trachomatis, Chlamydophila psittaci, Citrobacter koseri, Clostridium botulinum, Clostridium difficile, C. perfringens, C. tetani, Corynebacterium diphtheriae, C. striatum, C. minutissimum, C. imitans, C. amycolatum, Delftia acidovorans, Enterobacter aerogenes, E. cloacae Enterococcus faecalis, Enterococcus faecium, Escherichia coli, Francisella tularensis, Fusobacterium nucleatum, Haemophilus influenzae, Helicobacter pylori, Klebsiella oxytoca, K. pneumonia, Legionella pneumophila, Leptospira interrogans, Leptospira santarosai, Leptospira weilii, Leptospira noguchii, Listeria ivanovii, Listeria monocytogenes, Micrococcus luteus, Morganella morganii, Moraxella catarrhalis, Mycobacterium avium, M. fortuitum, M. leprae, M. peregrium, M. tuberculosis, M. ulcerans, Mycoplasma pneumoniae, Neisseria gonorrhoeae, N. lactamica, N. meningitidis, Nocardia asteroids, Proteus mirabilis, Pseudomonas aeruginosa, Rhodococcus equi, Rhodococcus pyridinivorans, Rickettsia rickettsii, Salmonella typhi, Salmonella typhimurium, Serratia marcescens, Shigella sonnei, Staphylococcus aureus, S. capitis, S. epidermidis, S. haemolyticus, S. hominis, S. saprophyticus, Stenotrophomonas maltophilia, Streptococcus agalactiae, S. pyogenes, S. pneumonia, Treponema pallidum, Ureaplasma urealyticum, Vibrio cholerae, Yersinia pestis, Yersinia enterocolitica* and *Yersinia pseudotuberculosis.*

The virus may optionally be a DNA virus, and RNA virus or a retrovirus. It may optionally be a single stranded (ss) or a double stranded (ds) virus. More particularly, it may optionally be a ssDNA, dsDNA, dsRNA, ssRNA (positive strand), ssRNA (negative strand), ssRNA (reverse transcribed) or dsDNA (reverse transcribed) virus.

It may optionally be selected from one or more of the Herpesviridae, optionally selected from Simplexvirus, Varicellovirus, Cytomegalovirus, Roseolovirus, Lymphocryptovirus, and/or Rhadinovirus; the Adenoviridae, optionally selected from Adenovirus and/or Mastadenovirus; Papillomaviridae, optionally selected from Alphapapillomavirus, Betapapillomavirus, Gammapapilloma-virus, Mupapillomavirus, and/or Nupapillomavirus; Polyomaviridae, optionally selected from Polyomavirus; Poxviridae, optionally selected from Molluscipoxvirus, Orthopoxvirus and/or Parapoxvirus; Anelloviridae, optionally selected from Alphatorquevirus, Betatorquevirus, and/or Gammatorquevirus; Mycodnaviridae, optionally selected from Gemycircular-viruses; Parvoviridae, optionally selected from Erythrovirus, Dependovirus, and/or Bocavirus; Reoviridae, optionally selected from Coltivirus, Rotavirus, and/or Seadornavirus; Coronaviridae, optionally selected from Alphacoronavirus, Betacoronavirus, and/or Torovirus; Astroviridae, optionally selected from Mamastrovirus; Caliciviridae, optionally selected from Norovirus, and/or Sapovirus; Flaviviridae, optionally selected from Flavivirus, Hepacivirus, and/or Pegivirus; Picornaviridae, optionally selected from Cardiovirus, Cosavirus, Enterovirus, Hepatovirus, Kobuvirus, Parechovirus, Rosavirus, and/or Salivirus; Togaviridae, optionally selected from Alphavirus and/or Rubivirus; Rhabdoviridae, optionally selected from Lyssavirus, and/or Vesiculovirus; Filoviridae optionally selected from Ebolavirus, and/or Marburgvirus; Paramyxoviridae, optionally selected from Henipavirus, Heffalumpvirus, Morbilivirus, Respirovirus, Rubulavirus, Metapneumovirus, and/or Pneumovirus; Arenaviridae, optionally selected from Arenavirus; Bunyaviridae, optionally selected from Hantavirus, Nairovirus, Orthobunyavirus, and/or Phlebovirus; Orthomyxoviridae, optionally selected from Influenzavirus A, Influenzavirus B, Influenzavirus C and/or Thogotovirus; Retroviridae, optionally selected from Gammaretrovirus, Deltaretrovirus, Lentivirus, Spumavirus; Epadnaviridae, optionally selected from Orthohepadnavirus; Hepevirus; and/or Deltavirus.

The microbes may optionally be pathogenic or non-pathogenic. A pathogenic microbe, which may also be called a "pathogen", may be defined as a microbe that is able to cause disease in a host, such as a plant or animal. A pathogen may optionally be an obligate pathogen or an opportunistic pathogen.

The ability of a microbe to cause disease depends both on its intrinsic virulence factors and on the ability of the host to fight off the microbe. The distinction between non-pathogens and opportunistic pathogens is therefore not clear-cut, because, for example, immuno-compromised hosts will be susceptible to infection by microbes that may be unable to infect a host with a healthy immune system.

For example, *Neisseria gonorrhoeae* is an obligate pathogen, *Pseudomonas aeruginosa* and *Candida albicans* are typically referred to as opportunistic pathogens, and *Lactobacillus acidophilus* and *Bifidobacterium bifidum* are typically considered to be non-pathogens, and may be referred to as "commensal".

Drugs, such as, an antimicrobial and/or an anti-inflammatory drug, may also create an environment in which a microbe will flourish as an opportunistic pathogen. Thus, the use of drugs may alter a microbiome. The method may therefore optionally involve analysing the microbiome, e.g., the mucosal microbiome, to analyse the response to a drug.

Pathogenic microbes may optionally be characterised by the expression of one or more virulence factors, i.e. factors that allow or facilitate infection of a host. Virulence factors may optionally be selected from factors that mediate cell adherence, cell growth, the ability to bypass or overcome host defence mechanisms, and/or the production of toxins. Toxins may be selected from exotoxins and endotoxins. The method may optionally involve analysing one or more virulence factors.

Commensal microbes are those which are part of the natural flora of a human or animal and which, in a balanced state, do not cause disease.

The community of microbes in a particular environment may be referred to as a "microbiome". A microbiome may be a complex mixture of a vast number and vast variety of different microbes. The gastrointestinal (GI) microbiome is estimated to comprise over 100 trillion microbes that represent at least several hundreds or even over a thousand different species. The healthy human gut microbiota is dominated by the Bacteroidetes and the Firmicutes, whereas, for example, Proteobacteria, Verrucomicrobia, Actinobacteria, Fusobacteria, and Cyanobacteria are typically present in minor proportions.

The microbiome may vary from one environment to another within the same human or animal, so a person's gastrointestinal (GI) microbiome may be different from that person's nasal microbiome. The GI microbiome may further be divided into the different GI regions, such as, stomach, duodenum, jejunum, ileum, and/or colon. The lumen microbiome may also differ from the mucosal microbiome. Each microbiome may also vary from one individual to another. The disturbance of the normal microbiome may be referred to as "dysbiosis". Dysbiosis may cause, or be associated with, a disease, such as, any of the diseases mentioned herein. The method may optionally involve the analysis of a microbiome to analyse dysbiosis. The GI microbiome may also be referred to as the "gut flora".

The microbiome may change during pregnancy, so an analysis of the female (human or animal) microbiome may allow an analysis of pregnancy. Dysbiosis in pregnancy is associated with complications, such as, an increased risk of premature birth.

Dysbiosis may involve the presence of one or more types of microbes that are normally, or were previously, absent from a particular microbiome. However, more commonly, dysbiosis may involve a relative increase in the proportion of one or more particular microbes, and/or a relative decrease in the proportion of one or more particular microbes.

As mentioned above, the mucosa comprises layers of mucus. Microbes, such as bacteria, may adhere to and/or partially or fully infiltrate the mucus layer. The microbial adherence and/or proliferation may be influenced by carbohydrate modifications present on mucins; by antimicrobial agents, such as, host-derived antimicrobial peptides; by drugs; by diet; and/or by toxins, such as, toxins produced by (pathogenic) microbes.

The mucosal (epithelial) surface beneath the mucus layer is free of microbes in at least about 80% of healthy humans. The thickness of the mucus layer and its spread may vary, for example, they may decrease with increasing severity of inflammation. Under certain conditions, for example, in a disease, microbes may infiltrate and/or adhere to the mucus layer, the epithelium and/or the LP. For example, bacteria may typically be found within the mucus of biopsy specimens from subjects with ulcerative colitis, SLC, and/or acute appendicitis. The concentration of microbes within the mucus layer may inversely correlate to the numbers of leucocytes.

The term "mucosal microbiome" is used herein to denote the microbiome which is associated with the mucosa, including the microbiome that has infiltrated the mucosa and the microbiome that is associated with (for example, through adhesion or partial or full infiltration) with the mucus layer.

The method may optionally involve the analysis of an infection, e.g., the diagnosis of an infection, analysis of the genotype or phenotype of the infection-causing microbe, monitoring of progression of infection, and/or monitoring of treatment response to infection.

The method may optionally involve the analysis of vaccination. This may, e.g., involve analysing a target prior to and after vaccination. Optionally, the subject may be challenged after vaccination with the microbe against which the vaccination is aimed, and a suitable target may then be analysed to determine whether, or at what level, the microbe is present. The presence or level of the microbe may be indicative of the success of vaccination, e.g., the absence or presence at low levels of the microbe may be indicative of successful vaccination, whereas the presence, or presence at high levels of the microbe may be indicative of the vaccine being deficient or ineffective.

The mucosal membrane may be considered to be a protective layer responsible for trapping pathogens in the human body.

The mucosa lines several passages and cavities of the body, particularly those with openings exposed to the external environment, including the oral-pharyngeal cavity, gastrointestinal (GI) tract, respiratory tract, urogenital tract, and exocrine glands. Thus, the mucosa may optionally be selected from Bronchial mucosa, Endometrium (mucosa of the uterus), Esophageal mucosa, Gastric mucosa, Intestinal mucosa (gut mucosa), Nasal mucosa, Olfactory mucosa, Oral mucosa, Penile mucosa and/or Vaginal mucosa.

Broadly speaking, the mucosa comprises a mucus layer (the inner mucus layer); an epithelium; a basement membrane, a Lamina propria (LP), which is a layer of connective tissue; and a Muscularis mucosae, which is a thin layer of smooth muscle. Thus, the term "mucosa" is used herein to refer to this entire complex, unless stated otherwise and the term "mucosal membrane" is used interchangeably with the term "mucosa". The mucosa may also be covered by a further, outer mucus layer, which is typically more loosely associated therewith. Any reference herein to a "mucosa" may include reference to this further, outer mucus layer. Adjacent to the mucosa is the submucosa.

The inner mucus layer may be degraded by microbes. For example, mucin monosaccharides may be used by bacteria, e.g., commensal bacteria, as an energy source. Therefore, continuous renewal of the inner mucus layer is very important.

The epithelium is a single or multiple layer(s) of epithelial cells. The epithelium may comprise, for example, intra-epithelial lymphocytes (IELs), endocrine cells, goblet cells, enterocytes and/or Paneth cells.

The basement membrane may comprise various proteins, particularly structural or adhesive proteins, such as, laminins, collagens, e.g., collagen IV, proteoglycans, and/or calcium binding proteins such as fibulin.

The Lamina propria is connective tissue which may comprise, for example, plasma cells, eosinophils, histiocytes, mast cells and/or lymphocytes. Neutrophils are generally absent in the Lamina propria of healthy humans.

As discussed below, the mucosa may also comprise, for example, antigen presenting cells (APCs) and microfold cells (M-cells). The mucosa may include one or more distinct types of regulatory immune cells, including intestinal intraepithelial lymphocytes (IELs), Foxp3(+) regulatory T cells, regulatory B cells, alternatively activated macrophages, dendritic cells, and/or innate lymphoid cells.

The mucosa typically secretes mucus, which forms a mucus layer between the mucosal epithelium and the lumen. The mucus layer may have a protective function. A major constituent of mucus are mucins, which are produced by specialized mucosal cells called goblet cells. Mucins are glycoproteins characterized mainly by a high level of O-linked oligosaccharides. The level to which the protein moiety is linked to the carbohydrate moieties, as well as the precise identity of the charbohydrate moieties, may vary significantly.

Mucosa establish a barrier between sometimes hostile external environments and the internal milieu. However, mucosae are also responsible for nutrient absorption and waste secretion, which require a selectively permeable barrier. These functions place the mucosal epithelium at the centre of interactions between the mucosal immune system and luminal contents, including dietary antigens and microbial products. Thus, many physiological and immunological stimuli trigger responses in the mucosa. Dysfunctional responses may contribute to disease.

The mucosal immune system is a localized and specific immune organisation. The mucosal immune system at different organs share similar anatomical organization and features. The GI mucosal immune system is best understood, and is discussed below for illustrative purposes. The GI mucosal immune system is composed of three major compartments: the epithelial layer; the lamina propria (LP); and the mucosal-associated lymphoid tissue (MALT), which, in the GI tract, may be referred to as gut-associated lymphoid tissue, and which comprises Peyer's patches and isolated lymphoid follicles.

Dendritic cells may project dendrites into the epithelium to uptake antigens and migrate to the LP, secondary lymphoid tissue and draining lymph nodes, where they prime naive T cells. Microfold cells (M-cells), located in the epithelium of Peyer's patches, may pass the antigens to dendritic cells, macrophages and other antigen presenting cells. Naive T cells in secondary lymphoid tissues may become activated after being primed by antigen presenting cell and home to LP (called LPLs) or infiltrate into inflamed epithelium.

The gastrointestinal (GI) tract can be divided into four concentric layers that surround the lumen in the following order: (i) Mucosa; (ii) Submucosa; (iii) Muscular layer; and (iv) Adventitia or serosa.

Thus, the GI mucosa is the innermost layer of the gastrointestinal tract. This layer comes in direct contact with digested food. In the GI mucosa, the epithelium is responsible for most digestive, absorptive and secretory processes, whereas the Muscularis mucosae aids the passing of material and enhances the interaction between the epithelial layer and the contents of the lumen by agitation and peristalsis.

GI mucosae are highly specialized in each organ of the GI tract to deal with the different conditions. The most variation may occur in the epithelium.

Different types of mucosa differ from one another and the inventors have shown that the method of the various embodiments described herein may optionally be used, e.g., to distinguish between different types of mucosa, e.g. vaginal, nasal and oral.

Figure 2:
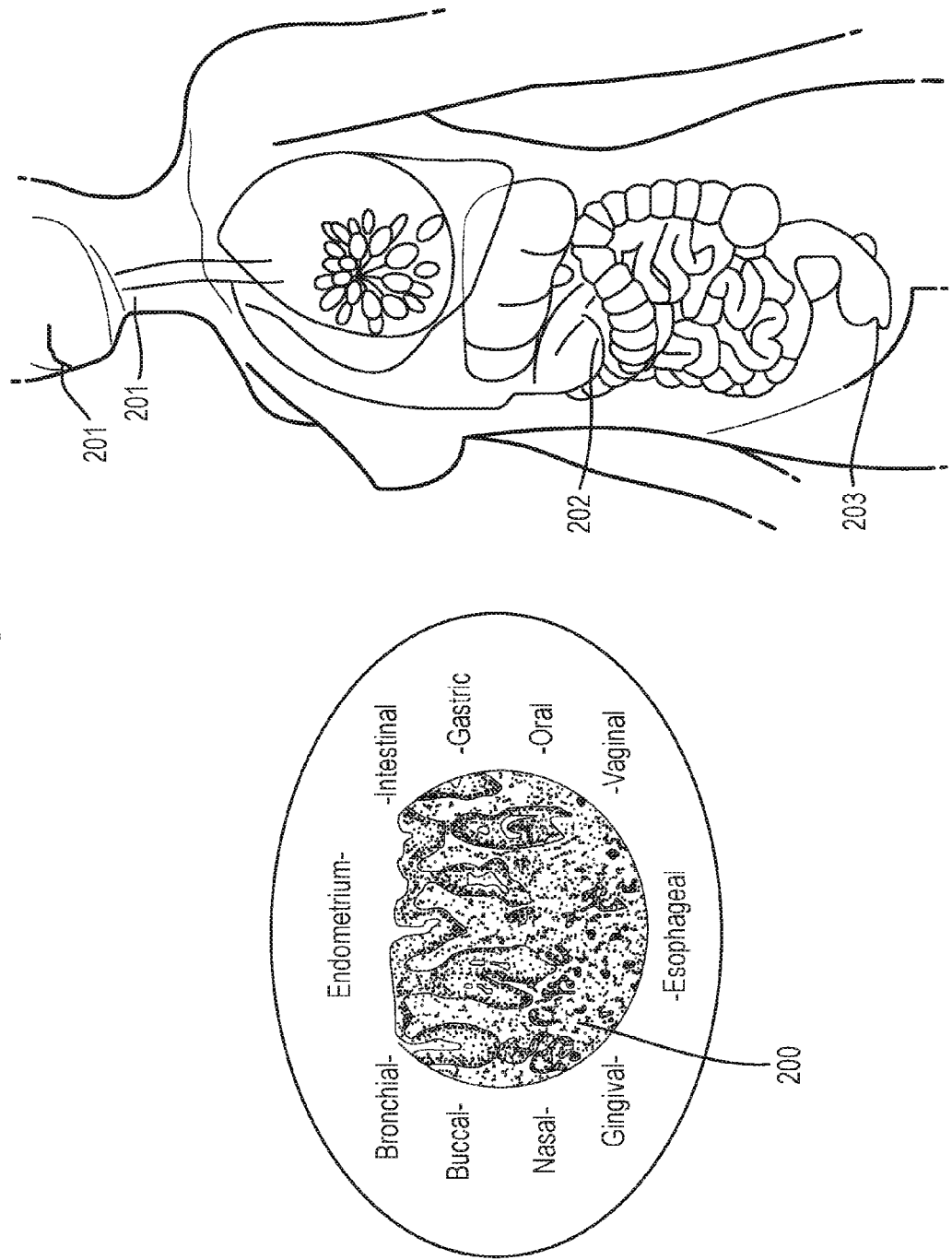
FIG. 2 shows schematically various mucosa or mucosal membranes which are present in the human body.

FIG. 2 illustrates various different mucosa or mucosal membranes which are present in the human body.

Mucosal membranes 200 comprise a layer of epithelial tissue which lines all passages in the human body that are open to the external environments including the nose and parts of the digestive, urogenital and respiratory tracts. Mucosal membranes typically act as a protective barrier to trap pathogens such as bacteria, viruses and fungi. For example, the mucosae of oral, respiratory and urogenital tracts are composed of epithelial tissue and underlying lamina that are directly exposed to the external environment, making them a primary site of innate and acquired protection against host infection.

As shown in FIG. 2, mucosal membranes are present in the mouth, pharynx, and respiratory system 201, as well as in the gastro-intestinal tract 202 and the urogenital tract 203, and include the endometrium, intestinal, gastric, oral, vaginal, esophageal, gingival, nasal, buccal and bronchial membranes.

Studies as part of the human microbiome project have revealed that colonization by different microbial species within the mucosa has an immense impact upon human health and disease. As discussed elsewhere herein, many diseases (e.g. cancer, infections, etc.) are associated with the mucosa. Host-microbiota interactions at mucosal surfaces have an important impact not only on pathology and disease, but also on health states. For example, commensal vaginal microbiota excrete antimicrobial compounds and metabolites into the cervicovaginal mucosa that modulates both its physical and immunological properties. During pregnancy, this mechanism is thought to provide protection against pathobiont colonisation of the reproductive tract, which is a major cause of preterm birth. Nasal mucosal surfaces are key modulators of allergic inflammation and airway obstruction pathologies such as asthma.

As such, the mucosal membrane is an easily accessible and highly clinically relevant sample to analyse, e.g., to diagnose diseases, e.g., microbial and/or cancerous associated diseases, etc., and mucosal diagnostics represents an important field that has wide clinical applications.

As shown in FIG. 3, a typical mucosal membrane may be present in a lumen 300 and may include mucus 301, bacteria 302, lymphatic vessels 303, blood vessels 304, mucosal glands 305, and submucosa 306. As illustrated by FIG. 3, the biological tissue of the mucosa itself, e.g. mucus 301, and/or bacteria 302 present in or associated with the mucosa represent potential analytes/biomarkers. For example, membrane lipids, and/or inflammatory markers of the mucosa, and/or complex lipids and/or signalling molecules of intact bacteria cells represent potential analytes/biomarkers.

The method according to various embodiments may involve the analysis of a mucosal target, e.g., on a swab or biopsy. Optionally, the method may involve the analysis of a mucosal target to analyse the cellular composition of the mucosa; to analyse a disease; to analyse the response to a drug; to analyse the response to a particular food, diet, and/or a change in diet; to analyse a mucosal microbe; to analyse a microbial interaction with the mucosa; and/or to analyse the mucosal microbiome.

The analysis of the cellular composition of a mucosa, may, e.g., analyse the presence or absence and/or proportion of one or more cell types, which may optionally be selected from any of the cell types listed herein. Optionally, the method may involve the analysis of MALT and/or a Peyer's patch. Optionally, the method may involve the analysis of the phenotype and/or genotype of one or more cell types, which may optionally be selected from any of the cell types listed herein.

Optionally, the method may involve the analysis of a change in the mucosa, which may optionally be a change in, e.g., the cellular composition of the mucosa, the microbial interaction(s) with the mucosa, and/or the mucosal microbiome. By a "change" in the mucosa is meant that the mucosa is different from how it would typically present in a healthy subject; that it is different in one location compared to another location within the same subject; and/or that it is different from how it was when it was analysed at an earlier point in time. A change in the mucosa may optionally, for example, be caused by, or associated with, a disease, the response to a substance, such as a drug, and/or the response to a food, diet, and/or diet change.

A disease may optionally be selected from an autoimmune disorder, an inflammatory disease, tropical sprue, a food intolerance, an infection, a cancer, and/or any of the of the disorders mentioned herein.

More particularly, the disease may optionally be selected from, for example, asthma, Coeliac disease, gastritis, peptic duodenitis, Gluten-sensitive enteropathy; allergy and/or intolerance to an allergen, e.g. to milk, soy, tree nut(s), egg, wheat, meat, fish, shellfish, peanut, seed, such as sesame, sunflower, and/or poppy seeds, garlic, mustard, coriander, and/or onion; Hashimoto's thyroiditis; Irritable bowel syndrome; Graves's disease; reactive arthritis; psoriasis; multiple sclerosis; Systemic lupus erythematosus (SLE or lupus); ankylosing spondylitis; progressive systemic sclerosis (PSS); glomerulonephritis; autoimmune enteropathy; IgA deficiency; common variable immunodeficiency; Crohn's disease; colitis, such as, lymphocytic colitis, collagenous colitis and/or ulcerative colitis; diffuse lymphocytic gastroenteritis; ulcer; intestinal T-cell lymphoma; infection, e.g., pharyngitis, bronchitis, and/or infection with a microbe selected, for example, from Giardia, *Cryptospo-*

*ridium, Helicobacter* and/or any of the other microbes mentioned herein; and/or cancer, details of which are discussed elsewhere herein.

The method may, e.g., optionally involve the analysis of the interaction of the mucosa with microbes, or a change in the mucosa caused by, or associated with, such an interaction. Optionally, the interaction may, e.g., be the translocation of microbes into the mucosa, e.g., the translocation of commensal bacteria. The method may, e.g., optionally involve the analysis of the mucosal microbiome, or a change in the mucosa caused by, or associated with, the mucosal microbiome. The method may, e.g., optionally involve the analysis of an infection, or a change in the mucosa caused by, or associated with, an infection. The analysis of microbes, a microbial interaction, infections and/or the microbiome are also discussed elsewhere herein.

As mentioned above, IELs are a normal constituent of the small intestinal mucosa. They play a significant role in immune surveillance and activation. In healthy humans, the vast majority of IELs are of T-cell type and express an $\alpha/\beta$ T-cell receptor on their surface. It is generally accepted that healthy humans have no more than about 20 lymphocytes per 100 epithelial cells in the intestinal mucosa.

An increased number of lymphocytes in a mucosal specimen may optionally be indicative of a change, such as, a disease, the response to a drug, and/or a microbial change. The term "elevated" or "increased" levels of IELs is therefore used to refer to more than 20 IELs per 100 epithelial cells in the intestinal mucosa, optionally at least 22, 24, 25, 26, 28, 30, 32, 34, 36, 38, 40, 42, 44, 46, 48, 50, 52, 54, 56, 58, 60, 65, 70, 75 or 80 IELs per 100 epithelial cells in the intestinal mucosa.

The gamma-delta receptor of T lymphocytes is not expressed by more than 2-3% of T lymphocytes in normal conditions. An increase in the percentage of T lymphocytes expressing this receptor may therefore be indicative of a change, such as, a disease, the response to a drug, and/or a microbial change. The method may therefore involve determining the presence or percentage of T lymphocyte gamma-delta receptor expression. For example, in coeliac disease 20-30% of mucosal T lymphocytes may express this receptor.

Thus, the method may optionally involve the analysis of lymphocytes in a target, which may optionally be T lymphocytes, e.g. gamma-delta receptor-positive T lymphocytes. Optionally, a target may be analysed for an increase or decrease in the number of lymphocytes. Optionally, the phenotype and/or genotype of the lymphocytes may be analysed.

Polymorphonuclear leukocytes (PMN), also called neutrophils, are the most abundant leukocyte population in the blood, comprising 50-60% of the circulating leukocytes (25×109 cells). PMN are critical components of the innate immune response that are essential in protecting the host, e.g., from microbial pathogens, while also minimizing deleterious effects mediated by dying or injured cells.

PMN may perform a variety of antimicrobial functions such as degranulation and phagocytosis. They are uniquely capable of forming large amounts of reactive oxygen species and other toxic molecules that may weaken and/or destroy pathogens. Upon PMN contact with invading microbes, reactive oxygen species may be generated in an oxidative burst by an nicotinamide adenine dinucleotide phosphate (NADPH) oxidase PMN may also possess different pools of intracellular granules that contain antimicrobial peptides, such as, $\alpha$-defensins and/or cathelicidins; myeloperoxidase; hydrolytic enzymes, such as, lysozyme, sialidase, and/or collagenase; proteases, such as, cathepsin G; azurocidin, and/or elastase; cationic phospholipase; and/or metal chelators such as lactoferrin. Such granules may be released upon contact with microbes.

PMN may also be capable of imprinting the tissue with neutrophil extracellular traps (NETs). NETs may be composed of nuclear contents (DNA and chromatin) mixed with toxic molecules from intracellular granules and the cytosol. Invading microorganisms may be sequestered in these NETs and effectively destroyed.

During intestinal inflammation, resident monocytes contribute to the recruitment of neutrophils through production of macrophage-derived chemokines. Neutrophils present in the blood sense the chemoattractant gradient and traverse the vascular endothelium to reach the intestinal lamina propria. In this manner, neutrophils are recruited to sites of infection or inflammatory stimuli within minutes. The response typically peaks by 24-48 hours. Under certain physiological or pathological conditions, neutrophils may cross the epithelium into the intestinal lumen.

At inflammatory sites, neutrophils may selectively release monocyte chemoattractants, such as CAP18, cathepsin G, and/or azurocidin. Thus, shortly after arrival of PMN to the mucosa, macrophages are recruited for a second-wave inflammatory response that ensues for the next several days.

Thus, the method may optionally involve the analysis of neutrophils in a target. Optionally, the presence of reactive oxygen species and/or neutrophils generating reactive oxygen species in a target may be analysed. Optionally, the presence of NETs and/or neutrophils generating NETs in a target may be analysed. Optionally, the presence of monocyte chemoattractants and/or neutrophils generating monocyte chemoattractants in a target may be analysed.

According to various embodiments, microbial, e.g., bacterial, and/or animal, e.g., human mucosal membrane analytes may be characterised, e.g. using ambient mass spectrometry based techniques such as the desorption electrospray ionisation ("DESI") technique and the rapid evaporative ionisation mass spectrometry ("REIMS") technique.

As illustrated by FIG. 4, these analytes (e.g., membrane lipids and inflammatory markers of the mucosa, and complex lipids and signalling molecules of intact bacteria cells) can be useful in identifying a number of clinical disorders.

Accordingly, various embodiments are directed to the development of a real time point of care ("POC") diagnostic method to investigate various clinical disorders. In particular, various embodiments are directed to mass spectrometry ("MS") based real-time point of care ("POC") techniques.

For example, infections such as pharyngitis, bronchitis, and/or infections with any of the microbes mentioned herein etc. can be identified e.g. by analysing, e.g., identifying microbes.

Changes in the microbiome can also be analysed, e.g., detected, e.g., by identifying microbes, and by way of example, determining a change in the microbiome of a pregnant patient can be used to identify those patients who are at an increased risk of having a pre-term or premature delivery during pregnancy.

Furthermore, the various analytes taken from mucosal membranes, e.g. biomarker profiling, can be used to identify various immunological disorders (e.g., asthma, allergies) as well as to identify cancer and pre-cancerous states.

Figure 5:
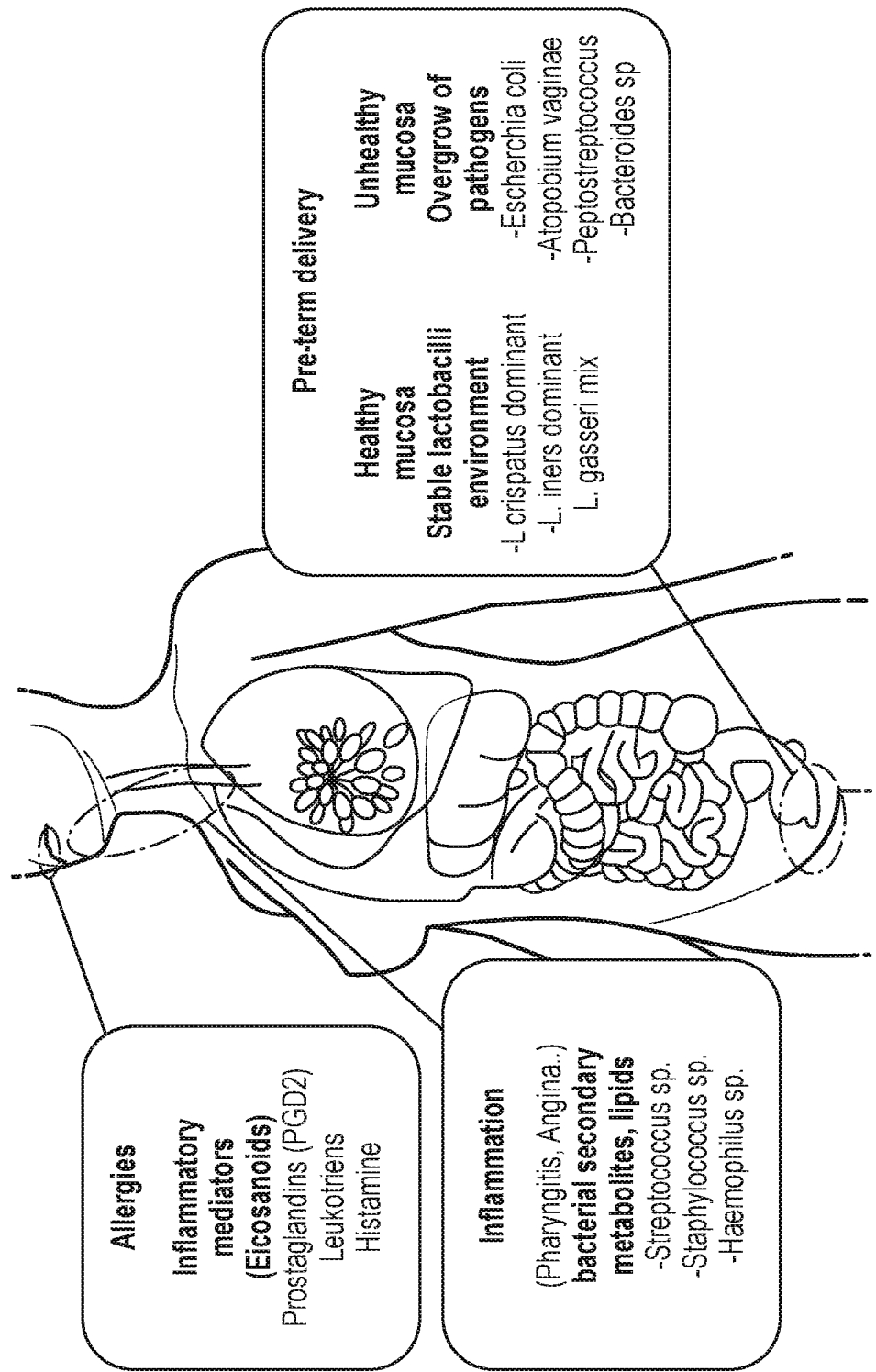
FIG. 5 shows schematically how metabolomic profiling of analytes from a mucosal membrane can be useful in identifying clinical disorders such as allergies, inflammation and pre-term delivery.

As further illustrated by FIG. 5, metabolomic profiling of analytes from various mucosal membranes using swabs can be useful in identifying a number of clinical disorders. For example, allergies may be identified, e.g., by identifying inflammatory mediators (eicosanoids) such as prostaglandins (PGD2), leukotriends, histamine, etc. Inflammation (such as pharyngitis, angina, etc.) may be identified, e.g., by identifying microbial, e.g., bacterial secondary metabolites, lipids, etc. from bacteria such as *streptococcus* sp., *staphylococcus* sp., *haemophilus* sp., etc. Pre-term delivery may also be identified, e.g. by identifying healthy (e.g. comprising a stable lactobacilli environment including e.g., *L. crispatus* dominant, *L. iners* dominant, and/or *L. gasseri* mix, etc.) or unhealthy mucosa (e.g. comprising an overgrowth of pathogens including, e.g., *Escherchia coli, Atopobium vaginae, Peptostreptococcus,* and/or *Bacteroides* sp., etc.).

According to various embodiments, mucosal diagnostics enable non-invasive direct sampling of the mucosa from patients at a clinical point of care.

According to various embodiments, analytes may be obtained from mucosal membranes using, e.g., a "standard medical swab", i.e., a standard collection or sampling device for mucosa that can be used in clinical microbiology (e.g. to take microbiological cultures), gene and drug testing, etc. The "standard medical swab" may comprise, for example, a pad of cotton, i.e. the standard sample collecting device for mucosa. As will be discussed in more detail below, the medical swab may be wetted or otherwise functionalised.

For clinical analysis, the swabs may be wiped over or into an infected area, e.g. to sample microbe rich body fluid, such as, sanies, and/or the mucosa itself. For conventional microbial analysis, the swab may then be placed into a sterile tube which may contain a buffer solution or transport media for storage before the tube is sent to a laboratory for analysis such as microscopy and/or culture-based characterisation of the microbial content. For example, a laboratory receiving the tube may wipe the smear content across a culture medium such as an agar plate. The culture medium may then be incubated to allow organisms present to grow. Microbial identification may then be performed under a microscope. Any organisms present in the sample may also be identified, e.g., by sequence analysis, e.g., 16S gene-sequencing of bacteria, and/or by using matrix-assisted laser desorption ionisation ("MALDI") mass spectrometry and then comparing the mass spectra with a commercially available database.

FIG. 6 illustrates a microbe identification workflow and shows sampling 601 an analyte using a swab and then transporting 602 the swab to a specialist laboratory for microbe culturing 603 and further analysis. As shown in FIG. 6, such culture based analysis may comprise imaging using a microscope 604 and/or Matrix Assisted Laser Desorption Ionisation ("MALDI") Mass Spectrometry ("MS") 605 followed by statistical analysis 606, etc. 16s rRNA sequencing 607 is a culture independent analysis method.

Although easy to handle, the current analysis of medical swabs for diagnostic purposes is culture-dependent and involves a relatively time consuming and relatively costly workflow. Diagnosis of pathogen-associated diseases and appropriate treatment is therefore associated with considerable delay. Furthermore, around 95% of bacteria cannot be cultured for analysis. As such, conventional methods are limited by their qualitative nature, time required to obtain results and inability to assess host response to the presence or absence of specific microbiota.

Sequencing of bacterial 16S rRNA gene or analysis of samples by matrix-assisted laser desorption ionization (MALDI) mass spectrometry (MS) are also time consuming and costly.

Various embodiments which are described in more detail below provide a fast and direct way to investigate clinical samples from mucosal membranes, e.g. by identifying microbes and/or biomarkers characteristic of specific clinical disorders in mucosal samples, thereby permitting faster diagnoses and treatment of patients.

Various embodiments are directed to real time rapid and direct analysis of analytes present on a swab using ambient mass spectrometry. Ambient ionisation mass spectrometry based techniques may be employed for direct analysis of the sample surface. A sample may be analysed in its native state with minimal or no prior sample preparation.

Various embodiments permit rapid acquisition of detailed mass spectral metabolic fingerprints from a wide variety of biological materials, including intact bacteria, without the need of extraction or extensive sample preparation protocols.

In particular, Desorption Electrospray Ionisation ("DESI") has been found to be a particularly useful and convenient method for the real time rapid and direct analysis of analytes present on a swab. Desorption electrospray ionisation ("DESI") allows direct and fast analysis of surfaces without the need for prior sample preparation. The technique will now be described in more detail with reference to FIG. 7.

As shown in FIG. 7, the desorption electrospray ionisation ("DESI") technique is an ambient ionisation method that involves directing a spray of (primary) electrically charged droplets 701 onto a surface 702 with analyte 703 present on the surface 702 and/or directly onto a surface of a sample 704. The electrospray mist is pneumatically directed at the sample by a sprayer 700 where subsequent splashed (secondary) droplets 705 carry desorbed ionised analytes (e.g. desorbed lipid ions). The sprayer 700 may be supplied with a solvent 706, gas 707 such as nitrogen, and voltage from a high voltage ("HV") source 708. After ionisation, the ions travel through air into an atmospheric pressure interface 709 of a mass and/or ion mobility spectrometer or mass analyser (not shown), e.g. via a transfer capillary 710.

The desorption electrospray ionisation ("DESI") technique allows for ambient ionisation of a trace sample at atmospheric pressure with little sample preparation. The desorption electrospray ionisation ("DESI") technique allows, for example, direct analysis of biological compounds such as lipids, metabolites and peptides in their native state without requiring any advance sample preparation.

Embodiments described herein relate to directly analysing medical swabs using desorption electrospray ionisation ("DESI") mass spectrometry. According to various embodiments chemical signature identification of specific microbes, e.g., bacteria and/or biomarkers on the surface of the swabs is possible within a relatively short period of time.

Various specific embodiments relate to the rapid diagnosis of infections and/or dysbiosis, e.g., associated with preterm (premature) delivery (and these results may optionally be compared with standard microbial testing).

Further embodiments relate to a real-time rapid medical swab analysis using desorption electrospray ionisation ("DESI") mass spectrometry to reveal pathogenic and/or inflammatory metabolomic markers.

Furthermore, various chemically modified swabs for use with desorption electrospray ionisation ("DESI") mass spectrometry are disclosed. These have been found to exhibit an improved sensitivity compared with conventional (non-modified) swabs.

It has also been found that a significant enhancement in signal intensity can be obtained by rotating or continuously rotating a swab whilst analysing the swab using the desorption electrospray ionisation ("DESI") technique.

Desorption electrospray ionisation ("DESI") mass spectrometry analysis of medical swabs is relatively simple, e.g. compared to liquid extraction based mass spectrometry techniques including high performance liquid chromatography ("HPLC") mass spectrometry, as no sample preparation steps are required prior to analysis and ionisation occurs directly from the (rotatable) medical swab. Desorption electrospray ionisation ("DESI") mass spectrometry analysis of medical swabs is also an improvement over to so-called "touch spray" ("TS") mass spectrometry, which is limited in terms of the reproducibility of and control over the spray formation and spray stability due to strong evaporation and drying of swabs.

Figure 8B:
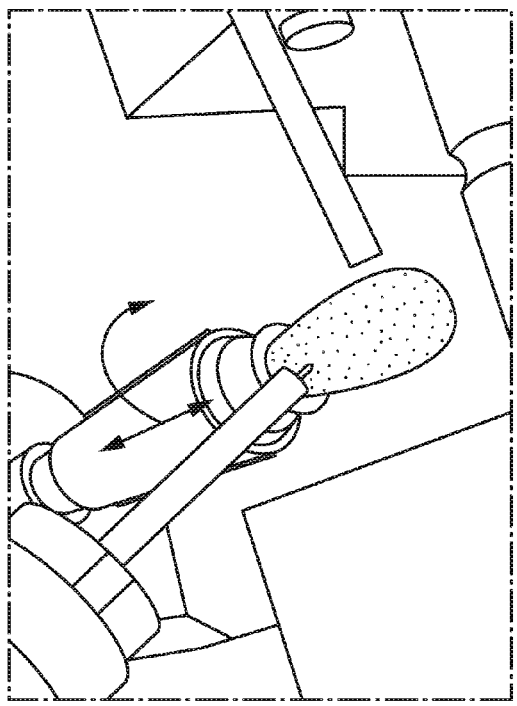
FIG. 8 shows schematically a desorption electrospray ionisation ("DESI") mass spectrometry setup for swab analysis according to various embodiments.
Figure 8A:
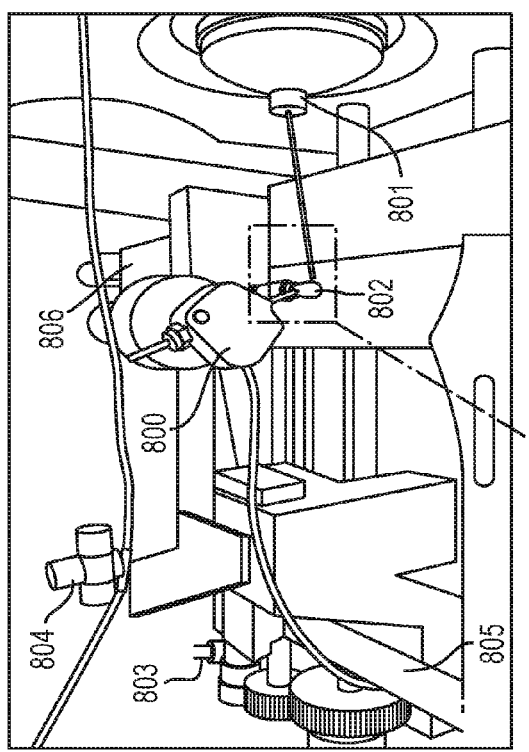
Figure 8C:
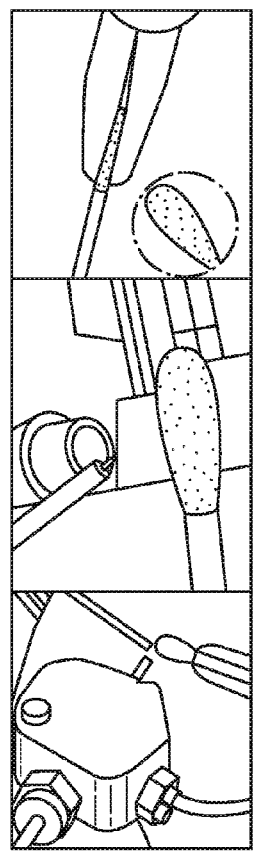

FIGS. 8A-C illustrate a desorption electrospray ionisation ("DESI") mass spectrometry setup for swab analysis according to various embodiments. As shown in FIG. 8A, a desorption electrospray ionisation ("DESI") sprayer 800 and a mass spectrometry inlet capillary 801 may be positioned adjacent to a medical swab 802. The sprayer 800 may be provided with a gas supply 803, a power/solvent supply 804, and may be provided on a movable sprayer stage 805. The swab 802 may be provided on a movable swab stage 806.

As shown in FIG. 8B, the swab 802 may be rotated in order to access different portions of the analyte on the swab 802. The arrow in FIG. 8B shows the direction of motion of the swab according to an embodiment.

Initial experiments optimised the swab-inlet geometry, tip-sample angles and distances, and rotation speeds and provided high repeatability for the desorption electrospray ionisation ("DESI") mass spectrometry analysis. It was found that the optimum parameters for this setup include a swab-capillary distance of around 1-2 mm, a sprayer-swab distance of around 1-2 mm, a sprayer voltage of around 4.3 kV, a solvent flow rate of around 10 µL/min and a nebuliser gas pressure of around 7 bar.

FIG. 8C illustrates a number of swab positions and geometries in accordance with various embodiments.

Various embodiments relate to the application of desorption electrospray ionisation ("DESI") mass spectrometry to direct analysis of standard medical swabs, thereby permitting rapid assessment of perturbations of mucosal surface chemistry. As such, various embodiments relate to the development of a non-invasive point of care diagnostic technique, e.g. directed toward detection of diseases such as the detection of infections, dysbiosis, cancer and/or inflammatory diseases, and/or any of the other diseases mentioned elsewhere herein.

Medical swabs were analysed by desorption electrospray ionisation ("DESI") mass spectrometry with the intention of extracting chemical information relevant to patient care in a non-invasive procedure. In this context, desorption electrospray ionisation ("DESI") mass spectrometry represents a fast and direct method for metabolomic profiling of different mucosal membrane models or membranes (e.g. nasal, vaginal, oral) by desorbing and analysing molecules from the surface of standard medical cotton swabs.

Since the design of the swab for each clinical application may vary, with appropriate shape and materials being chosen for each type of application, different shapes of commercial available swabs were tested.

A study was performed in which vaginal mucosa (n=25 pregnant, n=25 non-pregnant), nasal mucosa (n=20) and oral mucosa (n=15) were sampled with medical rayon swabs from patients. Medical cotton swabs sold as Transwab® Amies (MWE medical wire, Wiltshire, UK) were used for sampling mucosal membranes which were then transferred to a sterile tube without buffer or storage medium solution and were stored at −80° C. in a freezer.

Figure 9:
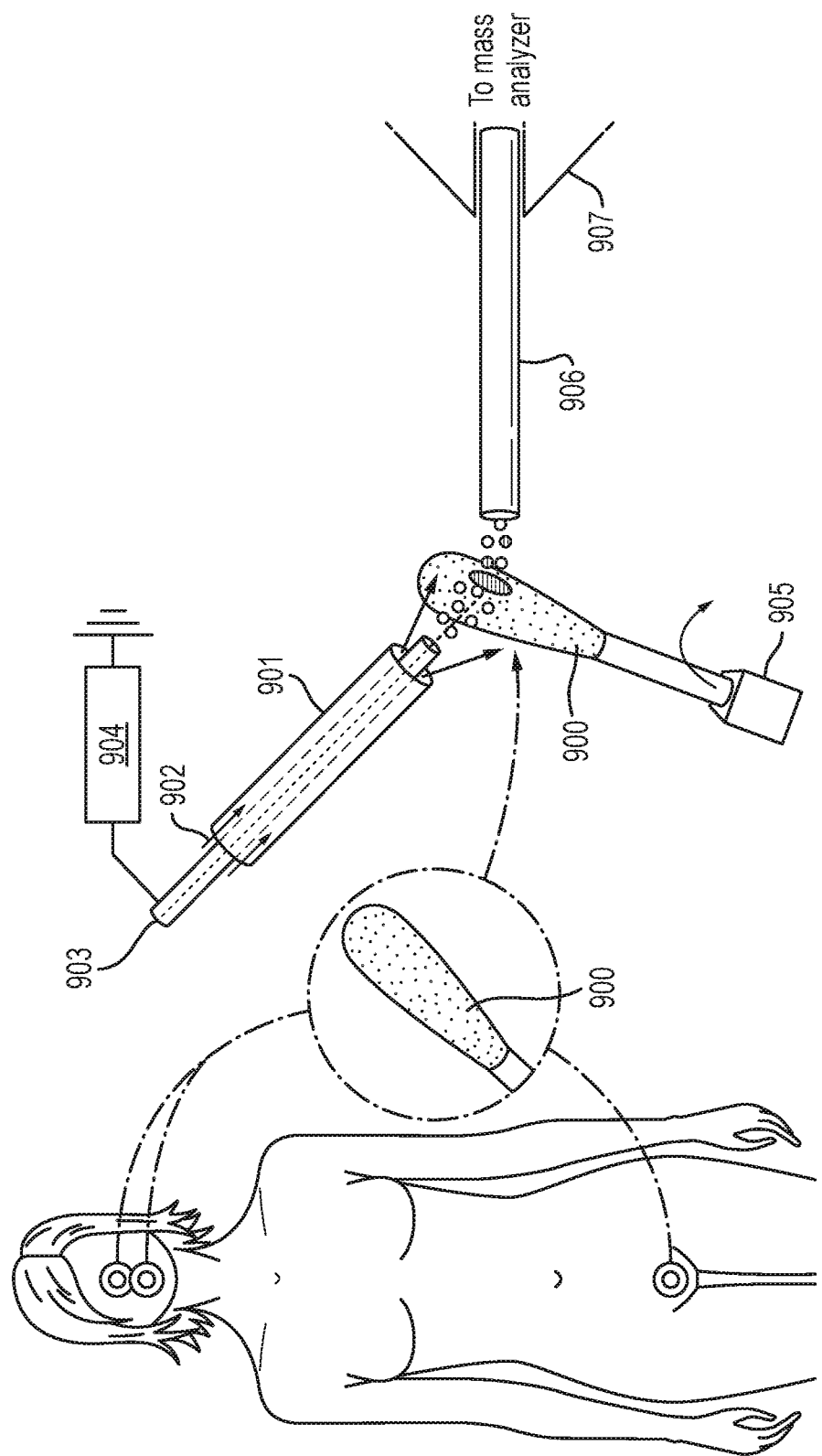
FIG. 9 shows schematically mucosal membrane sampling from selected parts of the human body (e.g., urogenital tract, oral or nose cavity) using medical cotton swabs as a sampling device wherein the surface of the medical swab may then be directly analysed by desorption electrospray ionisation ("DESI") mass spectrometry without prior sample preparation procedures according to various embodiments.

FIG. 9 highlights the sampling points of analysed mucosal membranes collected from the urogenital tract, oral and nasal cavity with a medical cotton swab 900. As illustrated by FIG. 9, the surface of the medical swab 900 was directly analysed by desorption electrospray ionisation ("DESI") mass spectrometry without prior sample preparation procedures.

Desorption electrospray ionisation ("DESI") mass spectrometry experiments were performed using a Xevo G2-S Q-TOF® mass spectrometer (Waters®, Manchester, UK). The desorption electrospray ionisation ("DESI") source comprises an electronic spray emitter 901 connected with a gas 902, solvent 903 and power supply 904 and an automatic rotatable swab holder device 905 with adjustable rotation speed.

For the desorption electrospray ionisation ("DESI") mass spectrometry analysis the medical swab 900 was positioned orthogonally to and in front of an inlet capillary 906 connected to the mass and/or ion mobility spectrometer atmospheric pressure interface 907. A mixed methanol:water solution (95:5) spray solvent was used at a flow rate of around 10 µL/min for desorption of the sample material. Nitrogen gas at around 7 bar and a voltage of around 3.4 kV were also provided to the sprayer 900.

The mucosa was absorbed from the surface of the rotated swabs by gently desorbing molecules with charged droplets of the organic solvent, and desorbed ions (e.g. lipids) were subsequently transferred to the mass and/or ion mobility spectrometer.

Full scan mass spectra (m/z 150-1000) were recorded in negative ion mode. Mass spectral data were then imported into a statistical analysis toolbox and processed. For data analysis and extraction of specific molecular ion patterns, an unsupervised principal component analysis ("PCA") as well as a recursive maximum margin criterion ("RMMC") approach were applied to improve supervised feature extraction and class information with leave one out cross validation ("CV") to determine classification accuracy within the data set.

Figure 10A:
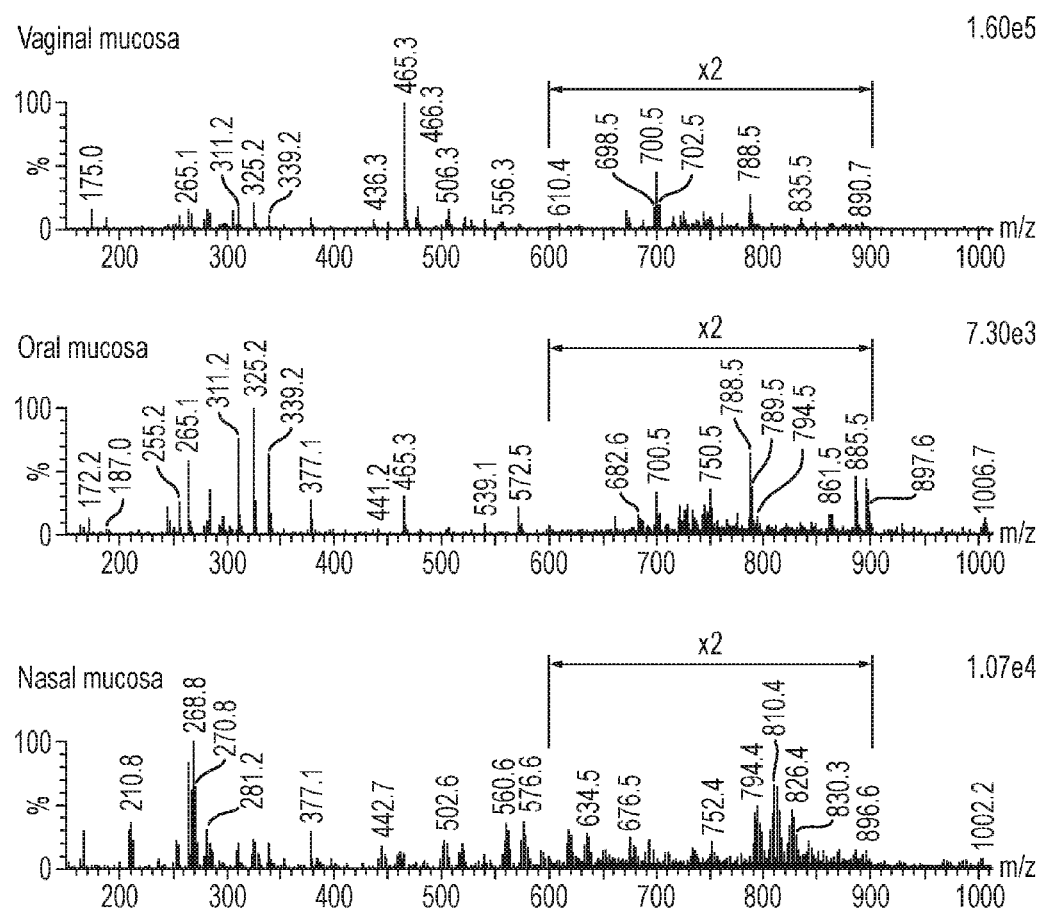
FIG. 10A shows averaged negative-ion desorption electrospray ionisation ("DESI") mass spectra from vaginal, oral and nasal mucosa recorded using a Xevo G2-S Q-Tof® mass spectrometer
Figure 10B:
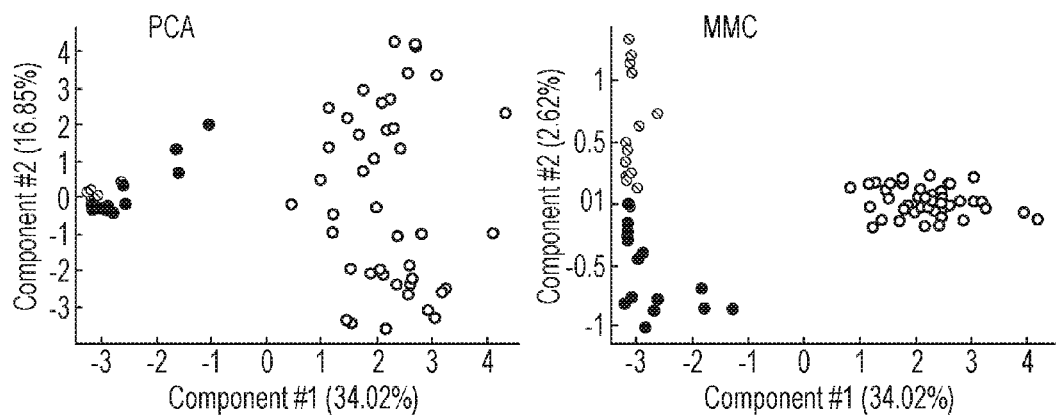
FIG. 10B shows a PCA and MMC score plot for vaginal (n=68), oral (n=15) and nasal (n=20) mucosa acquired with desorption electrospray ionisation ("DESI") mass spectrometry.

FIGS. 10A and 10B show the results of desorption electrospray ionisation ("DESI") mass spectrometry analysis of swabs, and multivariate statistical analysis including principal component analysis (PCA) and recursive maximum margin criterion (RMMC), which were used to identify lipid patterns characteristic of different mucosal models.

FIG. 10A shows averaged negative-ion mode desorption electrospray ionisation ("DESI") mass spectra from vaginal, oral and nasal mucosa recorded using a Xevo G2-S Q-Tof® mass spectrometer.

FIG. 10B shows a principal component analysis ("PCA") and a maximum margin criterion ("MMC") score plots for vaginal (n=68), oral (n=15) and nasal (n=20) mucosa acquired with desorption electrospray ionisation ("DESI") mass spectrometry.

As shown in FIG. 10A, unique lipid patterns were observed between different mucosal membrane models. The spectra for vaginal mucosa and oral mucosa featured predominately glycerophospholipids, e.g., [PS(34:1)–H]$^-$ having a mass to charge ratio ("m/z") of 760.4, [PS(36:2)–H]$^-$ having a m/z of 788.5 and [PI (36:1)–H]$^-$ having a m/z of 863.4.

As shown in FIG. 10A, nasal mucosa featured mainly chlorinated adducts [PC(36:2)+Cl]⁻ m/z 820.5, [PC(34:1)+Cl]⁻ m/z 794.5 and [PI(36:2)–H]⁻ m/z 826.4 in the m/z 700-900 range.

A characteristic feature of vaginal mucosa was deprotonated cholesterol sulphate at a m/z of 465.3, which was consistently observed to be the most dominant peak in the spectrum. Chemical assignment of this peak was confirmed by tandem mass spectrometry experiments. This compound is an important component of cell membranes with regulatory functions including a stabilizing role, e.g., protecting erythrocytes from osmotic lysis and regulating sperm capacitation.

Leave-one-patient-out cross validation of the multivariate model containing spectra obtained by the analyses of three mucosal models resulted in a high classification accuracy. This show that MS based profiling of different mucosal membranes allows stratification of patients based upon bacterial diversity.

Figure 11:
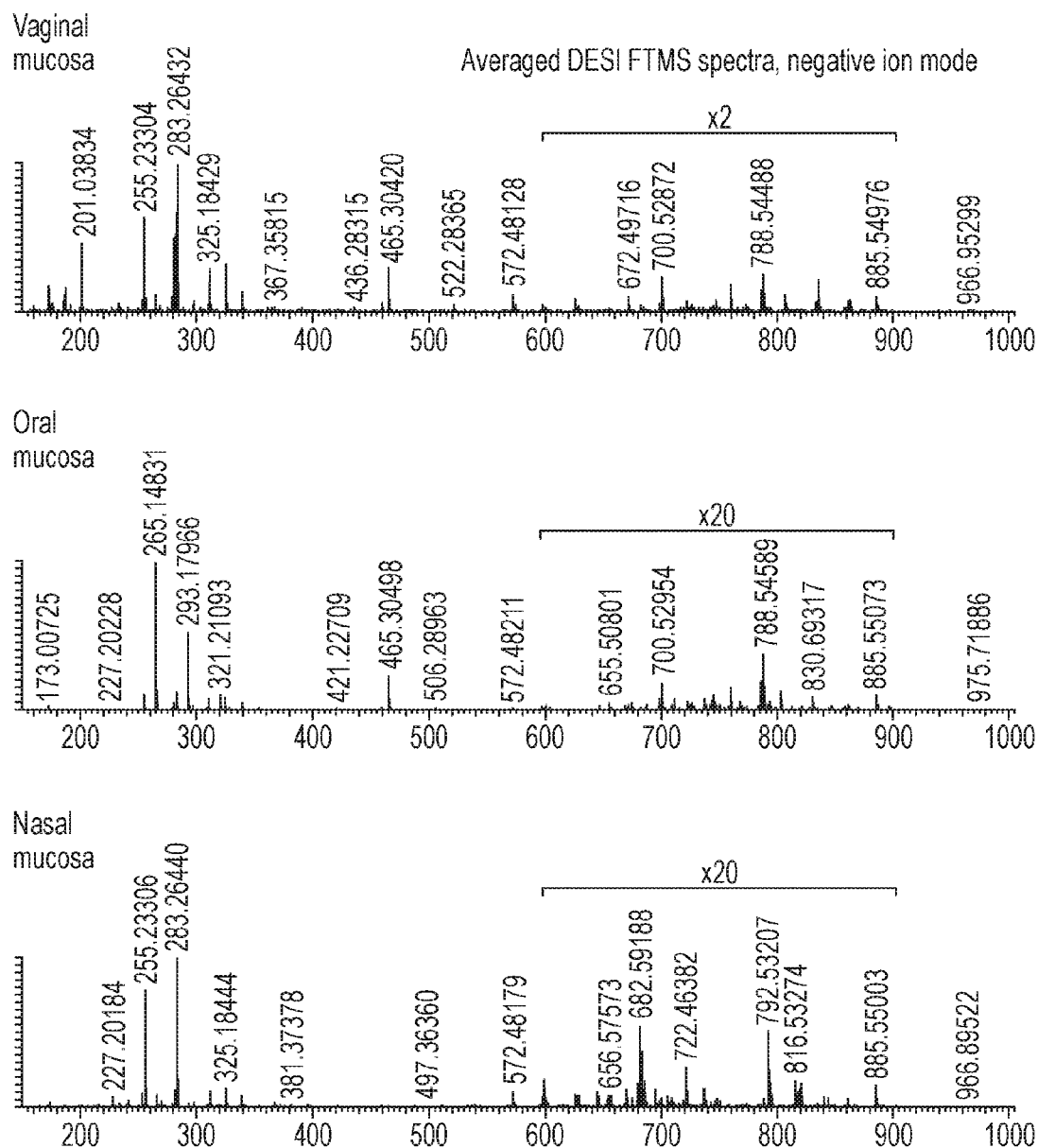
FIG. 11 shows desorption electrospray ionisation ("DESI") mass spectrometry spectra of vaginal, oral and nasal mucosal membranes in a negative ion mode obtained from medical cotton swabs, together with principal component analysis (PCA) and maximum margin criterion analysis providing a separation between different mucosal classes (nasal, oral, vaginal) with a prediction accuracy ranging from 92-100% obtained by leave one out cross validation.
Figure 11:
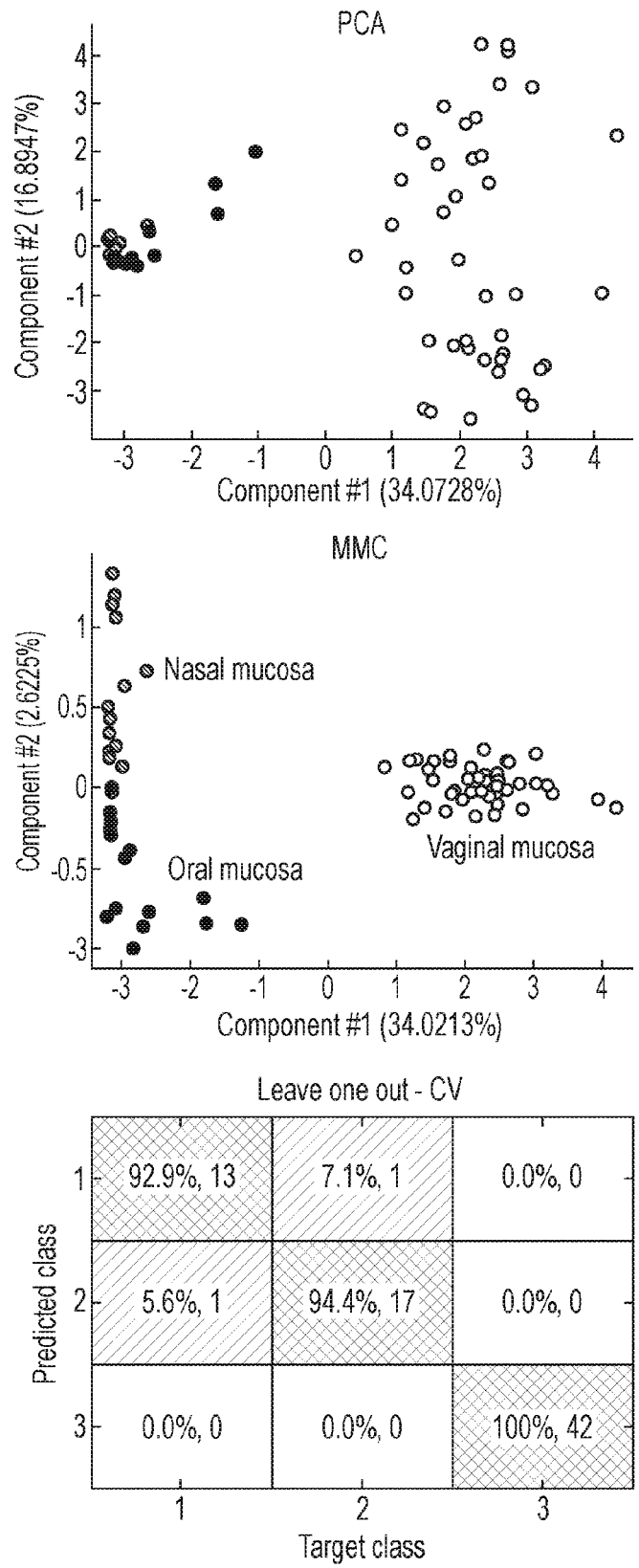

Similarly, FIG. 11 shows Fourier transform mass spectrometry ("FTMS") mass spectral data obtained from vaginal, oral and nasal mucosa on medical cotton swabs in negative ion mode in the mass range of m/z 150-1000. Again, different metabolic signatures were observed in each mucosal membrane model.

In total, 300 to 1000 spectral features found without isotopes and adducts including small human primary metabolites such as cholesterol sulphate, bacterial secondary metabolites including lactate as well as glycerophospholipids were tentatively identified by exact mass, isotope cluster distribution and tandem mass spectrometry experiments in the mucosal membrane.

Figure 12:
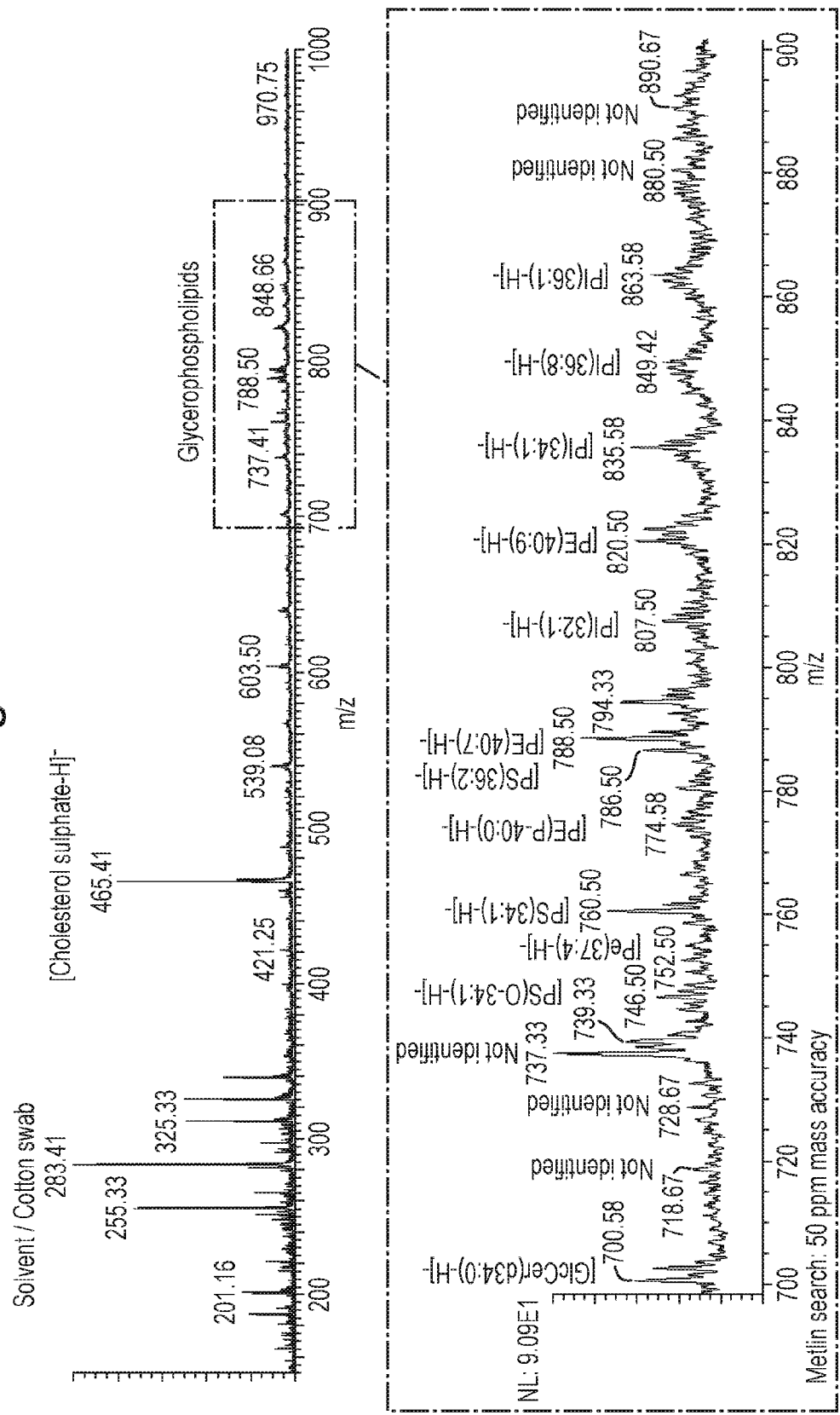
FIG. 12 shows a desorption electrospray ionisation ("DESI") mass spectrum of pregnant vaginal mucosal membrane obtained in negative ion mode from a medical cotton swab, wherein the urogenital mucosa was found to produce cholesterol sulphate [M-H]$^-$ having a mass to charge ratio of 465.41 as the most abundant lipid species as well as a different glycerophosholipids species such as glycerophosphoethanolamine (PE) [PE(40:7)–H]$^-$ having a mass to charge ratio of 788.50, glycerophosphoserine (PS) [PS(34:1)–H]$^-$ having a mass to charge ratio of 760.50 and glycerophosphoinositol (PI) [PI(36:1)–H]$^-$ having a mass to charge ratio of 863.58.
Figure 12:
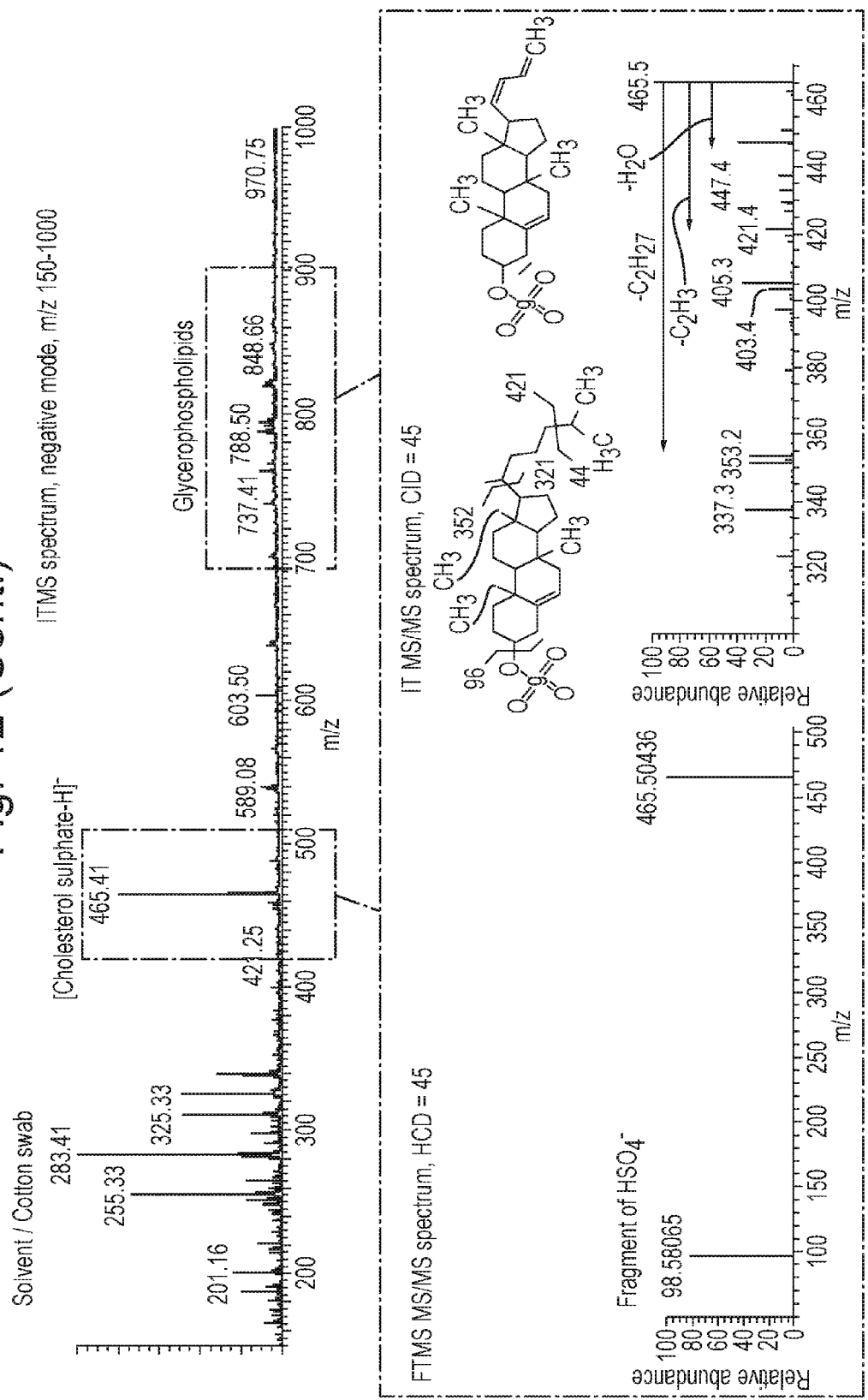

FIG. 12 shows a desorption electrospray ionisation ("DESI") mass spectrum relating to a pregnant vaginal mucosal membrane in more detail which was obtained in negative ion mode using a medical cotton swab. The urogenital mucosa was found to produce cholesterol sulphate [M-H]⁻ at a m/z of 465.41 as the most abundant lipid species as well as a different glycerophosholipids species such as glycerophosphoethanolamine (PE) [PE(40:7)–H]⁻ at a m/z of 788.50, glycerophosphoserine (PS) [PS(34:1)–H]⁻ at a m/z of 760.50 and glycerophosphoinositol (PI) [PI(36:1)–H]⁻ at a m/z of 863.58. As shown in FIG. 12, chemical assignment of the cholesterol sulphate peak was confirmed by tandem mass spectrometry experiments.

The mass spectral data of FIG. 11 were further processed using median normalization, background subtraction, Savitzky-Golay peak detection, peak alignment and log-transformation. Following data processing, multivariate statistical analysis was applied on the data set to characterise distinct mucosa models based on their metabolic profile. Multivariate statistical analysis tools including principal component analysis (PCA) and maximum margin criterion (MMC) were used to analyse the data set.

As shown in FIG. 11, the PCA score plot as well as the MMC score plot reveal a separation of the different mucosal membrane types within the first two components with a prediction accuracy between 92-100% obtained by leave one out cross validation.

It will be appreciated that analysis according to various embodiments results in characteristic profiles for the various sample types that can be clearly distinguished e.g., by using PCA, MMC and/or leave one out cross validation analyses. These results show the use of desorption electrospray ionisation ("DESI") mass spectrometry to characterise human mucosal membrane models, e.g. based on their metabolic signatures excreted by characteristic bacteria, as a fast bacterial identification method, e.g., compared to 16S rRNA sequencing.

Further embodiments are contemplated wherein chemical biomarkers in human mucosal membranes may be measured, which are reliable predictors e.g. in the cases of dysbiotic, inflammatory, cancerous and/or infectious diseases.

Pregnancy involves major changes in circulating hormone (e.g. estrogen and progesterone) levels as well as their secondary metabolites. Moreover, pregnancy is associated with a reduction in vaginal microbial diversity and an increase in stability. As described below, differences in the chemical signature of vaginal mucosa in normal pregnancy and the non-pregnant state can be readily determined using desorption electrospray ionisation ("DESI") mass spectrometry according to various embodiments.

A clinical set of pregnant (n=22, in a gestational age between 26 and 40 weeks) and non-pregnant mucosal membrane (n=22) were evaluated in more detail in order to reveal metabolic signature differences caused by a change in the vaginal microbiome during pregnancy. Desorption electrospray ionisation ("DESI") mass spectrometry spectra were acquired from both groups in negative ion mode in the mass range of m/z 150-1000. A number of different metabolites were detected in the vaginal mucosal membrane.

FIG. 13A shows averaged desorption electrospray ionisation ("DESI") mass spectra from pregnant and non-pregnant group acquired in the negative ion mode in the mass range m/z 150-1000. A comparison of the averaged spectra shown in FIG. 13A shows spectral differences between non-pregnant and pregnant mucosa metabolic profiles, especially in the lipid mass range from m/z 550-900.

Further data analysis comprising unsupervised PCA and RMMC analysis revealed clear separation between the two groups with a high (>80%) classification accuracy as determined using leave-one-out cross validation.

FIGS. 13B and 13C show the results of multivariate statistical analysis of pregnant (n=22) and non-pregnant (n=22) vaginal mucosal membrane using desorption electrospray ionisation ("DESI") mass spectrometry.

FIG. 13B shows principal component analysis and discriminatory analysis using RMMC and FIG. 13C shows analysis with leave-one-out cross-validation.

Figure 13D:
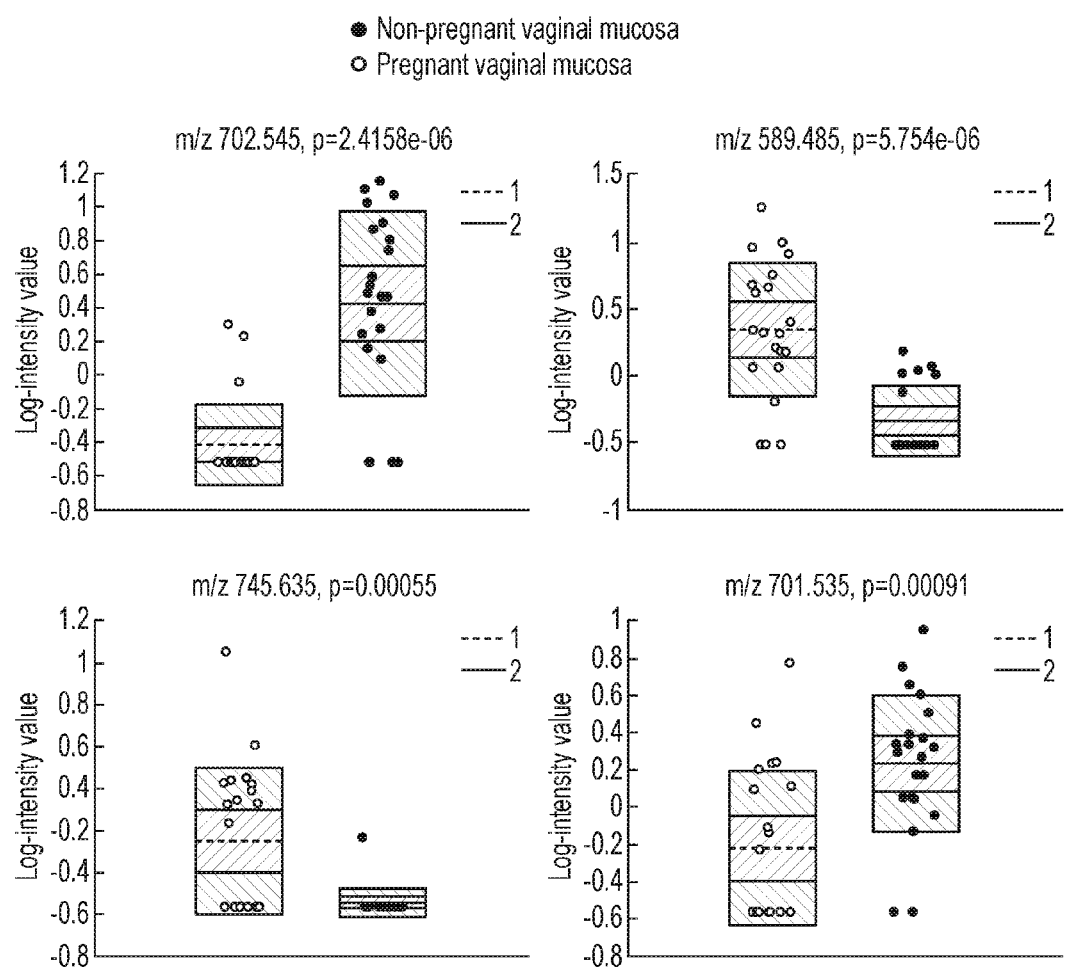
FIG. 13D shows box plots indicating significant differences of the abundance for selected peaks between non-pregnant and pregnant vaginal mucosal membranes mainly in the mass to charge ratio ("m/z") range 550-1000 and FIG. 13E shows the leave-one-out cross-validation.

FIG. 13D shows box plots which indicate significant differences in the abundance of selected lipid peaks between non-pregnant and pregnant vaginal mucosal membrane mainly in the range from m/z 550-1000 obtained by Kruskal-Wallis ANOVA, p<0.005.

Figure 13E:
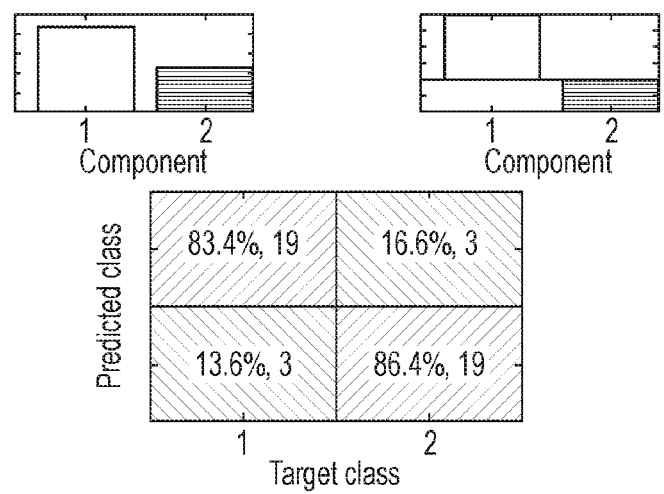

As shown in FIG. 13E, using RMMC both groups separate well in the RMMC space with a high (>80%) classification accuracy according to distinct metabolic signatures obtained by leave-one-patient-out cross validation.

Clinical studies have shown that vaginal microbial, e.g., bacterial diversity is associated with specific vaginal mucosal metabolites. For example, during healthy pregnancy the vaginal mucosa is colonized mainly by the *Lactobacillus* species. However, importantly, a shift towards vaginal dysbiosis during pregnancy may be a causal trigger for preterm birth.

Using the desorption electrospray ionisation ("DESI") mass spectrometry based technique disclosed herein allows females, e.g., women who have had a spontaneous preterm birth to be evaluated and compared to controls in order to identify biomarkers that can be used to predict preterm delivery. Moreover, the vaginal mucosa of pregnant females may be analysed using the desorption electrospray ionisation ("DESI") mass spectrometry based technique disclosed herein to analyse, e.g., diagnose or predict the risk of, a (spontaneous) preterm birth.

Mass spectral profiling of vaginal mucosa can enable an early identification of females, e.g., women who are at risk of infection during pregnancy based upon microbial, e.g., bacterial diversity in the vaginal mucosa. Furthermore, this enables targeted treatment response strategies.

Various embodiments are contemplated and include: (i) identification of vaginal mucosa metabolite biomarkers that are related to specific microbial, e.g., bacterial communities, optionally as determined using sequencing microbiome analysis; (ii) profiling of vaginal mucosal membrane during healthy pregnancy wherein microbe, e.g., bacteria-specific metabolites and signatures that are excreted during healthy pregnancy may be characterised in detail; and (iii) identification of diagnostic and prognostic metabolic signatures from vaginal mucosa membranes with poor pregnancy outcomes (e.g. preterm delivery).

FIG. 14A shows desorption electrospray ionisation ("DESI") mass spectrometry analysis of a bacteria (*Klebsiella pneumonia*) sample on a swab in accordance with an embodiment. The data illustrated in FIG. 14A shows that bacterial samples can be detected using desorption electrospray ionisation ("DESI") mass spectrometry on swabs, according to various embodiments. FIG. 14B shows for comparison rapid evaporative ionisation mass spectrometry ("REIMS") time of flight ("TOF") mass spectrometry data of a corresponding bacterial sample measured directly from an agar plate. The peaks highlighted by stars were detected with both ionisation techniques.

Desorption electrospray ionisation ("DESI") swab analysis for microorganism detection was further tested on six cultivated species including *Candida albicans, Pseudomonas montelli, Staphylococcus epidermis, Moraxella catarrhalis, Klebsiella pneumonia* and *Lactobacillus* sp. These are all important bacteria and fungi species that were isolated from vaginal mucosal membranes of pregnant patients and which were identified by sequence analysis such as 16S rRNA gene sequencing.

A swab was quickly dipped into a solution of diluted biomass from each species in 10 µL methanol, followed by desorption electrospray ionisation ("DESI") mass spectrometry analysis of the swab surface.

Figure 15A:
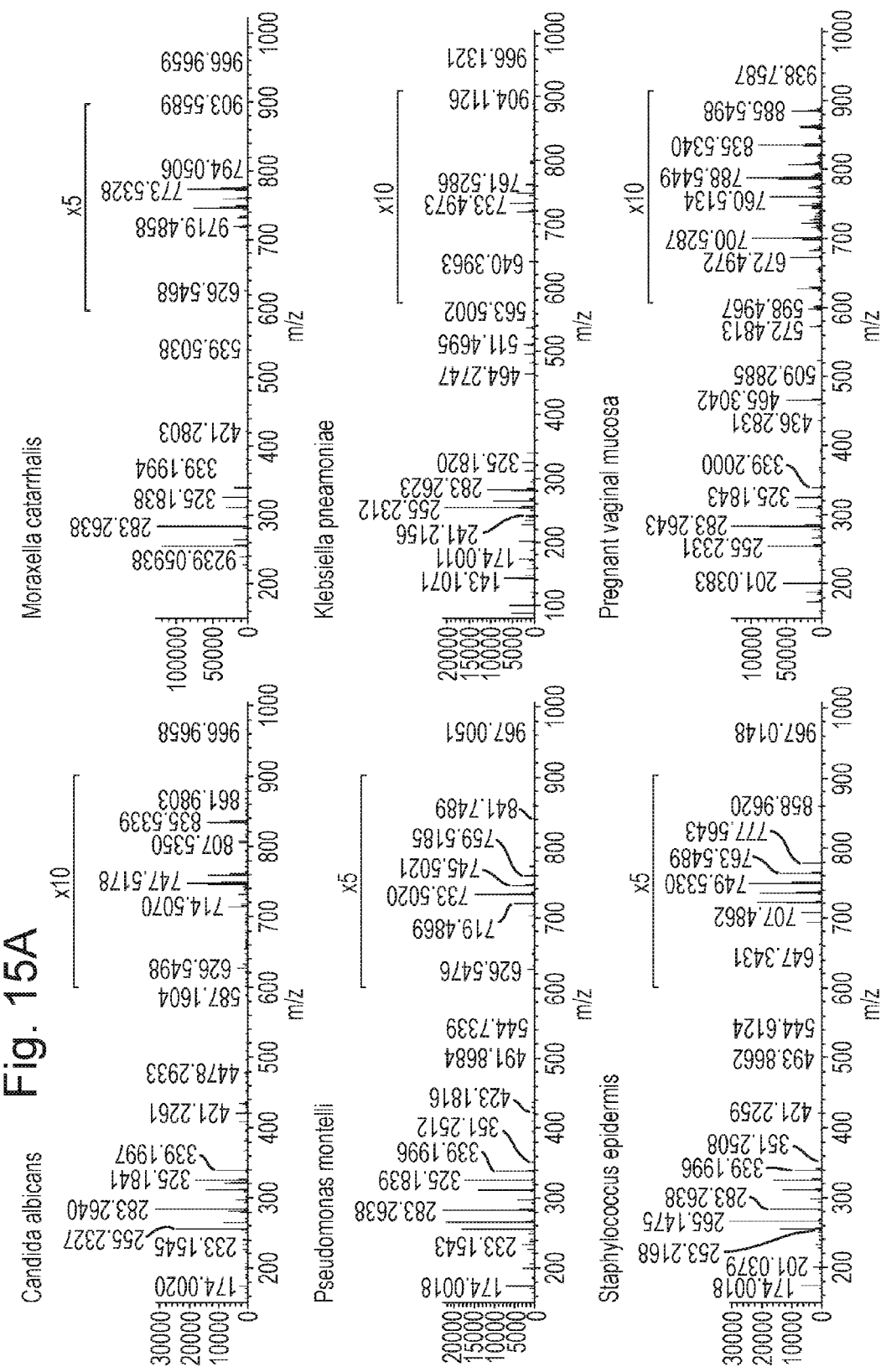
FIG. 15A shows averaged desorption electrospray ionisation ("DESI") mass spectra of diverse analysed microorganism species including *Candida albicans, Pseudomonas montelli, Staphylococcus epidermis, Moraxella catarrhalis, Klebsiella pneumonia* and *Lactobacillus* sp as well as pregnant vaginal mucosa.
Figure 15C:
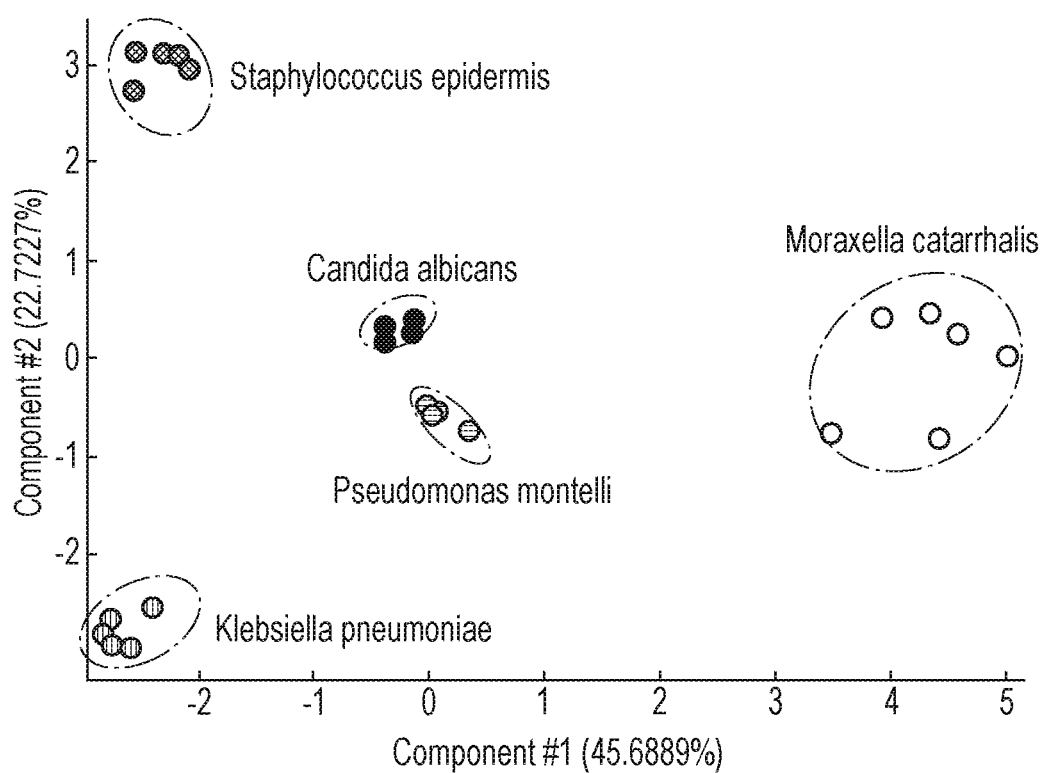

FIGS. 15A-C show microorganism analysis using desorption electrospray ionisation ("DESI") mass spectrometry on swabs.

FIG. 15A shows averaged desorption electrospray ionisation ("DESI") mass spectra of diverse analysed microorganism species including *Candida albicans, Pseudomonas montelli, Staphylococcus epidermis, Moraxella catarrhalis, Klebsiella pneumonia* and *Lactobacillus* sp.

FIGS. 15B and 15C show PCA plots showing a separation between the vaginal mucosa (pregnant and non-pregnant group) and the microorganism species within the first two components. In addition, a separation can be observed between the different bacteria and fungi species.

Unique spectral features were observed in the mass spectra as shown in FIG. 15A resulting in the ability to separate between different microorganism classes as well as from the vaginal mucosa in the PCA score plots (FIGS. 15B and 15C) within the first two components.

This result shows the potential to characterise microbe, e.g., bacteria-specific and host-response metabolite biomarkers and signatures from specific microbial, e.g., bacterial communities from the animal, e.g., human mucosal membrane using desorption electrospray ionisation ("DESI") mass spectrometry on medical swabs.

It will be appreciated that various embodiments provide a new desorption electrospray ionisation ("DESI") mass spectrometry setup for non-invasive and fast analysis of the mucosal metabolome profile from the surface of medical swabs. This arrangement has been successfully shown to be capable of differentiating animal, e.g., human mucosal membrane models and to enable microorganism identification. The method is capable of readily distinguishing different mucosal sites, biochemical alterations induced by physiological events such as pregnancy, and permits rapid identification of intact bacterial and fungal species.

Since desorption electrospray ionisation ("DESI") mass spectrometry analysis causes minimal sample destruction to the majority of the sample surface material, according to various embodiments the medical swab can optionally be sent directly after desorption electrospray ionisation ("DESI") analysis, e.g. to a microbiological lab, for further assessment such as cultivation, microbe identification/confirmation, and/or next generation sequencing analysis. As the resultant desorption electrospray ionisation mass spectrometry spectral profiles according to various embodiments harbour information descriptive of mucosal biochemistry as well as microbal-host interactions, the method according to various embodiments is applicable to a wide range of clinical applications.

Various embodiments provide a new point of care mucosal screening diagnostic method which uses standard cotton medical swabs as both the sampling probe for mucosal membrane uptake and ionisation probe for desorption electrospray ionisation ("DESI") mass spectrometry analysis. After data acquisition the obtained spectra may be compared with spectra collected in a database to provide a rapid diagnosis to the patient, e.g., within several seconds.

Various embodiments relate to the application of the desorption electrospray ionisation ("DESI") technique for direct metabolomic profiling of specific mucus models (nasal, vaginal, pharyngeal, bronchial, oesophageal) from the surface of standard medical swabs. Various embodiments relate to a rapid point-of-care diagnostic method for diseases, optionally selected from any of the diseases mentioned herein, e.g., inflammatory and pathogen-related diseases such as in immunological disorders, dysbiosis in the microflora (which may, e.g. be indicative of the risk of pre-term delivery during pregnancy), microbial, e.g., bacterial infections, or the detection of cancer or pre-cancerous states. The metabolomic profiling of animal, e.g., human mucosal membrane followed by detailed statistical analysis permits the identification of disease-specific metabolic profiles and/or taxon specific microbial, e.g., bacterial markers in a rapid, robust manner conducive to a point-of-care diagnostic method.

Figure 16:
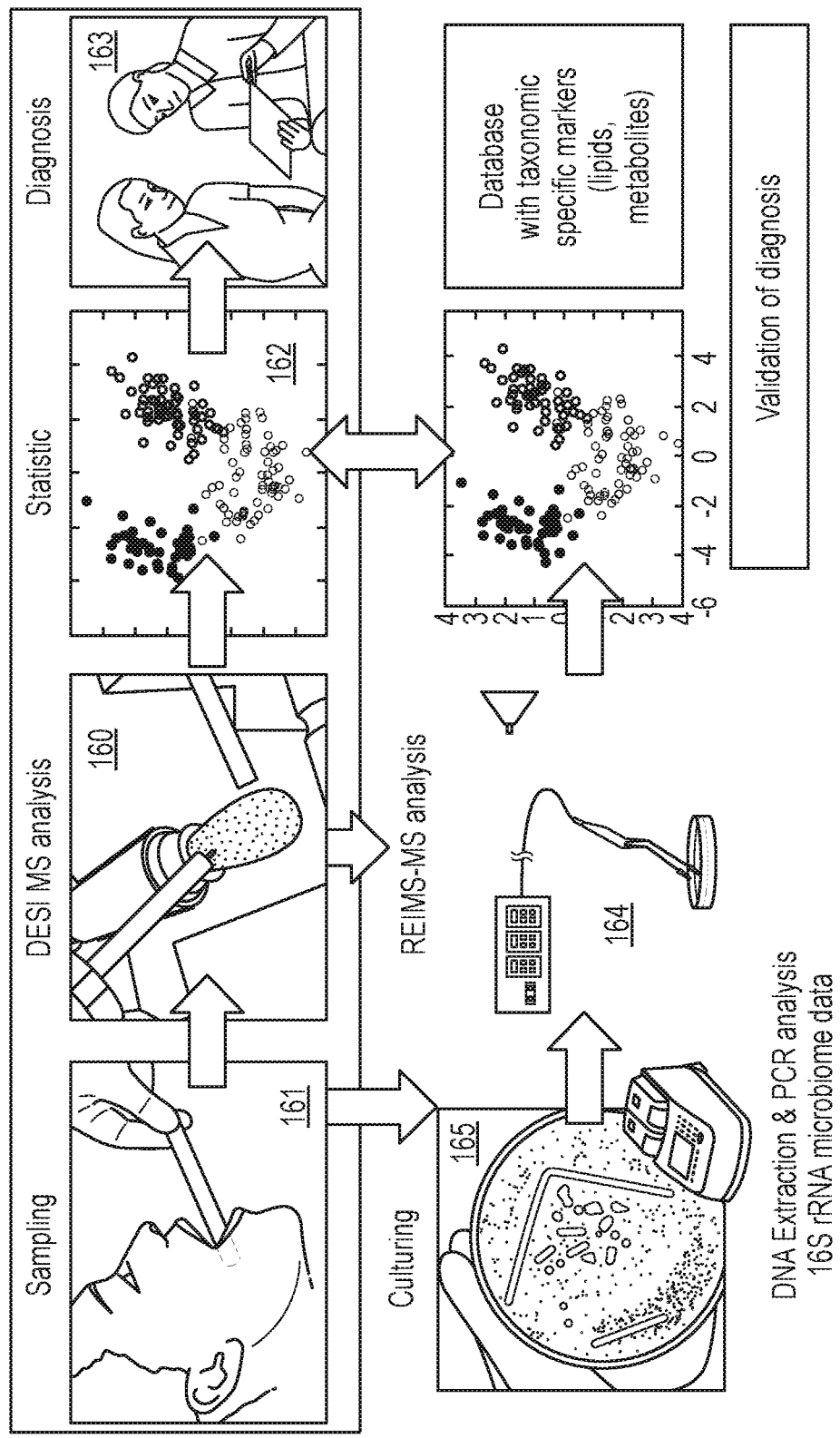
FIG. 16 shows schematically desorption electrospray ionisation ("DESI") mass spectrometry analysis, rapid evaporative ionisation mass spectrometry ("REIMS") mass spectrometry analysis and culturing based analysis of a sample on a swab according to various embodiments.

As shown in FIG. 16, according to various embodiments, desorption electrospray ionisation ("DESI") mass spectral analysis 160 of a sample sampled 161 onto a swab may be subjected to statistical analysis 162 in order to provide a diagnosis 163 (or prognosis).

The sample may be additionally or alternatively be analysed by rapid evaporative ionisation mass spectrometry ("REIMS") mass spectrometry 164.

Embodiments are contemplated wherein multiple different analysis techniques may be applied to the same swab (or another swab) so as to additionally perform analyses that rely on culturing 165, such as DNA extraction and PCR analysis, e.g., to produce complementary 16S rRNA microbiome data.

As shown in FIG. 16, any one or more or all of the additional analyses may be used to validate the desorption electrospray ionisation ("DESI") based diagnosis 163.

Figure 17A:
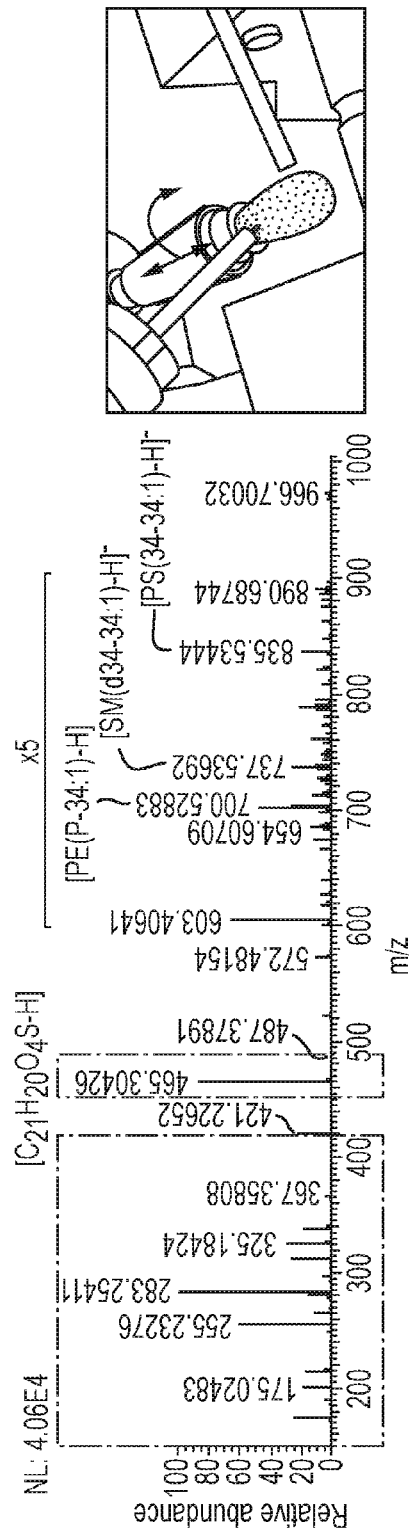
FIG. 17A shows desorption electrospray ionisation ("DESI") mass spectral data wherein a swab may be continuously rotated when subjected to desorption electrospray ionisation ("DESI") ionisation in order to improve the signal intensity and FIG. 17B shows rapid evaporative ionisation mass spectrometry ("REIMS") mass spectral data wherein a swab may be dipped, soaked or otherwise immersed in a fluid (such as water) prior to be being subjected to rapid evaporative ionisation mass spectrometry ("REIMS") analysis in order to improve the signal intensity.

FIG. 17A illustrates how continuous rotation of a swab whilst subjecting the swab to desorption electrospray ionisation ("DESI") analysis can result in an enhanced signal intensity.

Rapid Evaporative Ionisation Mass Spectrometry ("REIMS") Analysis of a Swab

Various embodiments described herein also relate to methods of rapid evaporative ionisation mass spectrometry ("REIMS") analysis of a swab, wherein a sample on a swab is subjected to rapid evaporative ionisation mass spectrometry ("REIMS") analysis. This approach, however, is destructive for the swab, and in the bipolar mode the contact closure of the electrodes is restricted.

When a swab is analysed by rapid evaporative ionisation mass spectrometry, then the swab may be dipped, soaked or otherwise immersed in a fluid (such as water) prior to be being subjected to rapid evaporative ionisation mass spectrometry ("REIMS") analysis.

Figure 17B:
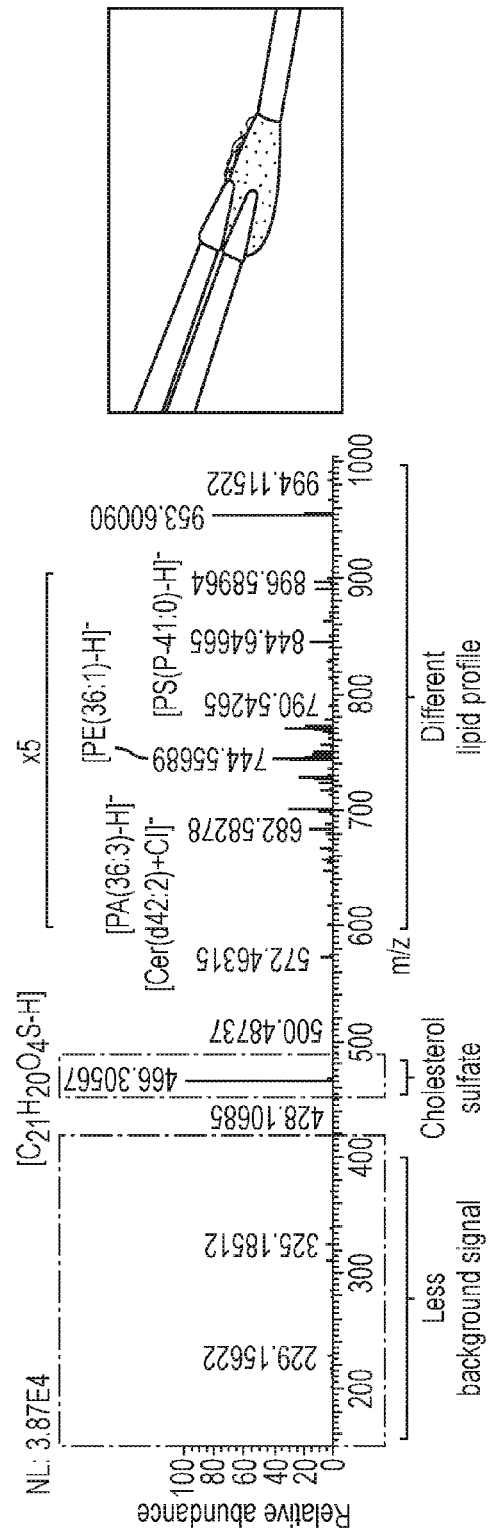

As also illustrated in FIG. 17B, soaking a swab in a fluid prior to rapid evaporative ionisation mass spectrometry has also been shown to enhance the signal intensity.

The rapid evaporative ionisation mass spectrometry ("REIMS") technique will now be described in more detail with reference to FIG. 18.

Figure 18:
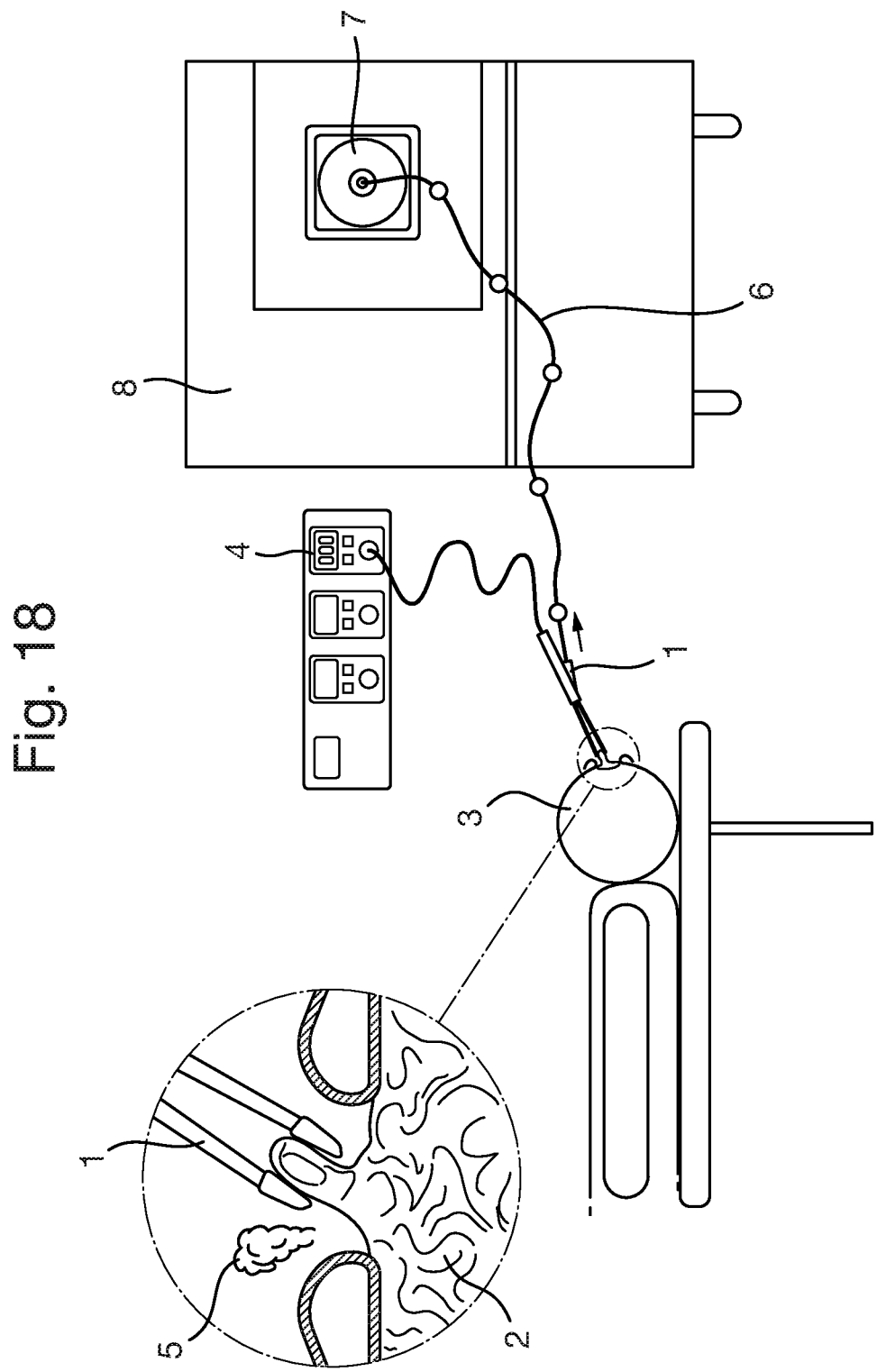
FIG. 18 shows schematically the rapid evaporative ionisation mass spectrometry ("REIMS") technique in accordance with various embodiments.

FIG. 18 illustrates a method of rapid evaporative ionisation mass spectrometry ("REIMS") wherein bipolar forceps 1 may be brought into contact with in vivo tissue 2 of a patient 3. In the example shown in FIG. 18, the bipolar forceps 1 may be brought into contact with brain tissue 2 of a patient 3 during the course of a surgical operation on the patient's brain. However, according to various embodiments, and as shown in FIG. 17B, the bipolar forceps 1 may be brought into contact with a sample provided on a medical swab.

An RF voltage from an RF voltage generator 4 may be applied to the bipolar forceps 1 which causes localised Joule or diathermy heating of the tissue 2 or sample. As a result, an aerosol or surgical plume 5 is generated. The aerosol or surgical plume 5 may then be captured or otherwise aspirated through an irrigation port of the bipolar forceps 1. The irrigation port of the bipolar forceps 1 is therefore reutilised as an aspiration port. The aerosol or surgical plume 5 may then be passed from the irrigation (aspiration) port of the bipolar forceps 1 to tubing 6 (e.g. ⅛" or 3.2 mm diameter Teflon® tubing). The tubing 6 is arranged to transfer the aerosol or surgical plume 5 to an atmospheric pressure interface 7 of a mass spectrometer 8 and/or ion mobility analyser.

According to various embodiments a matrix comprising an organic solvent such as isopropanol may be added to the aerosol or surgical plume 5 at the atmospheric pressure interface 7. The mixture of aerosol 3 and organic solvent may then be arranged to impact upon a collision surface within a vacuum chamber of the mass and/or ion mobility spectrometer 8. According to one embodiment the collision surface may be heated. The aerosol is caused to ionise upon impacting the collision surface resulting in the generation of analyte ions. The ionisation efficiency of generating the analyte ions may be improved by the addition of the organic solvent. However, the addition of an organic solvent is not essential.

Analyte ions which are generated by causing the aerosol, smoke or vapour 5 to impact upon the collision surface are then passed through subsequent stages of the mass spectrometer (and/or ion mobility analyser) and are subjected to analysis such as mass analysis and/or ion mobility analysis in a mass analyser or filter and/or ion mobility analyser. The mass analyser or filter may, for example, comprise a quadrupole mass analyser or a Time of Flight mass analyser.

Modified Swabs

Various further embodiments are directed to a modified, chemically functionalised and/or solid-phase microextraction ("SPME") swab approach.

As discussed above, various chemically modified swabs for use with desorption electrospray ionisation ("DESI") mass spectrometry in accordance with various embodiments have been found to exhibit an improved sensitivity and/or reduced background compared with conventional (non-modified) swabs. Modified swabs as described in more detail below exhibit an improved signal to noise ratio compared with conventional (non-modified) swabs across particular mass to charge ratio ranges.

Figure 19:
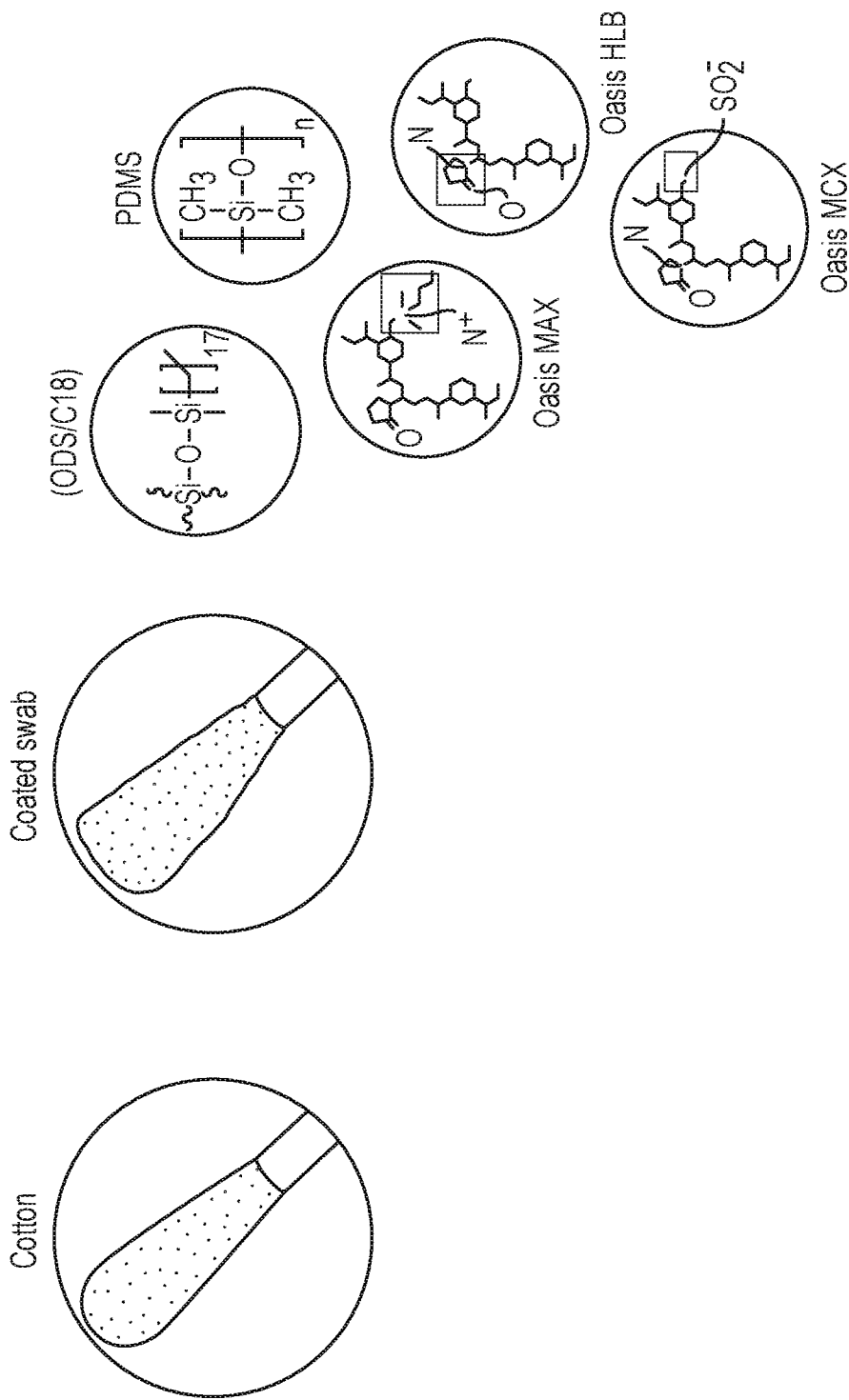
FIG. 19 illustrates various advantages and disadvantages associated with standard cotton swabs and coated or chemically modified swabs according to various embodiments.

As illustrated in FIG. 19, standard cotton swabs are commercially available and are relatively non-invasive. However, swabs comprise fibrous material having absorbing properties, the swabs release molecules relatively poorly, provide non-selective extraction and can result in a relatively high background signal being observed.

In contrast, coated or chemically modified swabs according to various embodiments can beneficially provide a solid surface, enable selective extraction and exhibit improved sensitivity.

According to various embodiments, a (standard) medical swab may be wetted or otherwise functionalised with one or more sorbents in order either: (i) to increase the intensity or signal of observed analyte ions across one or more particular mass to charge ratio ranges; and/or (ii) to reduce the intensity or signal due to undesired background ions across one or more particular mass to charge ratio ranges.

In accordance with various embodiments, standard cotton medical swabs may be coated with ODS/C18 (octadecyl), polydimethylsiloxane ("PDMS"), Oasis® MAX (mixed-mode cation exchange), Oasis® HLB (hydrophilic-lipophilic-balanced) and/or Oasis® MCX (mixed-mode cation exchange). For example, according to an embodiment the swab may be provided with a monolayer or multiple layers of sorbent materials such as C18 (octadecyl), C18 (octadecyl) EC (end capped), HLB (hydrophilic lipophilic balanced particles) and/or divinyl benzene ("DVB"). These various sorbent materials may be used to enhance the extraction efficiency of certain compounds from the mucosal membrane matrix.

FIG. 20 illustrates the improved sensitivity that is provided using modified swabs, in accordance with various embodiments. Desorption electrospray ionisation ("DESI") mass spectrometry analysis of nasal fluid on a swab was performed using a standard cotton swab (FIG. 20A), a swab modified with ODS/C18 (FIG. 20B), and a swab modified with Oasis® HLB (FIG. 20C). In particular, an improved lipid signal is observed over the mass to charge ratio range of around m/z 730-890.

Figure 21:
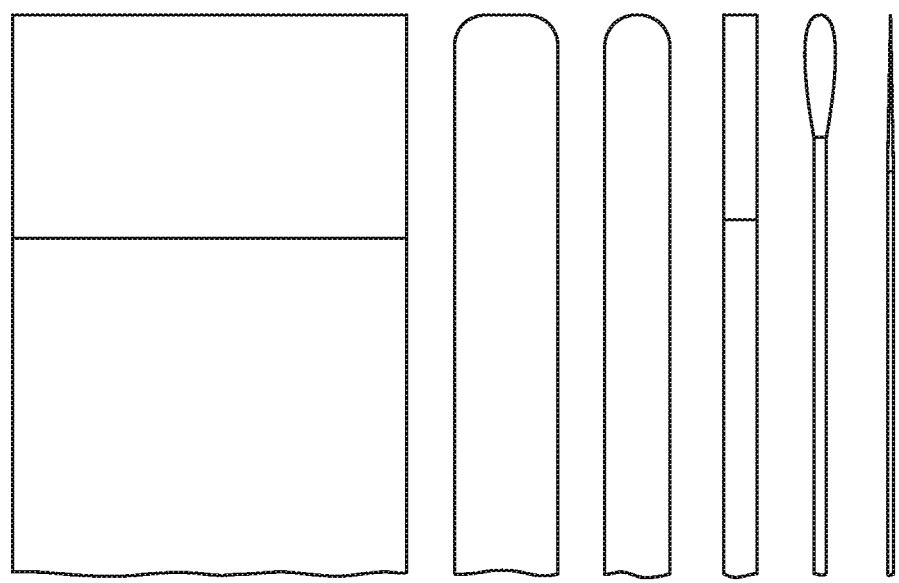
FIG. 21 shows various solid-phase microextraction ("SPME") coated materials for mucosal membrane sampling in accordance with various embodiments.

FIG. 21 shows a collection of different coated materials comprising different formats, shapes and sorbent materials.

The biocompatible and functionalised polybutylene terephthalate ("PBT") plastic, swabs and fibres may be prepared by dip-coating the material surface, e.g. using peroxyacetyl nitrate ("PAN") as an adhesive for the sorbent materials. Using the dip-coating technique a mono-layer coating can be achieved with a coating thickness of approximately 5-10 µm.

Functionalised swabs with C18 (octadecyl), C18 (octadecyl) EC (endcapped), DVB (divinyl benzene) WAX (weak anion exchange) and HLB (hydrophilic-lipophilic-balanced) coating were tested for desorption electrospray ionisation ("DESI") mass spectrometry metabolic profiling of saliva and compared with the standard medical cotton desorption electrospray ionisation ("DESI") mass spectrometry analysis approach.

As shown in FIG. 22, once functionalised, a swab may require washing 210 and/or conditioning 211 prior to use. Washing 210 and/or conditioning 211 steps remove any contaminants left over from the manufacturing process which might interfere with the desorption electrospray ionisation ("DESI") mass spectrometry analysis. For example, washing 210 may involve soaking in a first solvent to remove any contaminants left over from the manufacturing process whilst conditioning 211 may involve soaking in a second solvent to remove any remaining contaminants, including any unwanted residue of the first solvent. Suitable solvents for these steps include methanol, acetonitrile (ACN), isopropanol, water and mixtures thereof.

Once the swab has been contacted with the sample or bodily surface 212, it may be washed 214 to remove unbound material which may interfere with the analysis, leaving the analyte of interest bound to the swab. For example, if the analyte of interest is a lipid, unbound salts or polar molecules can be removed by washing 214. The swabs are then analysed 215 by desorption electrospray ionisation ("DESI") mass spectrometry or a variant thereof such as using a desorption electroflow focusing ionisation ("DEFFI") ion source.

An optimised workflow was designed in which swabs were washed 210 in MeOH/ACN/(CH$_3$)$_2$CHOH (50:25:25) for around 1 hour, conditioned 211 in MeOH:H$_2$O (50:50) for around 1 minute, dipped in analyte (e.g. saliva) solution for around 2 min and 30 minutes so as to sample 212 the analyte, dried 213 for around 5 minutes, and rinsed 214 by dipping in water for around 1 second, prior to desorption electrospray ionisation ("DESI") mass spectrometry analysis 215 with MeOH:H$_2$O (95:5). This workflow was shown to enhance the extraction efficiency and sample clean-up during mucosal membrane analysis.

FIGS. 23A-E show a comparison of saliva spectra obtained in negative (left) and positive (right) ion mode obtained using a standard medical swab (FIG. 23A) and three layer coated swabs (FIGS. 23B-E) which were coated with four different sorbents (C18 (octadecyl), C18 (octadecyl) EC (end capped), HLB (hydrophilic-lipophilic-balanced) and DVB (divinyl benzene) WAX (weak anion exchange)).

Figure 23D:
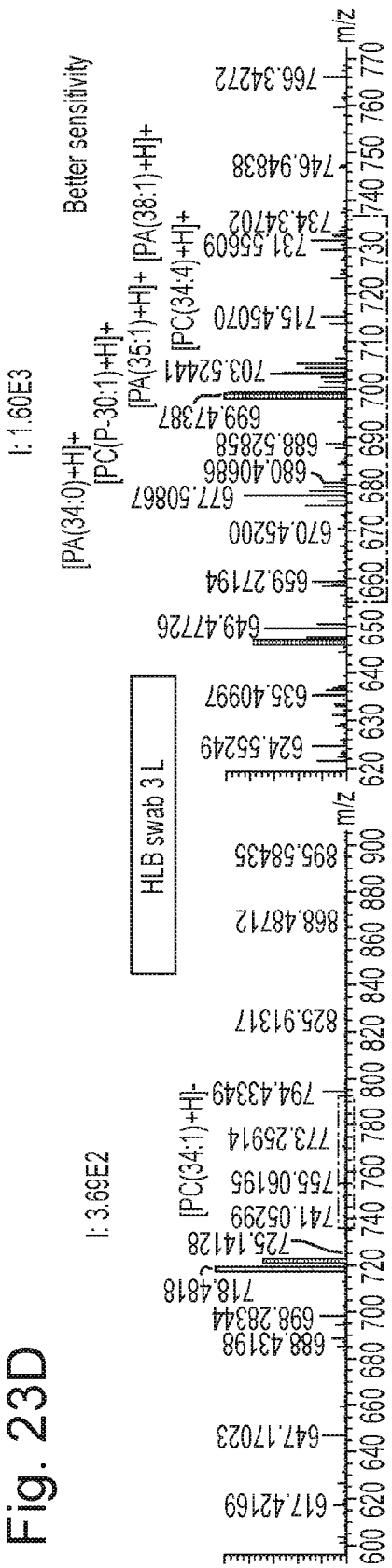
FIG. 23D shows a saliva mass spectrum obtained in negative ion mode (left) and positive ion mode (right) using a standard medical swab coated with three layers of HLB (hydrophilic-lipophilic-balanced) sorbent and FIG. 23E shows a saliva mass spectrum obtained in negative ion mode (left) and positive ion mode (right) using a standard medical swab coated with three layers of DVB (divinyl benzene) WAX (weak anion exchange) sorbent.
Figure 23E:
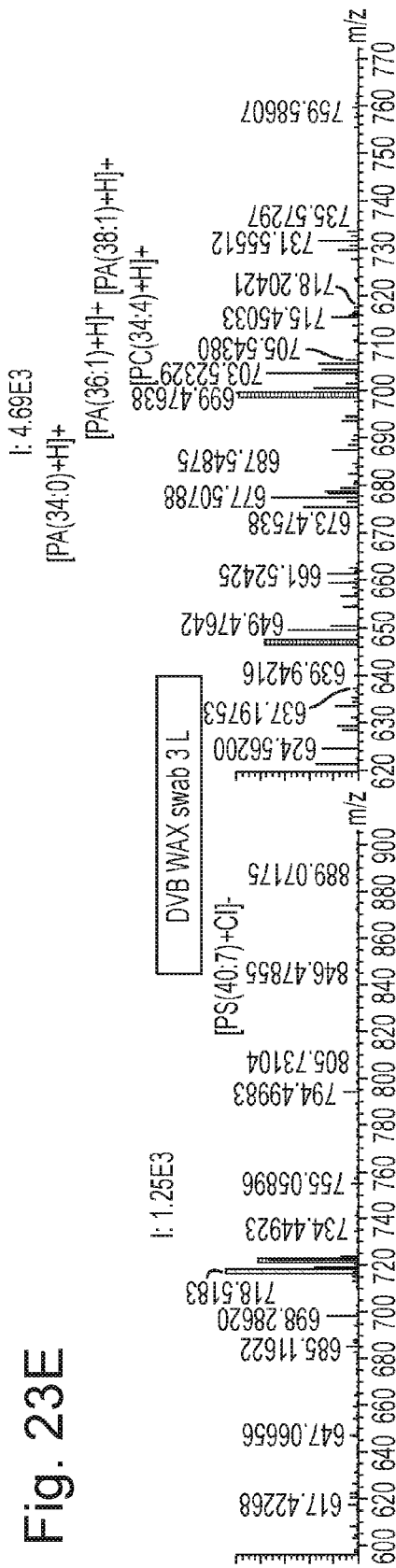

FIG. 23A shows a saliva spectra obtained in negative ion mode (left) and positive ion mode (right) using a standard medical swab, FIG. 23B shows a saliva spectra obtained in negative ion mode (left) and positive ion mode (right) using a standard medical swab coated with three layers of C18 (octadecyl) sorbent, FIG. 23C shows a saliva spectra obtained in negative ion mode (left) and positive ion mode (right) using a standard medical swab coated with three layers of C18 (octadecyl) EC (end capped) sorbent, FIG. 23D shows a saliva spectra obtained in negative ion mode (left) and positive ion mode (right) using a standard medical swab coated with three layers of HLB (hydrophilic-lipophilic-balanced) sorbent and FIG. 23E shows a saliva spectra obtained in negative ion mode (left) and positive ion mode (right) using a standard medical swab coated with three layers of DVB (divinyl benzene) WAX (weak anion exchange) sorbent.

Whereas medical cotton swabs show high background peaks especially in positive ion mode (highlighted peaks), coated swabs results in cleaner background spectra and enhanced lipid sensitivity from the saliva matrix (green highlighted) using C18 (octadecyl) in negative ion mode (m/z 700-900) and HLB (hydrophilic-lipophilic-balanced) and DVB (divinyl benzene) WAX (weak anion exchange) swabs in positive ion mode (m/z 600-720).

In summary, functionalized swabs were found to improve sensitivity for hydrophobic analytes, due to improved selective extraction efficiency of unpolar analytes from the saliva matrix compared to standard cotton swabs.

Various embodiments described herein provide an optimised desorption electrospray ionisation ("DESI") mass spectrometry method for metabolic profiling of mucosal membrane samples on medical swabs.

Various embodiments facilitate the differentiation between different mucosa models.

Various embodiments allow bacterial metabolic profiles to be obtained from swabs.

Furthermore, functionalised swabs in accordance with various embodiments improve the sensitivity, e.g. for hydrophobic analytes.

According to various embodiments, rapid evaporative ionisation mass spectrometry ("REIMS") may be used as a complementary analysis technique for mucosal profiling.

It will be appreciated that next generation sequencing techniques such as 16S RNA sequencing permit identification and characterization of bacteria that are colonized in the human mucosal membrane. However, clinical implementation for bacterial identification is limited due to cost and time constrains of this approach. Desorption electrospray ionisation ("DESI") mass spectrometry analysis of mucosal swabs, however, fulfils all criteria set for a routine diagnostic procedure. Using desorption electrospray ionisation ("DESI") mass spectrometry to rapidly and directly identify metabolite signatures excreted in animal, e.g., human mucosal membrane by specific microbes, e.g., bacteria enables objective biochemical information to be generated which enables microbes, e.g., bacteria to be identified and which enhances current clinical decisions making (e.g. target antibiotic treatment) in the context of analysis, e.g., diagnosis of diseases, such as any of the diseases mentioned elsewhere herein, e.g., infections, dysbiosis, cancer, and/or inflammatory disease.

Modified Swab Surface Chemistry

Various embodiments provide a medical swab for use in the methods of various embodiments, wherein the swab has been chemically modified to enhance selectivity for an analyte.

Medical swabs normally comprise a head portion, often referred to as a bud, and a shaft which may be attached to or integral with the head. The shaft may be formed from plastic, wood, rolled paper or wire. The head portion is often hydrophilic. The head portion may be formed from cotton, rayon, plastic fibres or foams. Suitable plastics for both the shaft and head include polyurethanes and polyesters such as polyethylene terephthalate (PET) and polybutylene terephthalate (PBT).

References herein to cotton, rayon, plastic fibres or foam swabs are references to the materials from which the head of the swabs is made.

In principle, any known medical swabs or medical sampling devices may be chemically modified (functionalised) to improve their selectivity for particular analytes of interest prior to analysis using desorption electrospray ionisation ("DESI") mass spectrometry, or a variant thereof. The swabs may be disposable (i.e. intended for a single use). Swabs for chemical modification/functionalization include cotton, rayon, polyester and foam swabs, particularly cotton or polyester swabs.

Chemical modification of a swab involves introduction of a suitable functionalising chemistry to the surface of the swab. The functionalising chemistry may be attached to the swab by chemical means, for example via covalent bonds, or by physical means, for example via physical entrapment or by using a suitable adhesive material. In various embodiments, the chemical modification involves formation of a coating on the surface of the swab.

The nature of the surface functionalization will depend on the type of analyte of interest. After functionalization, the surface of the swab may be hydrophilic or hydrophobic. It may also comprise ionic groups. For example, hydrophobic or lipophilic surfaces are beneficial for analysis of lipids, whilst charged or hydrophilic surfaces may be beneficial for the analysis of proteins or certain drug metabolites.

The chemical modification should preferentially bind the analyte or analytes of interest, but should not bind the analyte so tightly that the analyte cannot subsequently be removed for analysis by mass spectrometry.

Functionalised swabs may be used to analyse a sample, such as urine, after the sample have been removed from a patient. The surface functionalization used in swabs for such in vitro use need not be biocompatible. Alternatively, functionalised swabs may be used directly to collect a sample from the patient, for example by swabbing a mucosal membrane. Swabs which are intended for in vivo use or to come into direct contact with a patient should be biocompatible.

The surface functionalization may be introduced to the swab through adsorption or absorption and though processes including, but not limited to: solution phase processes, gas phase processes, chemical vapour deposition, molecular vapour deposition, atomic layer deposition, dip coating, electrochemical coating, or spray coating.

Direct chemical attachment of a functionalising molecule to the swab may occur by reaction of a functional group in the functionalising molecule with a functional group in the swab material to form a covalent bond. Covalent attachment of the functionalising molecule to the swab can include, but is not limited to, reaction of a functional group of the swab such as an alcohol, aldehyde, amine, carboxylic acid or alkene group to form a silyl-ether, ether, thio-ether, carbamate, carbonate, carbon-carbon bon, carbon-nitrogen bond, urea or ester. For example, cellulosic swabs such as cotton or rayon swabs will comprise a plurality of hydroxy groups which may react with functional groups such as carboxylic acids in the functionalising molecule, leading to covalent attachment of the functionaliser to the surface of the swab via ester linkages.

Methods for functionalising cellulosic surfaces are known in the art and include those disclosed in US2009/0126891, the content of which is incorporated herein by reference.

Alternatively, the chemical modification of a swab may involve physical entrapment of a suitable functionaliser by the swab. This method may be useful when the functionaliser is a solid particle such as a functionalised silica particle or an ion exchange resin particle.

Another alternative is to use a thin layer of adhesive or other binder material to attach functionalised particles to the surface of a swab. Any known medical grade adhesive may be potentially used, including cyanoacrylates, epoxy adhesives and acrylate adhesives. Suitable such adhesives include the Loctite® medical grade adhesives available from Henkel Corporation, Connecticut, USA. Any inert, biocompatible particles may potentially be used including silica, hybrid silica-organic or carbon particles. Suitable particles are generally about 1 to about 60 micrometers in diameter, and may be about 2 to about 10 micrometers in diameter, and may be about 2 to about 5 micrometers in diameter.

A beneficial surface functionalization of a swab involves attachment of solid-phase extraction materials to the surface of the swab, for example by physical entrapment or through use of a suitable adhesive or binder material. As used herein, the term "solid phase extraction materials" refers to solid materials useful as stationary phases in gas or liquid chromatography. Such materials are usually in particulate form and are often silica or polymer resin based. Solid-phase extraction materials for the analysis of lipids may be reverse-phase stationary phases.

Functionalised silica and hybrid silica/organic particles are well known for use as stationary phases in liquid chromatography. Methods of functionalising silica surfaces to render them more selective for analytes of interest are known in the art. Suitable modifications include those disclosed in US 2012/0141789 and US 2008/0073512, the disclosures of which are incorporated herein by reference.

Surface modifiers for chromatographic stationary phases typically include organic functional groups which impart a certain chromatographic functionality to the stationary phase. Functional groups on the surface of the stationary phase particles may be derivatized by reaction with suitable modifiers. Silica particles possess silanol groups whilst silica/organic hybrid particles may possess both organic groups and silanol groups which may be derivatized.

Suitable surface modifiers for chromatographic stationary phases include those having the formula $Z_a(R')_b Si\text{---}R^2$, where $Z=Cl, Br, I, C_1\text{-}C_5$ alkoxy, dialkylamino or trifluoromethanesulfonate; a and b are each an integer from 0 to 3 provided that $a+b=3$; $R^1$ is a $C_1\text{-}C_6$ straight, cyclic or branched alkyl group, and $R^2$ is a functionalizing group.

R' may be selected from the group consisting of methyl, ethyl, propyl, isopropyl, butyl, t-butyl, sec-butyl, pentyl, isopentyl, hexyl and cyclohexyl.

The functionalizing group $R^2$ may include alkyl, alkenyl, alkynyl, aryl, cyano, amino, diol, nitro, ester, cation or anion exchange groups, an alkyl or aryl group containing an embedded polar functionalities or chiral moieties. Examples of suitable $R^2$ functionalizing groups include chiral moieties; $C_1\text{-}C_{30}$ alkyl, including $C_1\text{-}C_{20}$, such as octyl ($C_8$), octadecyl ($C_{18}$) and triacontyl ($C_{30}$); alkaryl, e.g., $C_1\text{-}C_4$-phenyl; cyanoalkyl groups, e.g., cyanopropyl; diol groups, e.g., propyldiol; amino groups, e.g., aminopropyl; and alkyl or aryl groups with embedded polar functionalities, e.g., carbamate functionalities such as disclosed in U.S. Pat. No. 5,374,755; and chiral moieties. Such groups include those of the general formula:

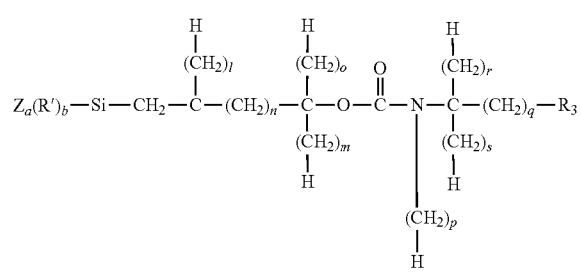

wherein l, m, o, r and s are 0 or 1, n is 0, 1, 2 or 3 p is 0, 1, 2, 3 or 4 and q is an integer from 0 to 19; $R_3$ is selected from the group consisting of hydrogen, alkyl, cyano and phenyl; and Z, R', a and b are defined as above. The carbamate functionality may have the general structure indicated below:

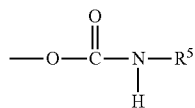

wherein $R^5$ may be, e.g., cyanoalkyl, t-butyl, butyl, octyl, dodecyl, tetradecyl, octadecyl, or benzyl. Advantageously, $R^5$ is octyl, dodecyl, or octadecyl.

$R^2$ may be a $C_1$-$C_{30}$ alkyl group, and may be a $C_1$-$C_{20}$ alkyl group.

Particularly beneficial surface modifiers are selected from the group consisting of octyltrichlorosilane, octadecyltrichlorosilane, octyldimethylchlorosilane and octadecyldimethylchlorosilane, and may be in particular octyltrichlorosilane or octadecyltrichlorosilane.

Particulate solid phase extraction materials are available from Waters Corporation, USA. Particularly suitable such materials are silica particles functionalised with octadecyl (C18) groups or polydimethylsiloxane (PDMS) groups.

Alternatively, swabs may be functionalised by attachment of particulate polymer resins to the surface of the swab, for example by physical entrapment or through use of a suitable adhesive or binder. Suitable such resins are known in the art as stationary phases for use in chromatography. These include reversed-phase, ion exchange, and mixed mode stationary phases, including ion exchange-reverse phase stationary phases.

Reverse-phase chromatography stationary phases may be particularly suitable for preparing swabs for analysis of lipids. Suitable reversed-phase stationary phases include polydivinylbenzene (DVB) and copolymers of N-vinyl pyrrolidone and divinylbenzene, such as Oasis® HLB available from Waters Corporation.

Mixed-mode ion exchange/reversed-phase sorbents based on modified N vinylpyrrolidone/divinylbenzene copolymers may also be used. Such copolymers in which some of the benzene rings are sulfonated or carboxylated can provide cation-exchange functionality. Such copolymers modified by attachment of imidazolium, —$CH_2$-piperazine groups or quaternary ammonium groups such as —$CH_2N^+(CH_3)_2$ ($C_4H_9$) to some of the benzene rings can provide anion exchange functionality. Suitable such sorbents are available from Waters Corporation under the trade names Oasis® MCX, Oasis® WCX, Oasis® MAX and Oasis® WAX.

Solid particles for attachment to swabs may also be functionalised with polymer coatings. Polymer coatings are known in the literature and may be provided generally by polymerization or polycondensation of physisorbed monomers onto the surface of the particle without chemical bonding of the polymer layer to the support (type I), polymerization or polycondensation of physisorbed monomers onto the surface with chemical bonding of the polymer layer to the support (type II), immobilization of physisorbed prepolymers to the support (type III) and chemisorption of presynthesized polymers onto the surface of the support (type IV): see, e.g., Hanson, et al., J. Chromat. A656 (1993) 369-380, the text of which is incorporated herein by reference.

Any polymers used to make solid phase extraction materials may potentially be used to form polymeric coatings on the surface of a swab. Suitable coating polymers include polydivinylbenzene (DVB), copolymers of N-vinylpyrrolidone and divinylbenzene, and polydimethylsiloxane.

Coating a particle with a polymer may be used in conjunction with other surface modifications as described above. In particular, SPEM particles may be embedded in the polymer coating such that the coating acts as a binder to trap the particles on or near the surface of the swab.

Functionalised swabs may also be prepared by forming a solution or dispersion of the chemical modifier and dipping a swab into the solution or dispersion. The swab is then allowed to dry and the dipping step repeated, as necessary. Such dipping may allow the formation of monolayers of the chemical modifier on the surface of the swab. The thickness of a layer formed by this method may be in the region of 5-10 micrometers.

Fibres for use as solid phase microextraction (SPME) media are known in the art. Such fibres normally comprise a fused silica fibre or metal wire with a thin polymer coating. For example, C18 coated fused-silica fibres have been proposed for use in sampling for drugs in urine (Kennedy et al, Analytical Chemistry, Vol. 82, No. 17, 1 Sep. 2010). Swabs for use in the various embodiments may further comprise such fibres.

In various embodiments, the swabs do not include any fused silica-based fibers or any metal fibers/wires.

Sterilisation of Swabs

If the functionalised swabs are to be used to analyse a sample which has been removed from a patient, then the swabs are not necessarily required to be sterilised prior to use. For example, swabs used to analyse urine samples may not require sterilisation prior to use. However, any swabs which are intended to come into contact with a patient will require sterilisation prior to use. Any standard technique in the art known for sterilising medical swabs may potentially be used to sterilise the functionalised swabs of various embodiments. Suitable sterilisation methods include, without limitation, autoclaving, heating, gamma radiation and ethylene oxide sterilisation.

Multiple Analyses of the Same Swab

As discussed above, a particular benefit of using desorption electrospray ionisation ("DESI") mass spectrometry to analyse a sample provided on a medical swab is that multiple different analyses of the same sample, i.e. of the same swab, may be performed.

Performing multiple different analyses of or on the same sample enables multiple different sets of information about the same sample to be obtained in a particularly convenient and efficient manner. This is in particular possible because desorption electrospray ionisation ("DESI") mass spectrometry is a relatively non-destructive analysis technique and also because various commercial analysis techniques, such as culturing techniques and nucleic acid sequencing techniques, e.g., 16S rRNA sequencing techniques, are optimised to use samples which are provided on medical swabs.

Accordingly, following a single sample acquisition onto a swab, the sample on the swab may be analysed multiple times using multiple different analysis techniques, where at least one of the techniques (e.g. the first technique used) comprises desorption electrospray ionisation ("DESI") mass spectrometry.

According to various other embodiments, data directed analyses of a sample on a swab (the same sample on the same swab) may be performed. For example, depending upon the results of the first (e.g. desorption electrospray ionisation ("DESI") mass spectrometry) analysis and/or where an ion of interest is detected using the first (e.g. desorption electrospray ionisation ("DESI") mass spectrometry) analysis, a further analysis may be selected, altered and/or optimised and performed.

In these embodiments, one or more of the analysis techniques may comprise a culturing analysis method, e.g. where the swab is contacted with, e.g., wiped across or dipped into, a solid or liquid culturing medium, the culturing medium is incubated, and then the culturing medium is examined, e.g., under a microscope to identify any microbes present.

One or more of the analysis techniques may comprise a gene sequencing method such as a 16S rRNA sequencing method for identifying microbes.

One or more of the analysis techniques may comprise a Matrix-Assisted Laser Desorption Ionisation ("MALDI") method for identifying microbes.

One or more of the analysis techniques may comprise a Rapid Evaporative Ionisation Mass Spectrometry ("REIMS") method for identifying microbes.

As shown and described above in relation to FIG. 16, any one or more or all of the additional analyses may be used to validate and/or supplement a desorption electrospray ionisation ("DESI") based identification or diagnosis.

Analysis of Swabs Comprising a Faecal or Body Fluid Specimen Using Ambient Ionisation Mass Spectrometry, e.g. DESI and/or REIMS Technology Analysis of a faecal or body fluid specimen according to various embodiments may provide information about a disease and/or microbiome, optionally a mucosal microbiome and/or the microbiome of the GI lumen. Thus, optionally, the method may involve the analysis of a swab comprising a faecal and/or body fluid specimen. For example, a faecal and/or body fluid specimen may be analysed for the presence of a cell, a compound, and/or a microbe.

The method may optionally allow an analysis of metabolic differences between various conditions, which may optionally be selected from any of the conditions listed elsewhere herein, e.g., Irritable Bowel Syndrome, Colorectal cancer and/or Inflammatory Bowel Disease. By identifying taxonomic specific biomarkers the method may optionally allow the analysis, e.g., diagnosis, of microbial infections and/or mixed microbial communities.

The cell may, e.g., be a mammalian cell, a white blood cell, a red blood cell, a foetal cell, and/or a cancer cell.

Optionally, a faecal and/or body fluid specimen may be analysed for the presence of a microbe and/or to analyse a microbiome. Details of analysis of microbes and/or the microbiome are provided elsewhere herein.

Optionally, a faecal and/or body fluid specimen may be analysed for the presence of a compound. The compound may, e.g., comprise or consist of a biomolecule, an organic compound, and/or an inorganic compound. It may optionally be selected from any of the compounds listed elsewhere herein. Optionally, it may be bile, haemoglobin, or a derivative of any thereof.

Optionally, a faecal and/or body fluid specimen other than blood may be analysed for the presence of blood. For example, the presence of blood in urine may be indicative of an infection or other disease. For example, the presence of blood in a faecal specimen may optionally be used to analyse a bleed in the GI tract and/or anus. Optionally, the bleed may be indicative of a disease selected, for example, from anal fissure, diverticular disease, a polyp, an inflammatory disease, angiodysplasia, and/or any of the diseases mentioned elsewhere herein.

Optionally, a faecal and/or body fluid specimen may be analysed for the presence of bile or a derivative thereof, e.g., to analyse a liver and/or kidney disease, and/or any of the diseases mentioned elsewhere herein.

The analysis of faecal specimens may optionally involve the use forceps-based rapid evaporative ionisation mass spectrometry ("REIMS"), wherein a sample of the faecal specimen may be taken between the forceps and the probes may then be drawn together.

Figure 24:
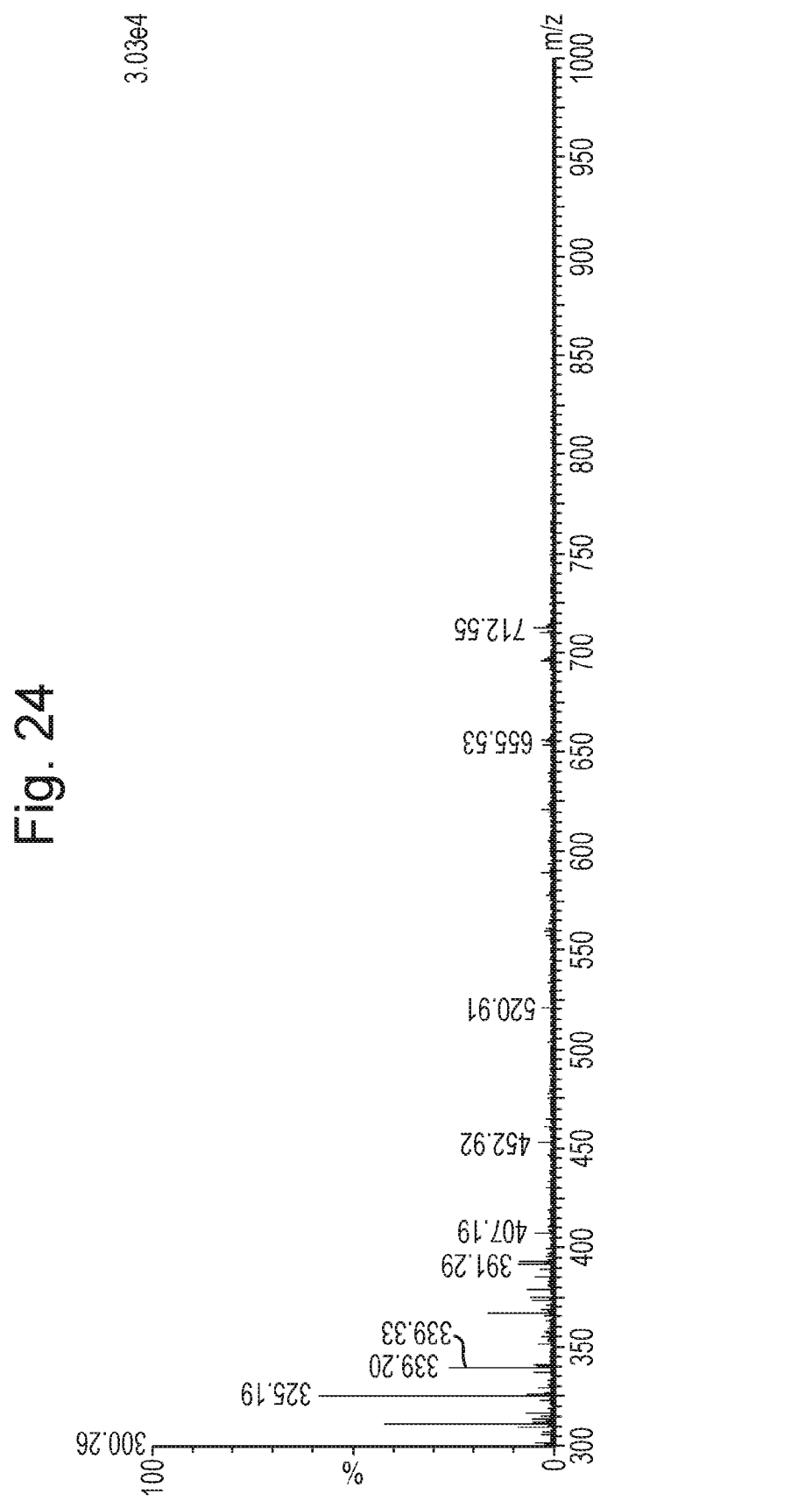
FIG. 24 shows a spectrum observed when analysing stool samples using rapid evaporative ionisation mass spectrometry ("REIMS") analysis.

FIG. 24 shows a spectrum observed when analysing stool samples using the rapid evaporative ionisation mass spectrometry ("REIMS") technique.

Desorption Electrospray Ionisation ("DESI") Sprayer with Heated Transfer Capillary FIG. 25A shows an embodiment and comprises a Desorption Electrospray Ionisation ("DESI") sprayer 300 in which a solvent capillary 302 may be arranged to direct electrically charged droplets 304 of solvent at a swab surface 310. A sample 311 may be located on the swab surface 310, which may comprise analyte particles. The charging of the solvent droplets may be achieved through the use of a high-voltage power supply 306 that contacts the capillary 302. The high-voltage power supply 306 may comprise an electrode 307 which may contact any portion of the capillary 302 so that it is operable to charge the solvent droplets as they leave an outlet end 303 of the capillary 302. The outlet end 303 of the capillary may be directed towards the swab surface 310.

A sheath gas 308 (e.g., nitrogen) may be arranged to surround the capillary 302 so as to nebulise the solvent as it emerges from the capillary 302 and direct the electrically charged solvent droplets 304 towards the swab surface 310. The sheath gas may be introduced through a tube 312 that may be coaxial to the solvent capillary 302, having an inlet 314 at an end distal to the swab surface 310 and an outlet 316 at an end facing the swab surface 310.

The outlet 316 of the sheath gas tube 312 may be concentric to the outlet end 303 of the capillary, which can facilitate in nebulising the solvent as it emerges from the capillary 302. The solvent emerging from the outlet end 303 of the solvent capillary 302 may be nebulised by the sheath gas 308. A connector 318 may connect the tube 312 to a source of gas suitable to use as a sheath gas. The sheath gas 308 may comprise nitrogen or standard medical air, and the source of sheath gas may be a source of nitrogen gas or standard medical air.

As the solvent droplets 304 contact the swab, analyte particles on the swab can desorb and the charged droplets and analyte mixture 320 may be transferred into a transfer capillary or transfer device 330 that may lead to an ion analyser, mass analyser or filter and/or ion mobility analyser and/or mass spectrometer 340. The charged droplet and analyte mixture may be transferred through an inlet 332 of the transfer capillary or transfer device 330. This may be achieved by placing the opposite end 333 of the transfer capillary or transfer device 330 in a low pressure region 352, for example a vacuum stage of the mass analyser or filter and/or ion mobility analyser and/or mass spectrometer 340.

The charged droplet and analyte mixture (including e.g., analyte ions) may be transferred by ion optics 352 to an analysis region of the ion analyser and/or ion mobility analyser and/or mass spectrometer 340. The ion optics 352 may comprise an ion guide, for example a StepWave® ion guide.

The analyte ions may be guided to the analysis region by applying voltages to the ion optics 352. The analyte ions may then be analysed by the mass analyser or filter and/or ion mobility analyser and/or mass spectrometer 340.

According to an embodiment the ion analyser and/or mass analyser or filter and/or ion mobility analyser and/or mass spectrometer 340 may comprise an ion mobility spectrometer. According to a yet further embodiment the ion analyser and/or mass analyser or filter and/or ion mobility analyser and/or mass spectrometer 340 may comprise the combination of an ion mobility spectrometer and a mass spectrometer.

As a result of the analysis, chemical information about the sample 311 may be obtained.

One or more heaters may be provided to heat the various parts of the apparatus shown in FIG. 25A. For example, a heater may be provided to heat one or more of the solvent capillary 302, the sheath gas tube 312, the swab surface 310 and the transfer or inlet capillary 330.

The one or more heaters may comprise a wire heater (e.g., a tungsten wrap) and/or may be configured to heat the respective part to at least 50° C., 100° C., 200° C., 300° C., 400° C., 500° C., 600° C., 700° C. or 800° C. However, any type of heater may be used that has the function of heating the respective part, for example a blower or an inductive heater.

FIG. 25A shows a first heater 342 that may be arranged and adapted to heat the transfer or inlet capillary 330, such that the solvent and analyte mixture 320 may be heated before being passed onward, for example to the mass analyser or filter and/or ion mobility analyser and/or mass spectrometer 340.

The first heater 342 may be located anywhere along the solvent capillary 330, for example adjacent to or at the inlet 341 of the ion analyser, mass analyser or filter and/or ion mobility analyser and/or mass spectrometer. Alternatively, the first heater 342 may be located adjacent to or at the inlet 332 of the solvent capillary or transfer device 330. The first heater 342 may comprise a wire heater (e.g., a tungsten wrap) and/or may be configured to heat the inlet capillary to at least 50° C., 100° C., 200° C., 300° C., 400° C., 500° C., 600° C., 700° C. or 800° C.

A second heater 344 may be arranged and adapted to heat the sheath gas tube 312, such that the solvent and/or sheath gas may be heated.

The second heater 344 may be located at the end of the tube 312 nearest the swab surface 310, such that the solvent and/or sheath gas may be heated before being directed at the swab surface 310. The second heater 344 may comprise a wire heater (e.g., a tungsten wrap) and/or may be configured to heat the tube 312 and/or the solvent and/or the sheath gas to at least 50° C., 100° C., 200° C., 300° C., 400° C., 500° C., 600° C., 700° C. or 800° C.

A third heater 346 may be arranged and adapted to heat the solvent capillary 302, such that the solvent may be heated.

The third heater 346 may be located anywhere along the solvent capillary 302, for example nearest the end 305 located away from the swab surface 310, such that the solvent may be heated before it is surrounded by the sheath gas tube 312. The third heater 346 may comprise a wire heater (e.g., a tungsten wrap) and/or may be configured to heat the solvent capillary 302 and/or the solvent to at least 50° C., 100° C., 200° C., 300° C., 400° C., 500° C., 600° C., 700° C. or 800° C.

A fourth heater 348 may be arranged and adapted to heat the swab surface 310, such that the sample 311 and/or the swab surface 310 may be heated. The fourth heater 348 may be located beneath a portion of the swab surface 310 arranged and adapted to hold or contain the sample 311. The fourth heater 348 may comprise a wire heater (e.g., a tungsten wrap) and/or may be configured to heat the sample 311 and/or swab surface 310 and/or the solvent to at least 50° C., 100° C., 200° C., 300° C., 400° C., 500° C., 600° C., 700° C. or 800° C.

The swab itself may be heated so as to heat the sample 311 that is located on the swab. For example, the fourth heater 348 may be a wire heater that is located within the swab, and may be arranged and adapted to heat the end of the swab configured to hold and/or retain biologic samples for analysis.

The impact of heating an ion inlet transfer capillary (such as a transfer capillary or transfer device 330 as shown in FIG. 25A) was tested on a Xevo G2-XS® quadrupole Time of Flight mass spectrometer and a Synapt G2-Si® quadrupole-ion mobility-Time of Flight mass spectrometer.

The ion transfer capillary or transfer device 330 was heated using a nickel wire heater in a range from 100 to 490° C. Pork liver sections were used and the intensities for selected fatty acids and phospholipids were compared. Inlet capillary heating was found to have some impact on fatty acid intensities using a Xevo® mass spectrometer and no impact using a Synapt® mass spectrometer. Intensities for the monitored phospholipids, however, could be improved by almost two orders of magnitude.

Figure 25B:
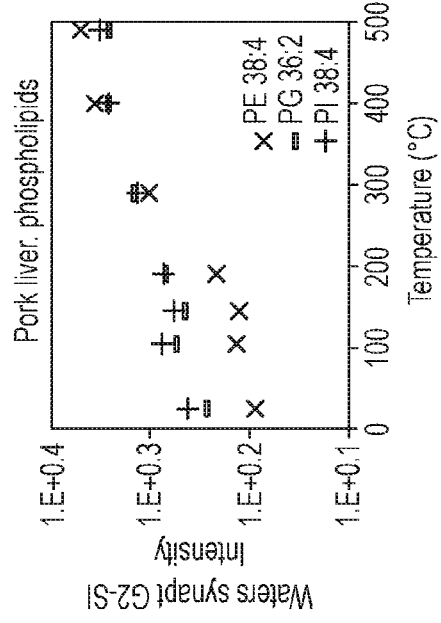
FIG. 25B shows a graph of intensity versus inlet capillary temperature for analysis of fatty acids using a Waters Synapt® mass spectrometer.
Figure 25D:
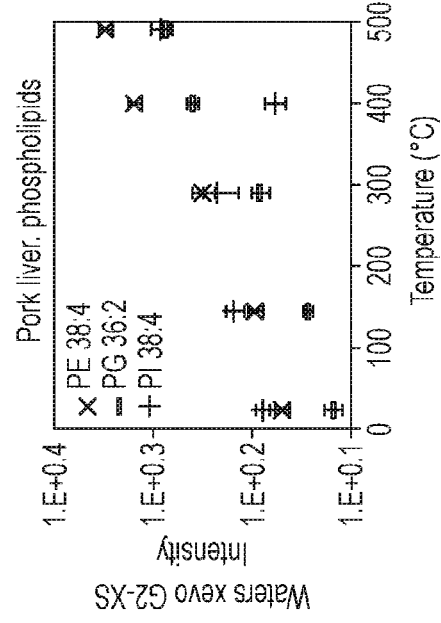
FIG. 25D shows a graph of intensity versus inlet capillary temperature for analysis of phospholipids using a Waters Synapt® mass spectrometer and FIG. 25E shows a graph of intensity versus inlet capillary temperature for analysis of phospholipids using a Waters Xevo® mass spectrometer.
Figure 25C:
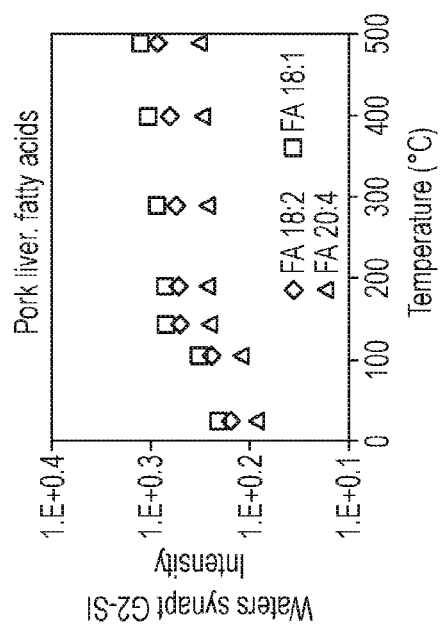
FIG. 25C shows a graph of intensity versus inlet capillary temperature for analysis of fatty acids using a Waters Xevo® mass spectrometer.
Figure 25E:
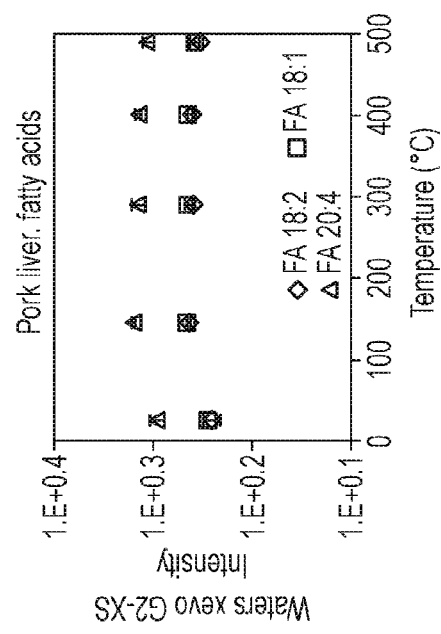

FIGS. 25B-E show the impact of inlet capillary heating on absolute intensity. FIGS. 25B and 25D relate to a Waters Synapt G2-Si® mass spectrometer and FIGS. 25C and 25E relate to a Waters Xevo G2-XS® mass spectrometer. Average intensities for selected fatty acids (FA), phosphatidyl ethanolamines (PE) and the most abundant phosphatidylinositol (PI) from pork liver sections are shown.

It is apparent from FIGS. 25B-E that increasing the temperature of the ion transfer capillary or transfer device 330 can increase the observed intensity of phospholipids by nearly two orders of magnitude.

Ambient Ionisation Analysis of Biopsy Samples

A number of further embodiments relate to the use of ambient ionisation mass spectrometry, and in particular rapid evaporative ionisation mass spectrometry ("REIMS") and desorption electrospray ionisation ("DESI") mass spectrometry, in the analysis of biopsy samples.

A biopsy sample is a sample of cells or tissue that is typically taken from a living subject and used to determine the presence or extent of a disease.

Biopsy samples can be provided using, e.g., (i) fine needle aspiration biopsy, where a thin needle attached to a syringe is used to aspirate a small amount of tissue, (ii) a core needle biopsy, where a hollow needle is used to withdraw cylinders (or cores) of tissue, and (iii) a surgical (or open) biopsy, where tissue is surgically cut e.g. using a scalpel. A biopsy may optionally be incisional, excisional, or be retrieved from a surgical resection. A biopsy specimen comprises cells and may optionally be a tissue specimen, for example, comprising or consisting of diseased and/or non-diseased tissue.

Figure 26:
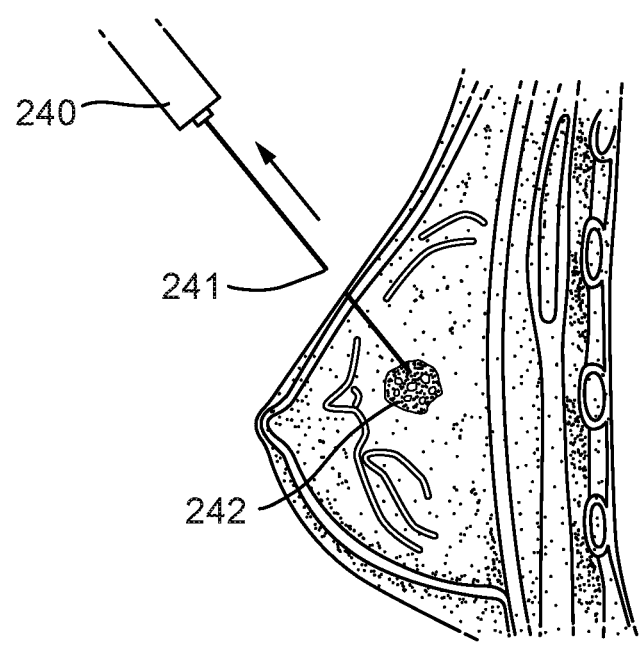
FIG. 26 shows a needle biopsy procedure in which a biopsy needle is used to extract a biopsy core from a patient.

FIG. 26 illustrates a typically core needle biopsy, in which a biopsy needle 240 comprising a hollow needle is used to withdraw cylinders (or cores) 241 of tissue, e.g. including a tumour 242 or other area of medical interest.

Conventional histopathological analysis of biopsy samples involves sending the sample to a specialist lab, where the sample is prepared for examination, and examined under a microscope. Accordingly, conventional biopsy analysis involves a time consuming and costly workflow.

According to various embodiments, a biopsy sample is analysed using ambient ionisation mass spectrometry, and in particular rapid evaporative ionisation mass spectrometry ("REIMS") and/or desorption electrospray ionisation mass spectrometry ("DESI-MS").

The Applicants have found that ambient ionisation mass spectrometry, and in particular rapid evaporative ionisation mass spectrometry ("REIMS") analysis and desorption electrospray ionisation ("DESI") mass spectrometry analysis, of biopsy samples can produce pathologically relevant information. Moreover, ambient ionisation mass spectrometry, and in particular rapid evaporative ionisation mass spectrometry ("REIMS") analysis and desorption electrospray ionisation ("DESI") mass spectrometry analysis, can provide rapid, real-time, point-of-care information in a particularly convenient and efficient manner.

A particularly useful feature of rapid evaporative ionisation mass spectrometry ("REIMS") analysis and desorption electrospray ionisation ("DESI") mass spectrometry analysis of biopsy samples is the relative ease of acquiring spatially resolved data using these techniques.

In particular, spatially resolved information from a biopsy sample may be used to determine the presence, location and/or extent or size of diseased tissue, e.g., a tumour and/or necrotic tissue in a biopsy sample.

In this regard, the Applicants have found that methods according to various embodiments can give more accurate data when compared with, for example, magnetic resonance imaging ("MRI") of tumours. In one particular embodiment, this may be exploited to accurately determine whether or not the location of a tumour (e.g. close to a vein or otherwise) renders the tumour inoperable, e.g. prior to an operation. In another embodiment, this may be used to determine how much diseased tissue, e.g. necrotic or cancerous tissue, needs to be, or safely can be, removed.

Spatially resolved information from a biopsy sample may additionally or alternatively be used in determining the aggressiveness of a tumour and/or the likelihood that or degree to which a tumour will respond to a particular treatment. For example, by analysing portions of a biopsy sample adjacent to a tumour, information regarding the body's natural response to the tumour can be determined, e.g. by identifying relevant biomarkers. This information can be directly related to the aggressiveness of a tumour and/or the likelihood that or degree to which a tumour will respond to a particular treatment.

The analysis may optionally be used to identify disease margins. A disease margin may optionally be analysed, e.g., by analysing the concentration of a particular cell type, e.g. a diseased, cancerous, and/or necrotic cell type, in a target region.

According to various other embodiments, information obtained from the analysis of a biopsy sample may be used, e.g. in real-time while a patient is under anaesthesia and/or during surgery, to determine a course of action.

Biopsy Analyser

According to an embodiment, a biopsy needle may be inserted into a patient and then the resulting biopsy sample (e.g. biopsy core) may be inserted into a dedicated channel of a mass and/or ion mobility spectrometer.

The biopsy sample may be inserted into the channel of the mass and/or ion mobility spectrometer together with the biopsy needle (i.e. that was used to extract the sample), by itself, or together with some other device for holding and/or supporting the biopsy sample.

The mass and/or ion mobility spectrometer may then analyse the sample. The mass and/or ion mobility spectrometer may, for example, perform longitudinal analysis of the biopsy needle or sample, i.e., along the length of the biopsy needle or sample.

According to various embodiments, a one-dimensional (e.g. longitudinal) mass spectrometry image or ion image of a biopsy sample may be provided.

Rapid evaporative ionisation mass spectrometry ("REIMS") and desorption electrospray ionisation mass spectrometry ("DESI-MS") are both particularly suited to the analysis of biopsy samples in these embodiments, as they can be readily used to provide spatially resolved mass spectral data, i.e. to provide a one-dimensional (longitudinal) mass spectrometry image or ion image of a biopsy sample or core.

In various embodiments, the mass spectral analysis, e.g. including a diagnosis, may be performed in real-time and/or at the point of care ("POC"). This represents a fast and convenient method for analysing biopsy samples.

If any issues arise from the mass analysis of the biopsy needle then a second biopsy may immediately be performed, thereby beneficially saving the patient from having to undergo a second biopsy procedure at a later date.

These embodiments are particularly relevant, for example, for liver and kidney biopsies. In these cases, the current medical practice is to insert a catheter through the neck and to use a snare to (hopefully) capture a piece of liver or kidney. As such, various embodiments represent an improved method for liver and kidney biopsies.

Biopsy Needle

According to various embodiments a biopsy needle may be provided that is arranged to collect two (or more) separate samples or portions of a biopsy sample (e.g. two (or more) biopsy cores or cylinders) at the same time. The biopsy needle may be configured such that when it is inserted into tissue, two (or more) separate samples or portions of the tissue (e.g. two (or more) biopsy cores or cylinders) are produced.

The biopsy needle may comprise, for example, a needle comprising a first hollow tube or cylinder and a second hollow tube or cylinder. The first and second hollow tubes or cylinders may be conjoined, e.g. along some, most or all of the axial length of the first and/or second hollow tube or cylinder.

The two separate samples or portions of the tissue (e.g. the two biopsy cores or cylinders) produced by the biopsy needle may comprise adjacent portions of tissue. For example, two biopsy cores or cylinders may be produced where the first biopsy core or cylinder comprises tissue that was originally adjacent and/or connected to the tissue of the second biopsy core or cylinder, i.e. along some, most or all the axial length of the first and/or second biopsy core or cylinder.

According to an embodiment one of the two samples may be sent for conventional histopathological analysis and the second of the samples may be (e.g. substantially immediately) subjected to ambient ionisation mass spectrometry, and in particular to rapid evaporative ionisation mass spectrometry ("REIMS") analysis and/or desorption electrospray ionisation ("DESI") analysis.

Beneficially, ambient ionisation mass spectrometry, and in particular rapid evaporative ionisation mass spectrometry ("REIMS") and/or desorption electrospray ionisation ("DESI") analysis is able to provide additional information to the information provided by histopathology. In particular, rapid evaporative ionisation mass spectrometry ("REIMS")

can potentially identify the underlying disease whereas histopathology is only able to provide information relating to the cell chemistry.

An example application according to an embodiment is the diagnosis of non-alcoholic fatty liver disease ("NAFLD").

Rapid Evaporative Ionisation Mass Spectrometry ("REIMS") Biopsy

According to various embodiments, a biopsy needle may be provided which comprises a device that is configured to generate aerosol, smoke or vapour from a target. The device may comprise or form part of an ambient ion or ionisation source, or the device may generate the aerosol, smoke or vapour for subsequent ionisation by an ambient ion or ionisation source or other ionisation source.

According to one particular embodiment, a biopsy needle may be provided which comprises one or more electrodes, and in particular one or more rapid evaporative ionisation mass spectrometry ("REIMS") electrodes.

According to another embodiment a biopsy needle may be provided that comprises a laser ionisation ion source, e.g. as describe above. According to another embodiment a biopsy needle may be provided that comprises an ultrasonic ablation ion source, e.g. as describe above.

The device or electrode(s) may be activated while the biopsy needle is inserted into a patient, e.g. to provide mass spectral data relating to the tissue samples by the biopsy needle.

A patient undergoing a biopsy using a needle which includes an ambient ion source such as a rapid evaporative ionisation mass spectrometry ("REIMS") electrode would require an anaesthetic, but various embodiments have a number of applications including real time diagnosis and analysis of a disease such as any of the diseases mentioned elsewhere herein, e.g., hepatitis, liver sclerosis and cancerous tissue.

According to another embodiment, the device or electrode(s) may be activated once the biopsy needle containing a biopsy sample (core) has been extracted from the patient.

According to various embodiments, the biopsy needle may comprise a biopsy needle that is arranged to collect two (or more) separate samples or portions of a biopsy sample (e.g. two (or more) biopsy cores or cylinders) at the same time, e.g. as described above. In these embodiments, the device or electrode(s) may be configured to (e.g. selectively) generate aerosol, smoke or vapour from one or both of the biopsy samples. Where the device or electrode(s) is configured to generate aerosol, smoke or vapour from only one of the biopsy samples, then the other biopsy sample may be sent for conventional histopathological analysis, e.g. as described above.

Figure 27:
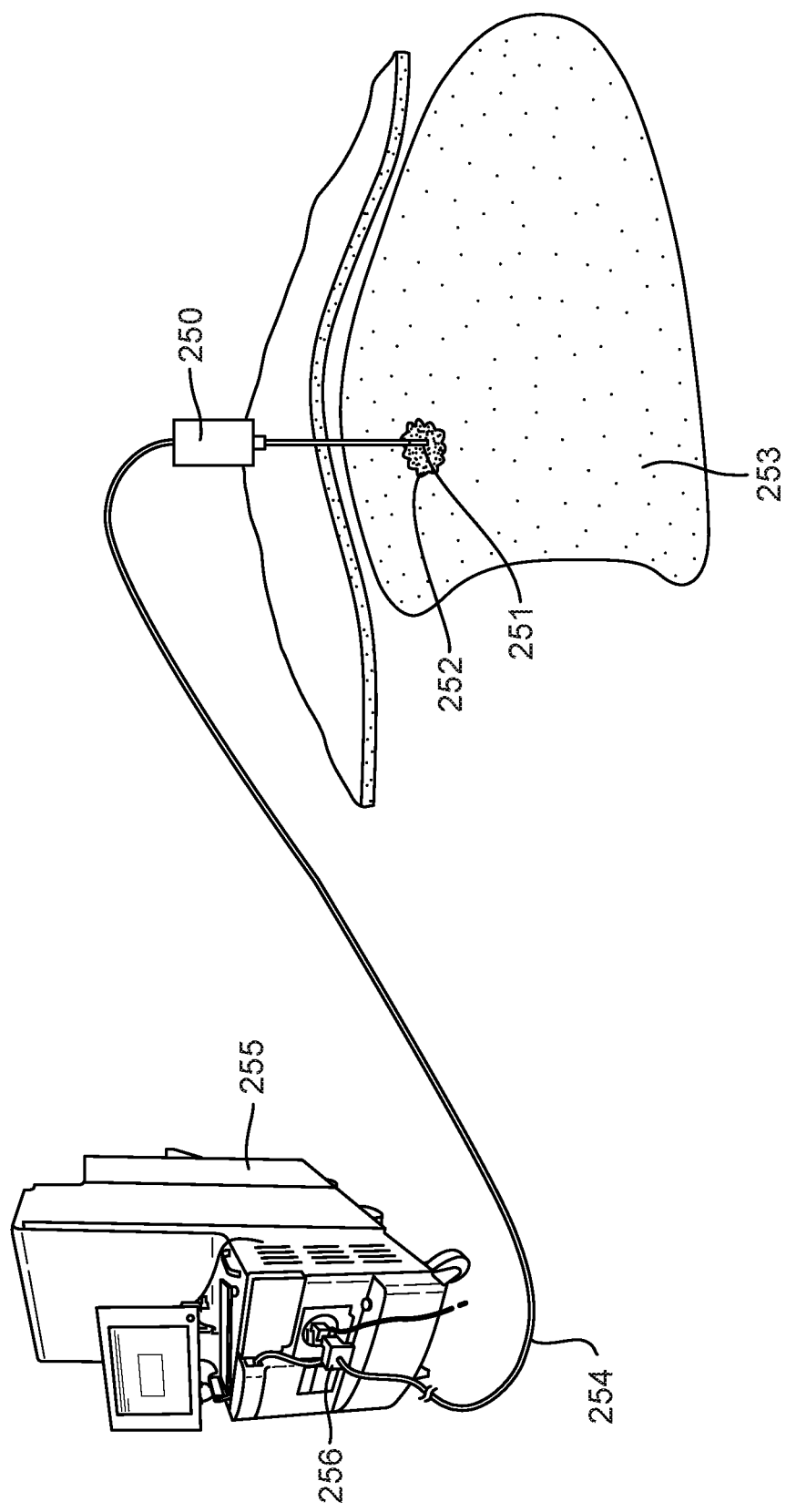
FIG. 27 shows a biopsy needle comprising a rapid evaporative ionisation mass spectrometry ("REIMS") electrode in accordance with an embodiment.

FIG. 27 shows an embodiment wherein a biopsy needle 250 is provided with an electrode 251 which may be at the distal end of the needle 250. In the embodiment illustrated in FIG. 26, the biopsy needle has been inserted into a tumour 252 present within an internal organ 253 of a patient.

The electrode 251 is connected to an RF voltage generator (not shown). When an RF voltage is applied to the electrode 251, the electrode 251 acts as an electrosurgical tool and effectively cuts the tumour 252. This causes surgical smoke or aerosol to be generated.

The surgical smoke or aerosol is aspirated into tubing 254, e.g. via one or more fenestrations or aspiration ports (not shown), and along the length of the tubing 254, and is passed to a vacuum chamber of a mass and/or ion mobility spectrometer 255 via an atmospheric inlet 256. Aspiration of the surgical smoke or aerosol may be facilitated using a Venturi pump, e.g. driven by standard medical air or nitrogen.

The surgical smoke or aerosol may then be ionised, e.g. by impacting a collision surface which may be heated.

The resulting analyte ions may then be analysed, e.g. mass analysed and/or subjected to ion mobility analysis or separation and real time information relating to the tissue or tumour 252 may be provided to a user.

The mass and/or ion mobility spectrometer 255 may include a modified atmospheric interface 256 which includes a collision surface which may be positioned along and adjacent to the central axis of the large opening of a StepWave® ion guide. As will be understood by those skilled in the art, a StepWave® ion guide comprises two conjoined ion tunnel ion guides. Each ion guide comprises a plurality of ring or other electrodes wherein ions pass through the central aperture provided by the ring or other electrodes. Transient DC voltages or potentials are applied to the electrodes. The StepWave® ion guide is based on stacked ring ion guide technology and is designed to maximise ion transmission from the source to the mass analyser or filter. The device allows for the active removal of neutral contaminants thereby providing an enhancement to overall signal to noise. The design enables the efficient capture of the diffuse ion cloud entering a first lower stage which is then focused into an upper ion guide for transfer to the mass analyser or filter.

The collision surface which may be located within a vacuum chamber of the mass and/or ion mobility spectrometer 255 facilitates efficient fragmentation of molecular clusters formed in the free jet region of the atmospheric interface 256 due to the adiabatic expansion of gas entering the vacuum chamber and the resulting drop in temperature. The surface-induced dissociation of supramolecular clusters improves the signal intensity and also alleviates the problems associated with the contamination of ion optics.

The biopsy needle may be used in any part of the body or organs such as the lung, liver and breast.

The biopsy needle may comprise a monopolar device and a relatively large pad acting as a return electrode may be placed underneath the patient so that electrical current flows from the electrode 251, through the patient, to the return electrode. Alternatively, the biopsy needle may comprise a bipolar device, e.g. comprising two electrodes, such that electrical current does not flow through the patient's body. A bipolar biopsy needle may be used, for example, where it is undesirable for an electrical current to flow through surrounding tissue.

Although a monopolar or a bipolar electrode arrangement is particularly beneficial, other embodiments are also contemplated wherein the biopsy needle may comprise a multiphase or 3-phase device and may comprise, for example, three or more separate electrodes.

A matrix may be added or mixed with the surgical smoke or aerosol prior to the surgical smoke or aerosol impacting upon the collision surface. The matrix may comprise a solvent for the surgical smoke or aerosol, and may comprise an organic solvent and/or a volatile compound. The matrix may comprise polar molecules, water, one or more alcohols, methanol, ethanol, isopropanol, acetone or acetonitrile. Isopropanol is particularly beneficial to use.

The matrix which is added may additionally or alternatively comprise a lockmass, lock mobility or calibration compound.

The addition of a matrix is particularly beneficial in that dissolving analyte in the matrix eliminates intermolecular bonding between the analyte molecules. As such, when the dissolved analyte is collided with the collision surface, the dissolved analyte will fragment into droplets and any given droplet is likely to contain fewer analyte molecules than it would if the matrix were not present. This in turn leads to a more efficient generation of ions when the matrix in each droplet is evaporated.

According to various embodiments, the data obtained from the rapid evaporative ionisation mass spectrometry ("REIMS") analysis of the biopsy sample within the biopsy needle 250 may be used to ensure that the biopsy needle has correctly sampled a portion of tissue of interest, e.g. a portion of a tumour 252, e.g. to ensure that the needle has been inserted to the correct depth within the patient, before the biopsy needle 250 is removed from the patient.

Additionally or alternatively, the data obtained from the rapid evaporative ionisation mass spectrometry ("REIMS") analysis of the biopsy sample within the biopsy needle 250 may be used for diagnosis or characterisation, e.g. of the tissue or tumour 252.

The data obtained from the REI rapid evaporative ionisation mass spectrometry ("REIMS") analysis of the biopsy sample within the biopsy needle 250 may be used on its own, or may be used to supplement subsequent analysis (e.g. histopathological analysis) of the (e.g. remaining) biopsy sample (core).

Use of Biopsy Data to Improve Subsequent Real Time Analysis of Surgical Data Obtained Using an Ambient Ionisation Surgical Tool During a Subsequent Surgical Procedure According to various embodiments, pre-operative characterisation of biopsy data may be used to improve a surgical library which may then be subsequently interrogated or used by an ambient ionisation surgical tool, e.g. during the course of a subsequent surgical procedure.

For example, based upon the results of a biopsy analysis, subsequent mass spectral data obtained during a surgical procedure may be obtained and/or analysed in an improved or optimal manner.

For example, if a biopsy revealed that a patient was suffering from liver sclerosis then a subsequent surgical procedure on a portion of the liver may be performed wherein the mass spectral analysis of sample liver tissue is optimised to distinguish between healthy liver tissue and sclerotic liver tissue. This applies mutatis mutandis to any other suitable diseases, e.g., the other diseases mentioned elsewhere herein, particularly cancer, necrosis and the like.

It is contemplated that pre-existing surgical mass spectral (and/or ion mobility) databases, such as proprietary surgical mass spectral (and/or ion mobility) databases, may be provided, and that before a surgical procedure is performed an appropriate surgical database may be pre-loaded, e.g. into a mass spectrometer (and/or ion mobility analyser) which is coupled to the ambient ionisation surgical tool. The database may then be improved or optimised using biopsy data in accordance with various embodiments.

Optimised Operational Parameters of an Ambient Ionisation Surgical Tool May be Programmed or Set Dependent Upon Previously Acquired Data Such as Biopsy Data According to various embodiments one or more operational parameters of an ambient ionisation surgical or diagnostic tool may be arranged to vary or otherwise be optimised during a surgical or diagnostic procedure. This may be done of the basis of previously acquired data such as biopsy data.

For example, according to an embodiment the energy dissipated into surrounding tissue may be arranged to reduce as the surgical or diagnostic device approaches a vital organ.

According to various embodiments, one or more operational parameters of an ambient ionisation surgical tool may be set based upon previously acquired data such as biopsy data.

For example, one or more operational parameters of an ambient ionisation surgical tool may be set based upon the type or grade of cancerous tissue identified during a biopsy or based upon the nature of the diseased tissue identified during a biopsy.

In these embodiments, the cancerous biological tissue or the tumour may comprise, for example: (i) grade I, grade II, grade III or grade IV cancerous tissue; (ii) metastatic cancerous tissue; (iii) mixed grade cancerous tissue; or (iv) a sub-grade cancerous tissue.

Different operational parameters may be used depending upon the type of tissue being operated on, such as depending on whether healthy tissue, clearly diseased (e.g. cancerous) tissue or tissue at the disease (e.g. cancer) margin is being operated on.

According to various embodiments the biopsy data may include spatial information and hence the variation of tissue as a function of depth within an organ may be determined. Accordingly, previously acquired biopsy data may be used to set various operational parameters of an ambient ionisation surgical tool, e.g., as the surgical tool moves deeper into an organ.

Furthermore, various ionisation parameters may be varied, e.g. as the ambient ionisation surgical tool moves deeper into an organ.

For example, as an ambient ionisation surgical tool makes an initial cut into an organ, one or more ionisation parameters (e.g., composition of matrix added to aerosol, smoke or vapour released from the tissue, temperature of an ionisation collision surface, voltage applied to an ionisation collision surface, etc.) may be optimised for the surgical conditions (e.g., initial blood loss, tissue composition, etc.) experienced when initially cutting into the organ. As the ambient ionisation surgical tool moves deeper into the organ the optimum ionisation parameters for the surgical tool may change reflecting, e.g., a different degree of blood and a different composition of the tissue. Accordingly, one or more ionisation parameters (e.g., composition of matrix added to aerosol, smoke or vapour released from the tissue, temperature of an ionisation collision surface, voltage applied to an ionisation collision surface, etc.) may be arranged to also change to match the changing surgical conditions.

Numerous different embodiments are contemplated wherein various operational parameters of a surgical device such as an ambient ionisation ion source (e.g. a rapid evaporative ionisation mass spectrometry ("REIMS") ion source) may be varied on the basis of previously acquired data such as biopsy data.

Analysing Sample Spectra

A list of analysis techniques which may be used in accordance with various embodiments is given in the following table:

Analysis Techniques
Univariate Analysis
Multivariate Analysis
Principal Component Analysis (PCA)
Linear Discriminant Analysis (LDA)
Maximum Margin Criteria (MMC)
Library Based Analysis
Soft Independent Modelling Of Class Analogy (SIMCA)
Factor Analysis (FA)
Recursive Partitioning (Decision Trees)
Random Forests Independent Component Analysis (ICA)
Partial Least Squares Discriminant Analysis (PLS-DA)
Orthogonal (Partial Least Squares) Projections To Latent Structures (OPLS)
OPLS Discriminant Analysis (OPLS-DA)
Support Vector Machines (SVM)
(Artificial) Neural Networks
Multilayer Perceptron
Radial Basis Function (RBF) Networks
Bayesian Analysis
Cluster Analysis
Kernelized Methods
Subspace Discriminant Analysis
K-Nearest Neighbours (KNN)
Quadratic Discriminant Analysis (QDA)
Probabilistic Principal Component Analysis (PPCA)
Non negative matrix factorisation
K-means factorisation
Fuzzy c-means factorisation
Discriminant Analysis (DA)

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

Figure 28:
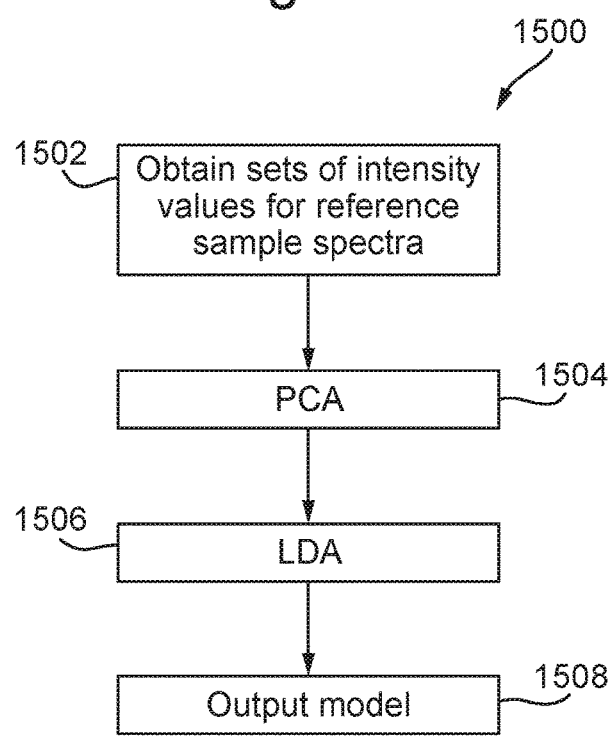
FIG. 28 shows a method of analysis that comprises building a classification model according to various embodiments.

FIG. 28 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows a sample (such as an aerosol, smoke or vapour sample, a biological sample, etc.) to be classified using one or more sample spectra obtained from the sample. The multivariate analysis will now be described in more detail with reference to a simple example.

Figure 29:
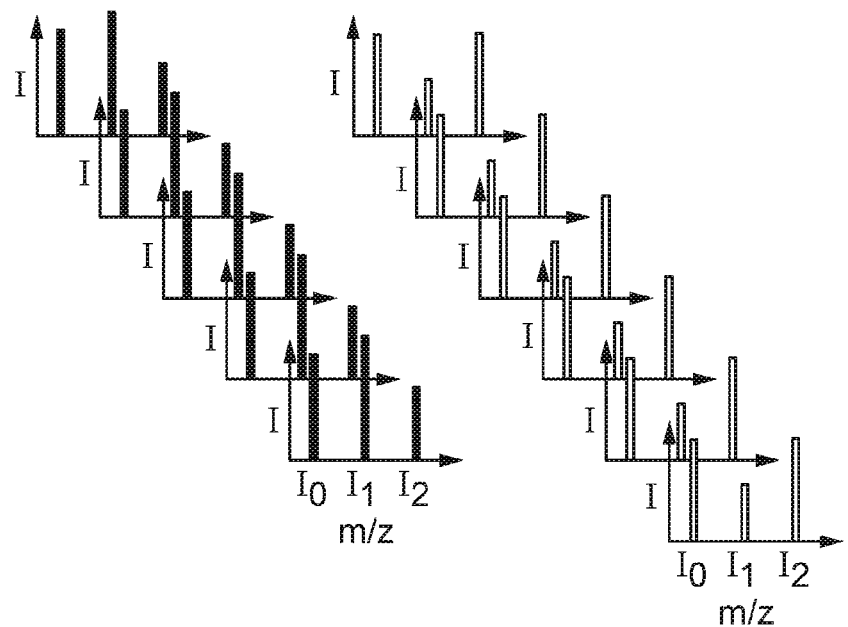
FIG. 29 shows a set of reference sample spectra obtained from two classes of known reference samples.

FIG. 29 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been preprocessed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 30:
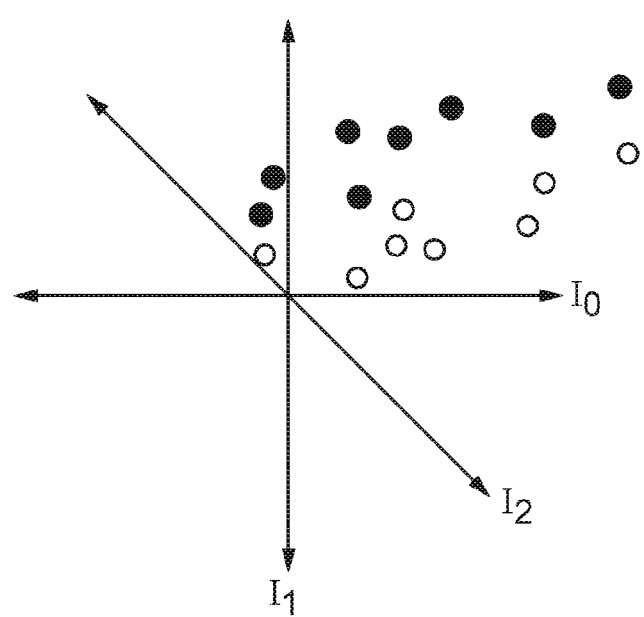
FIG. 30 shows a multivariate space having three dimensions defined by intensity axes, wherein the multivariate space comprises plural reference points, each reference point corresponding to a set of three peak intensity values derived from a reference sample spectrum.

FIG. 30 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 31:
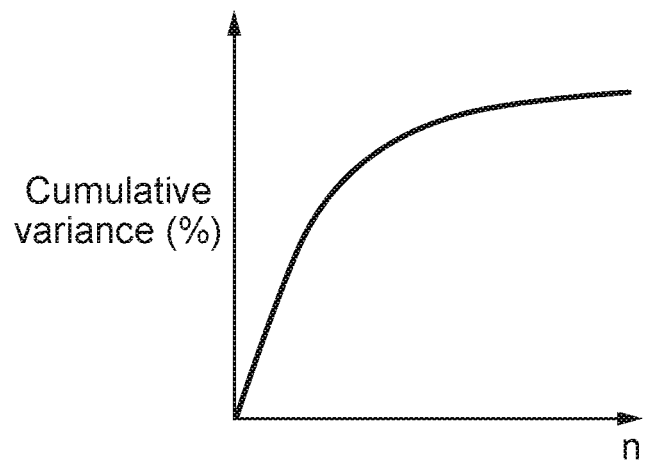
FIG. 31 shows a general relationship between cumulative variance and number of components of a PCA model.

FIG. 31 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \qquad (1)$$

Figure 32:
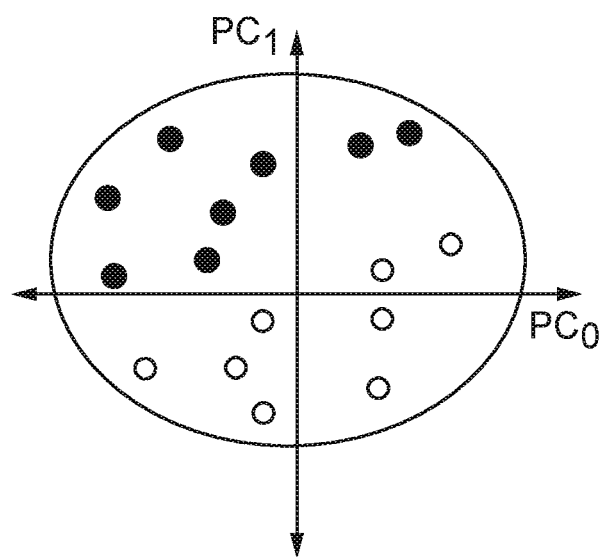
FIG. 32 shows a PCA space having two dimensions defined by principal component axes, wherein the PCA space comprises plural transformed reference points or scores, each transformed reference point or score corresponding to a reference point of FIG. 30.

FIG. 32 shows the resultant PCA space for the reference sample spectra of FIGS. 29 and 30. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 29 and therefore to a reference point of FIG. 30.

As is shown in FIG. 32, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z=SU \qquad (2)$$

where the matrix Z contains the scores transformed into the LDA space.

Figure 33:
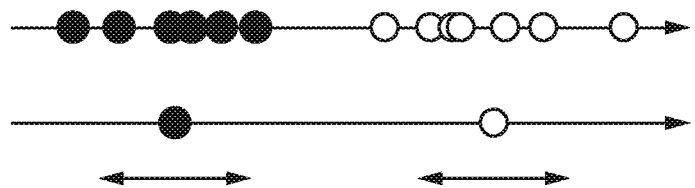
FIG. 33 shows a PCA-LDA space having a single dimension or axis, wherein the LDA is performed based on the PCA space of FIG. 32, the PCA-LDA space comprising plural further transformed reference points or class scores, each further transformed reference point or class score corresponding to a transformed reference point or score of FIG. 32.

FIG. 33 shows a PCA-LDA space having a single dimension or axis, wherein the LDA is performed in the PCA space of FIG. 32. As is shown in FIG. 33, the LDA space comprises plural further transformed reference points or PCA-LDA scores, with each further transformed reference point corresponding to a transformed reference point or PCA score of FIG. 32.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by $$V'_g = U^T V_g U \qquad (3)$$

where $V_g$ are the class covariance matrices in the PCA space.

The transformed class average position $z_g$ for class g may be given by $$s_g U = z_g \qquad (4)$$

where $s_g$ is the class average position in the PCA space.
Multivariate Analysis—Using a Model for Classification By way of example, a method of using a classification model to classify a sample (such as an aerosol, smoke or vapour sample) will now be described.

Figure 34:
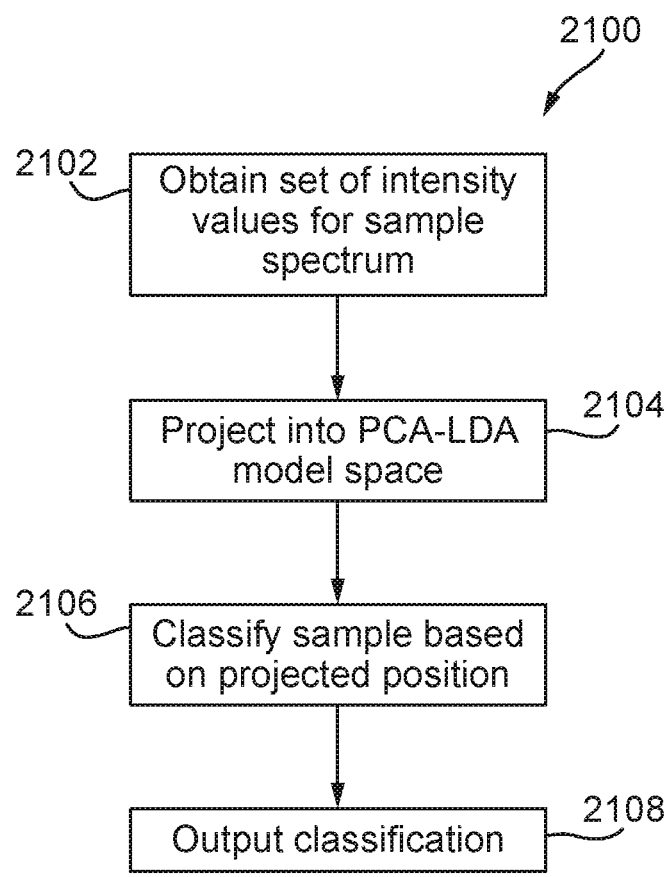
FIG. 34 shows a method of analysis that comprises using a classification model according to various embodiments.

FIG. 34 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of a sample (e.g. an aerosol, smoke or vapour sample) will now be described in more detail with reference to the simple PCA-LDA model described above.

Figure 35:
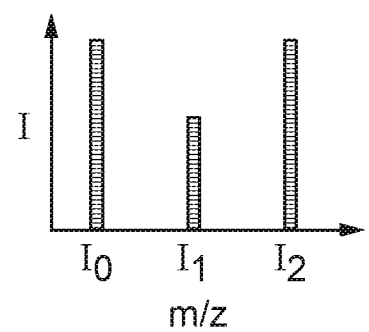
FIG. 35 shows a sample spectrum obtained from an unknown sample.

FIG. 35 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_X$, with the elements of the vector being the peak-intensity values for the respective mass to charge ratios. A transformed PCA vector $s_X$ for the sample spectrum can be obtained as follows:

$$d_X L = s_X \qquad (5)$$

Then, a transformed PCA-LDA vector $z_X$ for the sample spectrum can be obtained as follows:

$$s_X U = z_X \qquad (6)$$

Figure 36:
FIG. 36 shows the PCA-LDA space of FIG. 33, wherein the PCA-LDA space further comprises a PCA-LDA projected sample point derived from the peak intensity values of the sample spectrum of FIG. 35.

FIG. 36 again shows the PCA-LDA space of FIG. 33. However, the PCA-LDA space of FIG. 36 further comprises the projected sample point, corresponding to the transformed PCA-LDA vector $z_X$, derived from the peak intensity values of the sample spectrum of FIG. 35.

In this example, the projected sample point is to one side of a hyperplane between the classes that relates to the right-hand class, and so the sample (aerosol, smoke or vapour sample) may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \qquad (8)$$

and the data vector $d_x$ may be assigned to the class for which this distance is smallest.

In addition, treating each class as a multivariate Gaussian, a probability of membership of the data vector to each class may be calculated.
Library Based Analysis—Developing a Library for Classification By way of example, a method of building a classification library using plural input reference sample spectra will now be described.

Figure 37:
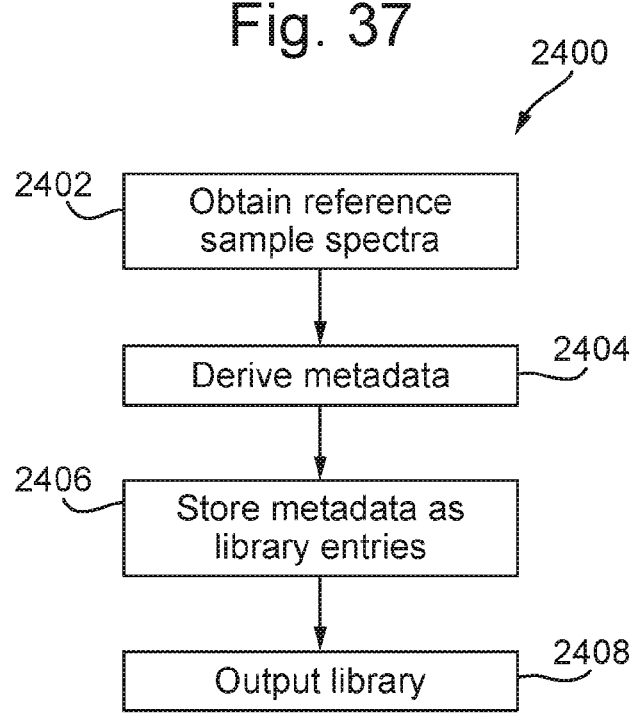
FIG. 37 shows a method of analysis that comprises building a classification library according to various embodiments.

FIG. 37 shows a method 2400 of building a classification library. In this example, the method comprises a step 2402 of obtaining plural input reference sample spectra and a step 2404 of deriving metadata from the plural input reference sample spectra for each class of sample. The method then comprises a step 2404 of storing the metadata for each class of sample as a separate library entry. The classification library is then output, for example to electronic storage, in step 2406.

A classification library such as this allows a sample (e.g. an aerosol, smoke or vapour sample) to be classified using one or more sample spectra obtained from the sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \left\lfloor N_{chan} \log \frac{m}{M_{min}} \Big/ \log \frac{M_{max}}{M_{min}} \right\rfloor \quad (7)$$

where $N_{chan}$ is a selected value and $\lfloor x \rfloor$ denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5.

A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_1$. In one example, $\bar{y}_i=1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i | \mu_i, D_i) = \frac{1}{D_i} \frac{C^{C-1/2} \Gamma(C)}{\sqrt{\pi} \, \Gamma(C-1/2)} \frac{1}{\left(C + \frac{(y_i - \mu_i)^2}{D_i^2}\right)^C} \quad (8)$$

where $\frac{1}{2} \leq C < \infty$ and where $\Gamma(C)$ is the gamma function.

The above equation is a generalised Cauchy distribution which reduces to a standard Cauchy distribution for C=1 and becomes a Gaussian (normal) distribution as C→∞. The parameter $D_i$ controls the width of the distribution (in the Gaussian limit $D_i=\sigma_i$ is simply the standard deviation) while the global value C controls the size of the tails.

In one example, C is 3/2, which lies between Cauchy and Gaussian, so that the likelihood becomes:

$$Pr(y_i | \mu_i, D_i) = \frac{3}{4} \frac{1}{D_i} \frac{1}{(3/2 + (y_i - \mu_i)^2 / D_i^2)^{3/2}} \quad (9)$$

For each library entry, the parameters $\mu_i$ are set to the median of the list of values in the i'th channel of the input reference sample spectra while the deviation $D_i$ is taken to be the interquartile range of these values divided by √2. This choice can ensure that the likelihood for the i'th channel has the same interquartile range as the input data, with the use of quantiles providing some protection against outlying data.

Library Based Analysis—Using a Library for Classification

By way of example, a method of using a classification library to classify a sample (e.g. an aerosol, smoke or vapour sample) will now be described.

Figure 38:
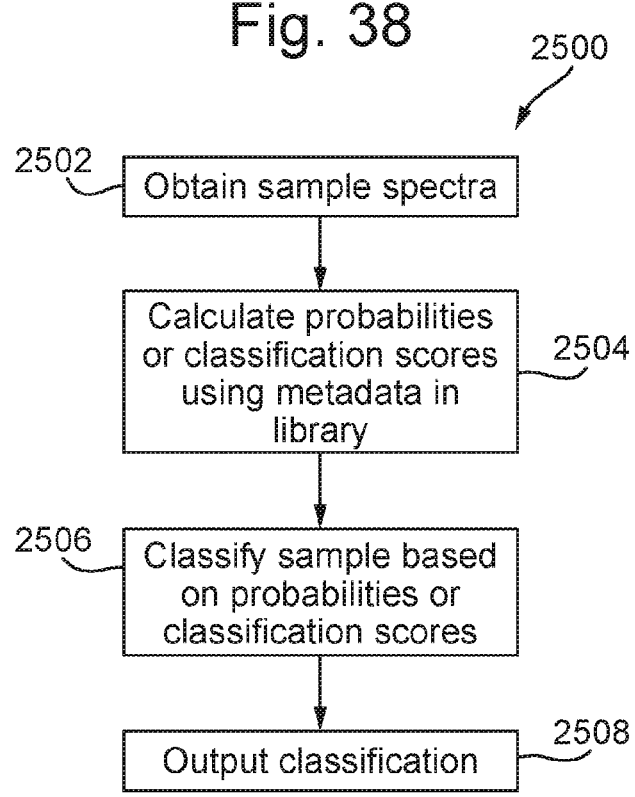
FIG. 38 shows a method of analysis that comprises using a classification library according to various embodiments.

FIG. 38 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of a sample (e.g. an aerosol, smoke or vapour sample) will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y|\mu, D) = \Pi_{i=1}^{N_{chan}} Pr(y_i | \mu_i, D_i) \quad (10)$$

where $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class $\tilde{s}$ is given by:

$$Pr(\tilde{s} | y) = \frac{L_{\tilde{s}}^{(1/F)}}{\sum_s L_s^{(1/F)}} \quad (11)$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}} \quad (12)$$

Again, the scores $R_s$ are normalised over all candidate classes 's'.

The sample (e.g. aerosol, smoke or vapour sample) may then be classified as belonging to the class having the highest probability and/or highest RMS classification score.

Methods of Analysis, e.g., Methods of Medical Treatment, Surgery and Diagnosis and Non-Medical Methods Various different embodiments are contemplated. According to some embodiments the methods disclosed above may be performed on in vivo, ex vivo or in vitro tissue. The tissue may comprise human or non-human animal tissue. Embodiments are contemplated wherein the target may comprise biological tissue, a bacterial or fungal colony or more generally an organic target such as a plastic).

Various embodiments are contemplated wherein analyte ions generated by an ambient ionisation ion source are then subjected either to: (i) mass analysis by a mass analyser or filter such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly (or vice versa) ion mobility analysis (IMS) and/or differential ion mobility analysis (DMA) and/or Field Asymmetric Ion Mobility Spectrometry (FAIMS) analysis followed by secondly (or vice versa) mass analysis by a mass analyser or filter such as a quadrupole mass analyser or a Time of Flight mass analyser. Various embodiments also relate to an ion mobility spectrometer and/or mass analyser and a method of ion mobility spectrometry and/or method of mass analysis. Ion mobility analysis may be performed prior to mass to charge ratio analysis or vice versa.

Various references are made in the present application to mass analysis, mass analysers, mass analysing, mass spectrometric data, mass spectrometers and other related terms referring to apparatus and methods for determining the mass or mass to charge of analyte ions. It should be understood that it is equally contemplated that the present invention may extend to ion mobility analysis, ion mobility analysers, ion mobility analysing, ion mobility data, ion mobility spectrometers, ion mobility separators and other related terms referring to apparatus and methods for determining the ion mobility, differential ion mobility, collision cross section or interaction cross section of analyte ions. Furthermore, it should also be understood that embodiments are contemplated wherein analyte ions may be subjected to a combination of both ion mobility analysis and mass analysis i.e. that both (a) the ion mobility, differential ion mobility, collision cross section or interaction cross section of analyte ions together with (b) the mass to charge of analyte ions is determined. Accordingly, hybrid ion mobility-mass spectrometry (IMS-MS) and mass spectrometry-ion mobility (MS-IMS) embodiments are contemplated wherein both the ion mobility and mass to charge ratio of analyte ions generated e.g. by an ambient ionisation ion source are determined. Ion mobility analysis may be performed prior to mass to charge ratio analysis or vice versa. Furthermore, it should be understood that embodiments are contemplated wherein references to mass spectrometric data and databases comprising mass spectrometric data should also be understood as encompassing ion mobility data and differential ion mobility data etc. and databases comprising ion mobility data and differential ion mobility data etc. (either in isolation or in combination with mass spectrometric data).

Various surgical, therapeutic, medical treatment and diagnostic methods are contemplated.

However, other embodiments are contemplated which relate to non-surgical and non-therapeutic methods of mass spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

According to some embodiments the methods disclosed above may be carried out on a "target", which may optionally be a subject or a specimen derived from a subject, e.g. the biological material on a swab or a biopsy specimen.

According to various embodiments the target may comprise biological matter or organic matter (including a plastic). According to various embodiments the target may comprise one or more bacterial colonies and/or one or more fungal colonies.

The "subject" may be a human or a non-human animal. The subject may be alive or dead. If the method is carried out on a living subject, then it may be referred to as an in vivo method. If the method is carried out on a specimen, then it may be referred to as an in vitro or ex vivo method.

Optionally, the non-human animal may be a mammal, optionally selected, for example, from any livestock, domestic or laboratory animal, such as, mice, guinea pigs, hamsters, rats, goats, pigs, cats, dogs, sheep, rabbits, cows, horses and/or monkeys. Optionally, it may be an insect, bird, or fish, e.g. a fly, or a worm.

The method may optionally be carried out on an in vivo target, i.e. on a living subject. For example, it may be carried out by using a thermal ablation method.

Alternatively or in addition, it may optionally be carried out on a dead subject, for example as part of an autopsy or a necropathy.

Alternatively or in addition, it may optionally be carried out on an ex vivo or in vitro target, e.g., on a specimen. The specimen may optionally be a provided specimen, i.e. a specimen that was previously obtained or removed from a subject. Optionally, the method may include a step of obtaining a specimen from a subject. The term "tissue" is used herein interchangeably with "biological tissue" and is used herein to denote a structure of cells, which may optionally be, for example, a structure, an organ, or part of a structure of organ. The tissue may be in vivo, ex vivo or in vitro.

Examples of tissues that may optionally be analysed are adrenal gland tissue, appendix tissue, bladder tissue, bone, bowel tissue, brain tissue, breast tissue, bronchi, ear tissue, oesophagus tissue, eye tissue, endometrioid tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The analysis may optionally relate to a disease or condition, such as, any of the diseases or conditions listed in this section and/or elsewhere herein. The terms "disease" and "condition" are used interchangeably herein.

The disease may be a skin condition, which may optionally be selected, for example, from Acne, Alopecia, Boils, Bowen's Disease, Bullous pemphigoid (BP), Carbuncle, Cellulitis, Chilblains, Cysts, Darier's disease, Dermatitis, Dermatomyositis, Eczema, Erythema, Exanthema, Folliculitis, Frostbite, Herpes, Ichthyosis, Impetigo, Intertrigo, Keratosis, Lichen planus, Linear IgA disease, Melanoma, Moles, Onychomycosis, Papillioma, Petechiae, Prurigo, Psoriasis, Rosacea, Scabies, Scleroderma, Sebaceous Cyst, Shingles/Chickenpox, Telangiectasia, Urticaria (Hives), Warts and/or Xeroderma.

The disease may be a liver condition, which may optionally be selected from, for example, hepatitis, fatty liver disease, alcoholic hepatitis, liver sclerosis and/or cirrhosis. Lung conditions may optionally be selected from, for example, Asthma, Atelectasis, Bronchitis, Chronic obstructive pulmonary disease (COPD), Emphysema, Lung cancer, Pneumonia, Pulmonary edema, Pneumothorax, and/or Pulmonary embolus.

The thyroid gland is an endocrine gland which normally produces thyroxine (T4) and triiodothyronine (T3). The disease may be a thyroid condition, which may optionally be, e.g., hypothyroidism or hyperthyroidism.

The disease may be a cancer or tumour; these terms are used interchangeably herein, The cancer or tumour may optionally be selected from, for example, carcinomas, sarcomas, leukaemias, lymphomas and gliomas.

More particularly, it may optionally be selected from, for example, Acute Lymphoblastic Leukemia (ALL), Acute Myeloid Leukemia (AML), Adrenocortical Carcinoma, adenoma, Anal Cancer, Appendix Cancer, Astrocytomas, Basal Cell Carcinoma, Bile Duct Cancer, Birch-Hirschfield, Blastoma, Bladder Cancer, Bone Cancer, Ewing Sarcoma, Osteosarcoma, Malignant Fibrous Histiocytoma, Brain Stem Glioma, Brain cancer, glioblastoma multiforme ("GBM"), Astrocytomas, Spinal Cord cancer, Craniopharyngioma, Breast Cancer, Bronchial Tumour, Burkitt Lymphoma, Carcinoid Tumour, Cervical Cancer, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Childhood, Ductal Carcinoma In Situ (DCIS), Endometrial Cancer, Ependymoma, Esophageal Cancer, Esthesioneuroblastoma, Fibroadenoma, Intraocular Melanoma, Retinoblastoma, Fallopian Tube Cancer, Gallbladder Cancer, Gastric (Stomach) Cancer, Germinoma, Hairy Cell Leukemia, Head and Neck Cancer, Heart Cancer, Heptacarcinoma, Hodgkin Lymphoma, Hypopharyngeal Cancer, Kahler, Kaposi Sarcoma, Kidney cancer, Laryngeal Cancer, Leiomyoma, Lip and Oral Cavity Cancer, Liver Cancer, Lung Cancer (such as, Non-Small Cell or Small Cell), Lymphoma, Lymphoblastoma, Male Breast Cancer, Malignant Fibrous Histiocytoma of Bone, Melanoma, Melanocarcinoma, Medulloblastoma, Merkel Cell Carcinoma, Mesothelioma, Mouth Cancer, Myeloma, Multiple Myeloma, Mycosis Fungoides, Myeloproliferative disorder, Nasal Cavity and Paranasal Sinus Cancer, Nasopharyngeal Cancer, Neuroblastoma, Nephroblastoma, Non-Hodgkin Lymphoma, Oral Cancer, Oropharyngeal Cancer, Osteosarcoma, Ovarian Cancer, Pancreatic Cancer, Papillomatosis, Paraganglioma, Parathyroid Cancer, Penile Cancer, Peritoneal cancer, Pharyngeal Cancer, Pheochromocytoma, Pineoblastoma, Pituitary Tumour, Prostate Cancer, Rectal Cancer, Retinoblastoma, Rhabdomyosarcoma, Salivary Gland Cancer, Sézary Syndrome, Skin Cancer, Seminoma, Teratoma, Testicular Cancer, Throat Cancer, Thyroid Cancer, thoracic cancer, Urethral Cancer, Vaginal Cancer, Vulvar Cancer, Waldenstrom macroglobulinemia, and/or Wilm's tumour. In the above list, any reference to a "cancer" or a "tumour" should be understood to include a reference to a "cancer and/or a tumour" of that type.

Optionally, the brain cancer may be glioblastoma multiforme, glioblastoma, giant cell glioblastoma, recurrent gliobastoma, anaplastic astrocytoma, oligodendroglioma and/or diffuse astrocytoma.

If the cancer is breast cancer, it may optionally be selected from, for example, ductal carcinoma in situ (DCIS), lobular carcinoma in situ (LCIS), Invasive breast cancer (NST), Invasive lobular breast cancer, Inflammatory breast cancer, breast cancer associated with Paget's disease and angiosarcoma of the breast.

The cancer may be caused by, associated with, and/or characterised by a mutation or other genetic variation, which may optionally result in the altered expression of a molecule, e.g. a molecule comprising or consisting of a lipid, such as, a glycolipid or phospholipid; a carbohydrate; DNA; RNA; a protein; a polypeptide, such as, a ribosomal peptide or a non-ribosomal peptide; an oligopeptide; a lipoprotein; a lipopeptide; an amino acid; and/or a chemical compound, optionally an organic chemical compound. More particularly, a mutation may optionally result in the altered expression of a protein and/or metabolite.

A cancer may optionally express one or more metabolites that may serve as a biomarker for that cancer. For example, optionally a metabolite such as succinate, fumarate, 2-HG, and/or any of the other metabolites mentioned herein may accumulate in a cancer.

Subtypes of cancer may optionally be identified, e.g., based on such altered expression. For example, a cancer may optionally be identified as being of a particular subtype based on the expression, or lack thereof, of a receptor, e.g., selected from estrogen receptors (ER), progesterone receptors (PR) and human epidermal growth factor receptor 2 (HER2). A cancer may therefore, for example, be referred to as ER negative if it lacks expression of ER; or be referred to as triple-negative breast cancer (TNBC), if it is ER−, PR− and Her2−.

The mutation may optionally, e.g., be in a gene encoding isocitrate dehydrogenase 1 (IDH1) and/or 2 (IDH2) yielding mutant enzymes capable of converting alpha-ketoglutarate to 2-hydroxyglutarate (2-HG). Such a mutation may optionally be present, e.g., in a glioma, intrahepatic cholangiocarcinoma, acute myelogenous leukaemia (AML) and/or chondrosarcomas. 2-HG may thus be referred to as an oncometabolite. 2-HG may be present in very small small amounts in normal tissues, whereas it may be present in high concentrations, e.g., several micromoles per gram of tumor, in mutant tumours.

Optionally, the type, subtype, malignancy, stage, grade, genotype and/or phenotype of a cancer may be analysed via the methods disclosed herein.

Optionally, a lesion, optionally of any of the tissues mentioned herein, may be analysed. A lesion is region in a tissue which is abnormal as a consequence of, e.g., injury or disease. The lesion may, for example, be selected from a wound, an ulcer, an abscess, and/or a tumour. The lesion may, for example, be a diabetic lesion, such as, a diabetic limb or digit, or a diabetic ulcer.

Further examples of tissues that may be analysed are discussed elsewhere herein, e.g., tissue affected by, or in the vicinity of, cancer, necrosis, microbes and the like. For example, the tissue may optionally comprise or consist of mucosa, which is discussed elsewhere herein.

The method may optionally involve the analysis of necrosis, e.g. the analysis of tissue to determine whether a particular tissue is necrotic or healthy. Thus, the margin between healthy and necrotic tissue may optionally be analysed. This analysis may be used to assist in deciding which tissue to remove surgically and which tissue may be viable enough to be retained by the subject.

"Necrosis" is unprogrammed cell death, which may be contrasted with apoptosis, which is a form of programmed cell death.

Necrosis typically involves damage to the cell membrane and/or damage to intracellular compartments, such as, lysosomes. Necrosis is typically accompanied by the release of intracellular molecules, such as, enzymes, organic chemical molecules and the like. For example, it may include the release of the lysosomal enzymes. The release of such molecules may cause inflammation and/or damage to neighbouring cells.

The necrosis may optionally be caused by, or associated with, for example, injury, infection, cancer, infarction, toxins, inflammation, lack of proper care to a wound site, frostbite, diabetes, and/or arteriosclerosis. Optionally, the necrosis may be necrosis of cancerous or non-cancerous tissue.

The necrosis may optionally, for example, be coagulative, liquefactive, caseous, fat necrosis, fibrinoid necrosis and/or gangrenous necrosis.

Optionally, the method may involve the analysis of the cellular composition of a tissue. For example, the proportion of one or more particular cell types may be analysed. The cell types may optionally be selected from any known cell types, e.g., any of the cell types mentioned herein.

As mentioned above, the subject or biological material on which the methods disclosed herein may be performed may be referred to as a "target". A target may comprise one or more "target entities". The term "target entity" is used herein to refer to the entity which it is desired to analyse within the target. Thus, any reference to a "target" should be understood to mean a target comprising one or more different target entities. Thus, the target entity may, e.g., be a cell, microbe and/or compound. For example, the target may be a mucosal specimen, faecal specimen or body fluid on a swab and the target entity may be cancer cells and/or microbes within that mucosal specimen, faecal specimen or body fluid.

The terms "analysis", "analysing" and derivatives of these terms are used herein to encompass any of the following: detection of a target entity; identification of a target entity; characterisation of a target entity; determination of the location of target entity; determination of a status, e.g. a disease status; and/or determination of a margin between two different disease or tissue types and the like.

The analysis may be qualitative and/or quantitative. Thus, optionally, the analysis may involve determining the concentration, percentage, relative abundance or the like of the target entity. For example, the percentage of cancer cells within a tissue, the relative abundance of microbes in a target, and/or the concentration of a compound may be analysed. Optionally, an increase or decrease in a target entity may be analysed.

The terms "detection", "detecting" and derivations of these terms are used interchangeably herein to mean that the presence or absence of a target entity or biomarker therefor is determined.

The terms "identify", "identification" and derivations of these terms are used interchangeably herein to mean that information about the identity of a target entity or biomarker therefor is obtained. This may optionally be the determination of the identity, and/or the confirmation of the identity. This may optionally include information about the precise identity of the target entity or biomarker therefor. However, it may alternatively include information that allows the target entity to be identified as falling into a particular classification, as discussed elsewhere herein.

By "identifying" a microbe is meant that at least some information about the identity is obtained, which may, for example, be at any taxonomic level.

By "identifying" a cell is meant that at least some information about the cell type is obtained. By "identifying" a diseased cell is meant that it is determined or confirmed that a cell is diseased.

By "identifying" a compound is meant that at least some information about the structure and/or function of the compound is obtained, e.g., the information may optionally allow a compound to be identified as comprising or consisting of a compound selected from any of the types disclosed herein, and/or as being characterised by one or more of the functional groups disclosed herein.

The terms "diagnosis" or "diagnosing" and derivations of these terms as used herein refer to the determination whether or not a subject is suffering from a disease. Optionally, the method may involve analysing a target and, on the basis of one or more of the following making a diagnosis that a subject is or is not suffering from a particular disease: detecting a target entity; identifying a target entity; detecting an increase in a target entity; detecting a decrease in a target entity.

An increase or decrease may be determined by reference to a suitable reference, comparator or control. For example, it is known how many inflammatory cells or inflammatory molecules are typically present in the tissue of a healthy individual, so an increase in inflammatory cells or inflammatory molecules in a target may easily be determined by comparing it to a healthy control.

The term "monitoring" and derivations of this term as used herein refer to the determination whether any changes take place/have taken place. Typically, it is determined whether any changes have taken place over time, i.e. since a previous time point. The change may, for example, be the development and/or progression of a disease, such as, any of the diseases mentioned. Optionally, the method may involve analysing a target and, on the basis of one or more of the following monitoring a subject or disease: detecting a target entity; identifying a target entity; detecting an increase in a target entity; detecting a decrease in a target entity.

The term "prognosis" and derivations of this term as used herein refer to risk prediction of the severity of disease or of the probable course and clinical outcome associated with a disease. Thus, the term "method of prognosis" as used herein refers to methods by which the skilled person can estimate and/or determine a probability that a given outcome will occur. The outcome to which the prognosis relates may be morbidity and/or mortality. In particular, the prognosis may relate to "progression-free survival" (PFS), which is the length of time that a subject lives with the disease without the disease progressing. Thus, PFS may, for example, be the time from the start of therapy to the date of disease progression, or the time from the end of therapy to the date of disease progression. Optionally, the prognosis may relate to "overall survival" which is the length of time that the subject is expected to live until death.

Optionally, the method may involve analysing a target and, on the basis of one or more of the following making a prognosis: detecting a target entity; identifying a target entity; detecting an increase in a target entity; detecting a decrease in a target entity.

By "progressing" or "progression" and derivations of these terms is meant that the disease gets worse, i.e. that the severity increases. For example, in the case of cancer, it may mean that the tumour burden increases, for example a tumour increases in size and/or weight; that the cancer becomes malignant or more malignant; and/or that metastasis develops or the incidence and/or rate of metastasis increases.

The method according to various embodiments described herein may optionally be used to monitor the progress of disease.

During therapy or subsequent to therapy, the method of the various embodiments described herein may optionally be used to monitor the progress of disease to assess the effectiveness of therapy, or to monitor the progress of therapy.

Optionally, serial (periodic) analysis of a target for a change may be used to assess whether or not therapy has been effective; the extent to which therapy has been effective; whether or not a disease is re-occurring or progressing in the subject; and/or to assess the likely clinical outcome (prognosis) of the disease, should it re-occur or progress.

Optionally, the method may be used in the active monitoring of subjects which have not been subjected to therapy, e.g. to monitor the progress of the disease in untreated subjects. Optionally, serial (periodic) analysis of a target for a change may be used to assess whether or not, or the extent to which, the disease is progressing, thus, for example, allowing a more reasoned decision to be made as to whether therapeutic intervention is necessary or advisable.

Such monitoring may optionally be carried out on a healthy individual, e.g., an individual who is thought to be at risk of developing a particular disease, in order to obtain an early and ideally pre-clinical indication of the disease. Particular examples are cervical smear testing to analyse the cervix for cancer or pre-cancerous biomarkers; and/or the analysis of the vaginal mucosa to assess the risk of pregnancy complications such as preterm delivery.

Analytes/Biomarkers

The method according to various embodiments may involve the analysis of analytes, which may optionally be biomarkers. Any reference to an "analyte" should therefore be understood to encompass the embodiment that the analyte may be a biomarker. A biomarker may be an objective, quantifiable characteristic of, e.g., a cell type, disease status, microbe, compound, and/or biological process.

By "characteristic of a cell type" is meant that the biomarker may optionally be used to analyse, e.g., detect, identify and/or characterise the cell type. Optionally, the biomarker may be used to distinguish between cells originating from different tissues; between genotypically and/or phenotypically different cell types; between an animal cell and a microbial cell; between a normal and an abnormal cell; between a wild-type and a mutant cell; and/or between a diseased and a healthy cell.

By "characteristic of a disease status" is meant that the biomarker may optionally be used to analyse the disease status of a target. Optionally, the biomarker may be used to distinguish between healthy and diseased cells; and/or to analyse the severity, grade, and/or stage of a disease.

By "characteristic of a microbe" is meant that the biomarker may optionally be used to analyse, e.g., detect, identify and/or characterise the microbe. As discussed elsewhere herein, identification may be on any level, for example, on a taxonomic level. A biomarker that allows identification of a microbe as belonging to a particular taxonomic level may be referred to as a "taxonomic marker" or "taxonomic biomarker". Thus, a taxonomic marker may be specific for a Kingdom, Phylum, Class, Order, Family, Genus, Species and/or Strain.

By "characteristic of a compound" is meant that the biomarker may optionally be used to analyse, e.g., detect, identify and/or characterise the compound.

By "characteristic of a biological process" is meant that the biomarker may optionally be used to analyse a biological process. Optionally, the biomarker may be used to analyse the start, progression, speed, efficiency, specificity and/or end of a biological process.

Different cell types, disease states, compounds, microbes, biological progresses and the like may be characterised by the presence or absence, and/or relative abundance, of one or more compounds, which may serve as biomarkers. Any reference herein to a biomarker being a particular compound, or class of compounds, should be understood optionally to be the mass spectral data of that compound, or class of compounds.

For example, a reference to a "C24:1 sulfatide $(C_{48}H_{91}NO_{11}S)$" biomarker should be understood to be a reference to the mass spectral data corresponding to C24:1 sulfatide $(C_{48}H_{91}NO_{11}S)$ which may, e.g., be a signal at m/z of about 888.6; whereas a reference to a "glycosylated ceramide" biomarker should be understood to be a reference to the mass spectral data corresponding to glycosylated ceramide, which may, e.g., be a signal at m/z of 842, 844 or 846.

As explained above, a biomarker may be indicative of a cell type, disease status, microbe, compound, and/or biological process. A biomarker which is indicative of cancer may therefore be referred to as a "cancer biomarker"; a biomarker which is indicative of Pseudomonas aeruginosa may be referred to as a "Pseudomonas aeruginosa biomarker" and so on.

Optionally, a mass spectral biomarker may be identified as being the mass spectral data of a particular compound, or class of compounds. Thus, a signal at a particular m/z may optionally be identified as being indicative of the presence of a particular compound, or class of compounds. This may optionally involve a step of MS-MS analysis.

Optionally, mass spectral signal may serve as a biomarker even if a determination has not been made as to which particular compound, or class of compounds gave rise to that signal. Optionally, a pattern of mass spectral signals may serve as a biomarker even if a determination has not been made as to which particular compounds, or class of compounds, gave rise to one or more signals in that pattern, or any of the signals in a pattern.

The work disclosed herein has led to the identification of a range of biomarkers, as well as allowing the identification of further biomarkers. Optionally, the biomarker may be selected from any of the biomarkers disclosed herein.

Optionally, the biomarker may be a biomarker of a lipid; a protein; a carbohydrate; a DNA molecule; an RNA molecule; a polypeptide, such as, a ribosomal peptide or a non-ribosomal peptide; an oligopeptide; a lipoprotein; a lipopeptide; an amino acid; and/or a chemical compound, optionally an organic chemical molecule or an inorganic chemical molecule.

A biomarker may optionally be the clear-cut presence or absence of a particular compound, which may optionally manifest itself as the presence or absence of a mass spectral signal at a specific m/z.

A biomarker may optionally be the relative abundance of a particular biomolecule or compound, which may optionally manifest itself as the relative intensity of a mass spectral signal at a specific m/z.

A biomarker may optionally be the relative abundance of more or more compounds, which may optionally manifest itself as the relative intensity of two or more mass spectral signals at two or more m/z.

Thus, a biomarker may optionally be an increased or decreased level of one or more compounds, e.g., a metabolite, a lipopeptide and/or lipid species, which may optionally manifest itself as an increase and/or decrease in the intensity of two or more mass spectral signals at two or more m/z.

The presence, absence and relative abundance of a variety of compounds may be referred to as a molecular "fingerprint" or "profile". The totality of the lipids of a cell may be referred to as a lipidomic fingerprint/profile, whereas the totality of metabolites produced by a cell may be referred to as a metabolomic fingerprint/profile.

Thus, the biomarker may be a molecular fingerprint, e.g., a lipid fingerprint and/or a metabolomic fingerprint, more particularly e.g., a (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; (viii) a phosphatidylinositol (PI) profile; or (ix) a triglyceride (TG) profile.

A lipid biomarker may optionally be selected from, e.g., fatty acids, glycerolipids, sterol lipids, sphingolipids, prenol lipids, saccharolipids and/or phospholipids.

By "metabolome" is meant a collection of the metabolites produced by a cell. The metabolome may be the entirety of the cell's metabolites, or a particular subset thereof, e.g. the subset of the 3, 4, 5, 6, 7, 8, 9, 10, 15, 20, 25, 30, 35, 40, 50, 60, 70, 80, 90 or 100 most abundant metabolites produced by that cell. Metabolomics is the study of the metabolome. A metabolomic marker is a marker of one or more metabolites, or of the metabolome.

Analysis of Compounds

The method according to various embodiments may optionally involve the analysis of one or more compounds that may be present in the biological sample, e.g. the mucosa, the biopsy, the body fluid and/or the faecal specimen. Thus, the method may involve the analysis of the presence or absence, and/or the relative abundance and/or distribution, of one or more compounds.

Unless otherwise stated, the terms "compound", "molecule", "substance" and "biomolecule" are used interchangeably herein.

The compound may optionally be intracellular and/or extracellular. It may optionally be endogenous, i.e. produced by the subject or microbe, and/or exogenous, i.e. added to the subject, tissue, cell, and/or microbe.

The compound may optionally comprise or consist of any of the compounds or classes of compounds mentioned herein, e.g. any of the biomarkers mentioned herein. Optionally, it may comprise or consist of, for example, a lipid, such as, a glycolipid or phospholipid; carbohydrate; DNA; RNA; protein; polypeptide, such as, a ribosomal peptide or a non-ribosomal peptide; oligopeptide; lipoprotein; lipopeptide; amino acid; and/or chemical molecule, optionally an organic chemical molecule.

The compound may optionally be linear, cyclic or branched.

The compound may optionally be a metabolite, such as, a primary or a secondary metabolite; an antibiotic; a quorum sensing molecule; a fatty acid synthase product; a pheromone; and/or a biopolymer.

The compound may optionally be characterised by one or more of the following functional groups: alcohol, ester, alkane, alkene, alkyne, ether, ketone, aldehyde, anhydride, amine, amide, nitrile, aromatic, carboxylic acid, alkyl halide, and/or carbonyl. Optionally, it may additionally be identified as being primary, secondary or tertiary, e.g., a primary alcohol, a secondary amine, or the like.

Optionally, the compound may be a therapeutic drug, an illicit drug, a doping agent, and/or a metabolite or derivative of any thereof.

It may optionally be selected, e.g., from any of the drugs or agents mentioned herein, and/or Mescaline, PCP (Phencyclidine), Psilocybin, LSD, Heroin, Morphine, Codeine, dextroamphetamine, bupropion, cathinone, lisdexamfetamine, Allobarbital, Alphenal (5-allyl-5-phenylbarbituric acid), Amobarbital, Aprobarbital, Brallobarbital, Butobarbital, Butalbital, Cyclobarbital, Methylphenobarbital, Mephobarbital, Methohexital, Pentobarbital, Phenobarbital, Secobarbital, Talbutal, Thiamylal, and/or Thiopental. Ranitidine, phenylalanine PKU, dimethylamylamine, cocaine, diazepam, androstadienedione, stigmastadienone, androsterone-hemisuccinate, 5α-androstan-3β,17β-diol-16-one, androsterone glucuronide, epitestosterone, 6-dehydrocholestenone, phenylalanine, leucine, valine, tyrosine, methionine, sitamaquine, terfenadine, prazosin, methadone, amitripyline, nortriptyline, pethidine, DOPA, ephedrine, ibuprofen, propranolol, atenolol, acetaminophen, bezethonium, citalopram, dextrorphan, paclitaxel, proguanil, simvastatin, sunitinib, telmisartan, verapamil, amitriptyline, pazopanib, tamoxifen, imatinib, cyclophosphamide, irinotecan, docetaxel, topotecan, acylcarnitines (C2-C18), nicotine, cotinine, trans-3'-hydroxycotinine, anabasine, amphetamine, amphetamine-like stimulants, methamphetamine, MDA, MDMA, MDEA, morphine, $\Delta^9$-THC, tacrolimus, benzethonium, meprobamate, O-desmethyl-cis-tramadol, carisoprodol, tramadol, nordiazepam, EDDP, norhydrocodone, hydromorphone, codeine, temazepam, noroxycodone, alprazolam, oxycodone, buprenorphine, norbuprenorphine, fentanyl, propoxyphene, 6-monoacetylmorphine, caffeine, carbadox, carbamazepine, digoxigenin, diltiazem, diphenhydramine, propanolol, sulfadiazine, sulfamethazine, sulfathiazole, thiabendazole, ketamine, norketamine, BZE, AMP, MAMP, and/or 6-MAM.

Although the present invention has been described with reference to preferred embodiments, it will be understood by those skilled in the art that various changes in form and detail may be made without departing from the scope of the invention as set forth in the accompanying claims.

The invention claimed is:

1. A method comprising:
   providing a biological sample on a swab, wherein said swab has been chemically modified to enhance selectivity for an analyte;
   directing a spray of charged droplets onto a surface of said swab in order to generate a plurality of analyte ions, wherein directing said spray of charged droplets onto said swab comprises ionising said sample using Desorption Electrospray Ionisation ("DESI") or desorption electroflow focusing ionisation ("DEFFI");
   mass analysing and/or ion mobility analysing said analyte ions or ions derived from said analyte ions in order to obtain mass spectrometric and/or ion mobility data; and
   analysing said mass spectrometric data and/or said ion mobility data.

2. The method as claimed in claim 1, wherein the step of analysing said mass spectrometric data and/or said ion mobility data comprises using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; and (xxii) subspace discriminant analysis; (xxiii) k-nearest neighbours (KNN); (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

3. The method as claimed in claim 1, wherein said chemical modification renders said swab lipophilic.

4. The method as claimed in claim 1, wherein said chemical modification involves formation of a coating on a surface of the swab.

5. The method as claimed in claim 4, wherein said coating is a polymeric coating.

6. The method as claimed in claim 5, wherein said polymer coating comprises polydivinylbenzene (DVB), a copolymer of N-vinylpyrrolidone and divinylbenzene, or polydimethylsiloxane.

7. The method as claimed in claim 5, wherein said polymeric coating contains particles of a solid-phase extraction material.

8. The method as claimed in claim 1, wherein said chemical modification utilises a solid-phase extraction material.

9. The method as claimed in claim 8, wherein said solid-phase extraction material comprises polymer particles, silica particles, hybrid silica/organic particles, carbon particles or polymer-coated solid particles.

10. The method as claimed in claim 1, comprising directing said spray of charged droplets onto said swab from a sprayer.

11. The method as claimed in claim 10, further comprising providing said sprayer with a solvent at a flow rate in the range (i) <5 µL/min; (ii) 5-7 µL/min; (iii) 7-9 µL/min; (iv) 9-10 µL/min; (v) 10-11 µL/min; (vi) 11-13 µL/min; (vii) 13-15 µL/min; or (viii) 15-20 µL/min.

12. The method as claimed in claim 1, further comprising rotating said swab whilst directing said spray of charged droplets onto said surface of said swab, optionally wherein said step of rotating said swab whilst directing said spray of charged droplets onto said surface of said swab comprises substantially continuously rotating said swab whilst directing said spray of charged droplets onto said surface of said swab.

13. The method as claimed in claim 1, further comprising translating and/or oscillating said swab whilst directing said spray of charged droplets onto said surface of said swab, optionally wherein said step of translating and/or oscillating said swab comprises substantially continuously translating and/or oscillating said swab whilst directing said spray of charged droplets onto said surface of said swab.

14. The method as claimed in claim 1, wherein the step of analysing said mass spectrometric data and/or said ion mobility data comprises performing a supervised and/or unsupervised analysis of said mass spectrometric data.

15. An apparatus comprising:
a first device arranged and adapted to direct a spray of charged droplets onto a surface of a swab in order to generate a plurality of analyte ions, wherein said first device comprises a Desorption Electrospray Ionisation ("DESI") ion source or a desorption electroflow focusing ionisation ("DEFFI") ion source and wherein said swab has been chemically modified to enhance selectivity for an analyte; and
a mass analyser and/or ion mobility analyser for mass analysing and/or ion mobility analysing said analyte ions or ions derived from said analyte ions in order to obtain mass spectrometric and/or ion mobility data.

16. The apparatus as claimed in claim 15, wherein said mass spectrometric data and/or ion mobility data is analysed using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; and (xxii) subspace discriminant analysis; (xxiii) k-nearest neighbours (KNN); (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

* * * * *